US008309550B2

(12) United States Patent
Luo et al.

(10) Patent No.: US 8,309,550 B2
(45) Date of Patent: Nov. 13, 2012

(54) KINASE INHIBITORS AND THEIR USE AS PHARMACEUTICAL AGENTS

(75) Inventors: Ying Luo, Shanghai (CN); Fang Shu, Shanghai (CN); Shudong Wang, Nottingham (GB)

(73) Assignee: Shanghai Genomics, Inc., Shanghai (CN)

( * ) Notice: Subject to any disclaimer, the term of this patent is extended or adjusted under 35 U.S.C. 154(b) by 0 days.

(21) Appl. No.: 13/095,526

(22) Filed: Apr. 27, 2011

(65) Prior Publication Data

US 2011/0263541 A1 Oct. 27, 2011

(51) Int. Cl.
*C07D 403/04* (2006.01)
*A61K 31/437* (2006.01)

(52) U.S. Cl. ............... 514/235.8; 514/252.14; 514/275; 544/122; 544/295; 544/331

(58) Field of Classification Search .................. 544/122, 544/295, 331; 514/235.8, 252.14, 275
See application file for complete search history.

(56) References Cited

FOREIGN PATENT DOCUMENTS

| CN | 101014600 A | | 8/2007 |
| WO | WO 95/09847 | | 4/1995 |
| WO | WO 2006/075152 | * | 7/2006 |
| WO | WO 2006/124863 | * | 11/2006 |
| WO | WO 2007/107221 A1 | | 9/2007 |
| WO | WO 2009/092431 | * | 7/2009 |
| WO | WO 2010/042337 | * | 4/2010 |

OTHER PUBLICATIONS

Bundgaard, Design of Prodrugs, p. 1, 1985.*
Wolff, Some consideration for prodrug design, Burger's Medicinal Chemistry and Drug Discovery, 5th Edition, vol. I: Principles and Practice, pp. 975-977, 1995.*
Banker et al., Prodrugs, Modern Pharmaceutics, Third Edition and Expanded, pp. 451 and 596.*
Simone, Oncology: Introduction, Cecil Textbook of Medicine, 20th Edition, vol. 1, pp. 1004-1010, 1996.*
Rogers et al., PubMed Abstract (J Cell Biol. 157(2):219-29, Epub) Apr. 2002.*
Tanaka et al., PubMed Abstract (Cell 108(3):317-29) Feb. 2002.*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*
Caravajal et al., Aurora Kinases: New Targets for Cancer Therapy, Clin Cancer Res 2006:12(23), pp. 6869-6875, Dec. 1, 2006.*
Silverman, Prodrugs and Drug Delivery Systems, The Organic Chemistry of Drug Design and Drug Action, pp. 352-399, 1992.*
Ulrich, Chapter 4: Crystallization, Kirk-Othmer Encyclopedia of Chemical Technology, Aug. 2002.*
West, Solid Solutions, Solid State Chemistry and its applications, pp. 358 & 365, 1988.*
Vippagunta et al., Cyrstalline Solids, Advanced Drug Delivery Reviews, 48, pp. 3-26, 2001.*
LuValle et al., "Cell Cycle Control in Growth Plate Chondocytes", Frontiers in Bioscience 5, d493-503 (May 2000).*
Blain et al., Different Integration of the Cyclin-dependent kinase (CDK) inhibitor p27Kipi with Cyclin A-Cdk2 and Cyclin D2-Cdk4, The Journal of Biological Chemistry, 272(41):25863-72 (1997).*
Xiao et al., Retroviral oncoprotein Tax induces processing of NF-kB2/p100 in T-cells: evidence for the involvement of IKKalpha, The EMBO Journal, vol. 20, No. 23, pp. 6805-6815, 2001.*
Hyung-Ho Ha, et al., Novel heterocycle-substituted pyrimidines as inhibitors of NF-κB transcription regulation related to TNF—α cytokine release., Bioorganic & Medicinal Chemistry Letters 18 (2008) 653-656.

* cited by examiner

*Primary Examiner* — Deepak Rao
(74) *Attorney, Agent, or Firm* — McDermott Will & Emery LLP

(57) ABSTRACT

Described herein are compounds that are inhibitors of one or more protein kinases. Also described are pharmaceutical compositions and medicaments that include the compounds described herein. Also described herein are methods of using such protein kinase inhibitors, alone and in combination with other compounds, for conditions or diseases mediated or dependent upon protein kinases.

9 Claims, 8 Drawing Sheets

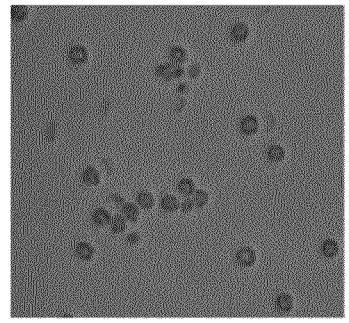
Fig 4A
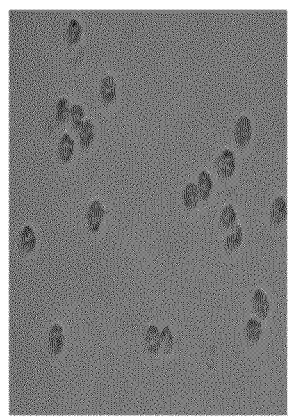 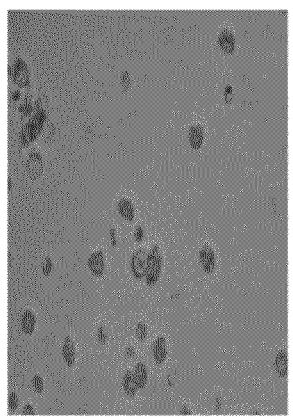 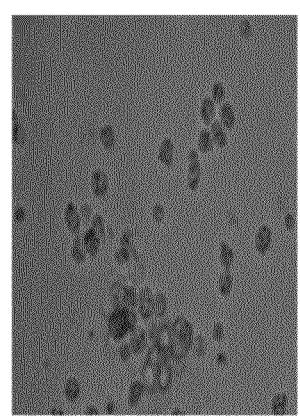
Fig 4B  Fig 4C  Fig 4D
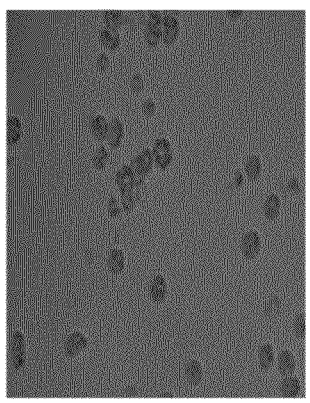 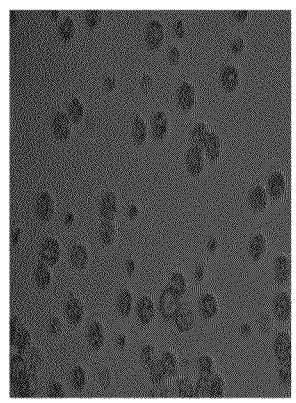 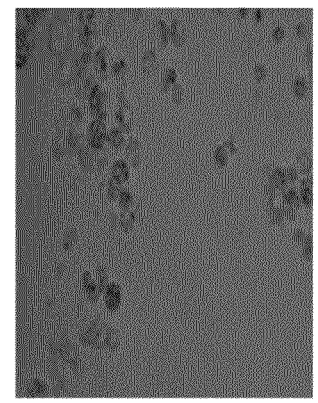
Fig 4E  Fig 4F  Fig 4G

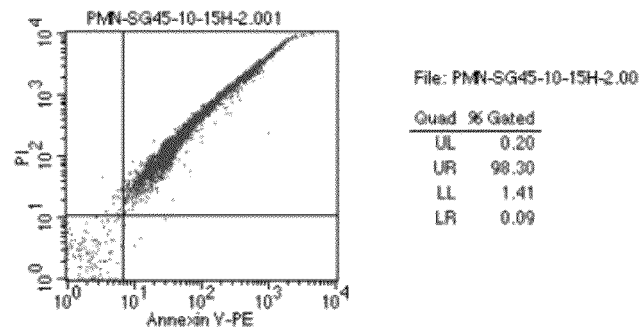
Fig 5G
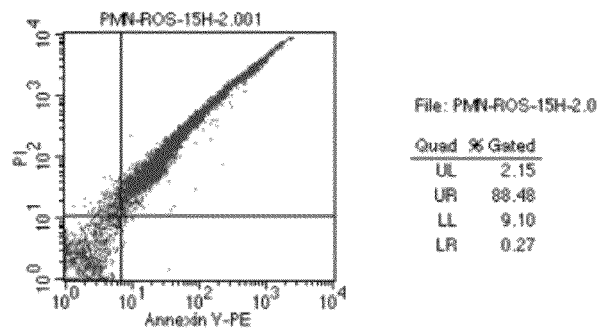
Fig 5H
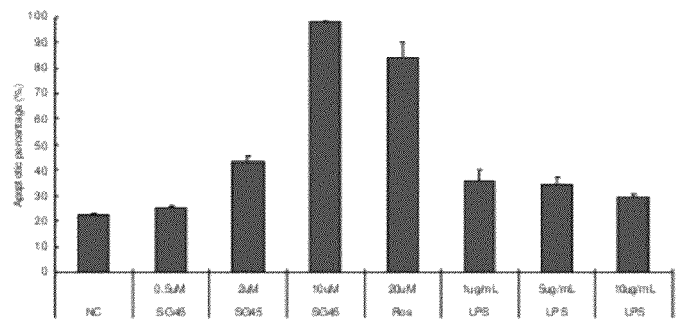
Fig 5I
Fig 5

KINASE INHIBITORS AND THEIR USE AS PHARMACEUTICAL AGENTS

FIELD OF THE INVENTION

Described herein are compounds, methods of making such compounds, pharmaceutical compositions and medicaments comprising such compounds, and methods of using such compounds to treat, prevent or diagnose diseases, disorders or conditions associated with one or more protein kinases.

BACKGROUND OF THE INVENTION

Many diseases are associated with abnormal cellular responses triggered by protein kinase-mediated events. These diseases include, but are not limited to allergies, asthma, Alzheimer's disease, autoimmune diseases, bone diseases, cancer, cardiovascular diseases, inflammatory diseases, hormone-related diseases, metabolic diseases, neurological and neurodegenerative diseases. Described herein are protein kinase inhibitors that are effective as therapeutic agents. Some CDK inhibitors have effect of overriding pro-inflammatory signalling and driving neutrophil apoptosis. These inhibitors include, but are not limited to Roscovitine. R-roscovitine could enhance resolution of carrageenan-induced pleurisy. And R-rescovitine also had effect on resolution of bleomycin-induced lung inflammation and serum-induced arthritis. (Rossi et al, Nat. Med. (2006) 12:9 1056-1064) The cyclin-dependent kinase inhibitor R-roscovitine down-regulated Mcl-1 to override pro-inflammatory signalling and drive neutrophil apoptosis. (Andrew E. Leitch, et al, Eur. J. Immunol. 2010 40: 1127-1138) CDK9 promotes RNA synthesis in genetic programmes for cell growth, differentiation and viral pathogenesis. CDK9 inhibition contributes to the anticancer activity of most CDK inhibitors under clinic investigation. CDK9 inhibitors might become specific antiretroviral agents, particularly as they might prevent drug resistance. But it is still lack of selective inhibitors in clinical development, which means a need of offering a more effective agent for preventing and treating inflammatory disorders is an exigent task in the art.

SUMMARY OF THE INVENTION

Presented herein are compounds, pharmaceutical compositions, medicaments, and methods, for (a) diagnosing, preventing, or treating conditions, disorders, or disorders associated with one or more protein kinases, (b) mitigating adverse signs and symptoms that are associated with one or more protein kinases, and/or (c) controlling conditions, disorders, or disorders associated with one or more protein kinases. These conditions, disorders, or disorders may arise from one or more of a genetic, iatrogenic, immunological, infectious, metabolic, oncological, toxic, surgical, and/or traumatic etiology. In one aspect, the methods, compounds, pharmaceutical compositions, and medicaments described herein comprise inhibitors of one or more protein kinases.

In one aspect is a compound having the structure of Formula (I), pharmaceutically acceptable salts, pharmaceutically acceptable solvates, or pharmaceutically acceptable prodrugs thereof:

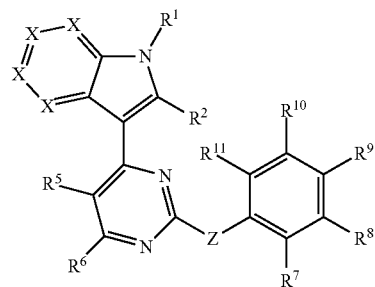

Formula (I)

wherein each X is —C($R^3$)— or —N—, provided that at least two X are —C($R^3$)—;

Z is —$NR^a$C(=O)—, —C(=O)$NR^a$—, —$NR^a$SO$_2$—, —SO$_2NR^a$—, —$NR^a$—, —CH$_2NR^a$—, —$NR^a$CH$_2$—, —CH$_2$—, —CH$_2$CH$_2$—, —CH=CH—, —CH$_2$C(=O)$NR^a$—, —$NR^a$C(=O)CH$_2$—, —SO$_2$—, or —SO—;

$R^a$ is H or alkyl;

$R^1$, $R^2$, $R^3$, $R^5$, $R^6$, $R^7$, $R^8$, $R^9$, $R^{10}$ and $R^{11}$ are each independently selected from the group consisting of H, halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, —CF$_3$, —CH$_3$, and -$L^A$-$L^B$-$R^{32}$; $L^A$ is a covalent bond or an alkyl group; $L^B$ is a covalent bond, —O—, —$NR^{32}$—, —NH—, —C(=O)—, —C(=O)O—, —OC(=O)—, —C(=O)$NR^{32}$—, —C(=O)NH—, —$NR^{32}$C(=O)—, —NHC(=O)—, —SO$_2$—, —SO$_2NR^{32}$—, —$NR^{32}$SO$_2$—, —SO$_2$NH—, or —NHSO$_2$—; $R^{32}$ is H, substituted or unsubstituted alkyl, haloalkyl, substituted or unsubstituted aryl, substituted or unsubstituted heteroaryl, substituted or unsubstituted non-aromatic heterocycle, or substituted or unsubstituted cycloalkyl; wherein any $R^{32}$ group, when substituted, is substituted with one or more groups selected from halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, and —CF$_3$.

In some embodiments, Z is —$NR^a$—. In one aspect, $R^a$ is H.

In one aspect, $R^5$ and $R^6$ are each H.

In some embodiments, $R^2$ is H.

In some embodiments, each $R^3$ is independently selected from the group consisting of H, halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, —CF$_3$, and —CH$_3$.

In some embodiments, $R^7$, $R^8$, $R^9$, $R^{10}$ and $R^{11}$ are each independently selected from the group consisting of H, halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, —CF$_3$, —CH$_3$, and -$L^A$-$L^B$-$R^{32}$; $L^A$ is a covalent bond or an alkyl group; $L^B$ is a covalent bond, —O—, —$NR^{32}$—, —NH—, —C(=O)O—, —C(=O)NH—, or —SO$_2$NH—; $R^{32}$ is H, substituted or unsubstituted alkyl, haloalkyl, substituted or unsubstituted aryl, substituted or unsubstituted heteroaryl; wherein any $R^{32}$ group, when substituted, is substituted with one or more groups selected from halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, and —CF$_3$.

In one aspect, described herein is a compound, or pharmaceutically acceptable salt, solvate, or prodrug thereof, having the structure of Formula (Ia):

Formula (Ia)

wherein:
X is —C(R$^3$)— or —N—;
R$^1$ is unsubstituted C$_1$-C$_6$ alkyl, unsubstituted or substituted aryl, or unsubstituted or substituted heteroaryl;
R$^2$, R$^3$, R$^5$, R$^6$, R$^7$, R$^8$, R$^9$, R$^{10}$ and R$^{11}$ are each independently selected from the group consisting of H, halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, —CF$_3$, —CH$_3$, and -L$^A$-L$^B$-R$^{32}$;
L$^A$ is a covalent bond or an alkyl group;
L$^B$ is a covalent bond, —O—, —NR$^{32}$—, —NH—, —C(=O)—, —C(=O)O—, —OC(=O)—, —C(=O)NR$^{32}$—, —C(=O)NH—, —NR$^{32}$C(=O)—, —NHC(=O)—, —SO$_2$—, —SO$_2$NR$^{32}$—, —NR$^{32}$SO$_2$—, —SO$_2$NH—, or —NHSO$_2$—;
R$^{32}$ is H, substituted or unsubstituted alkyl, haloalkyl, substituted or unsubstituted aryl, substituted or unsubstituted heteroaryl, substituted or unsubstituted non-aromatic heterocycle, or substituted or unsubstituted cycloalkyl;
wherein any R$^{32}$ group, when substituted, is substituted with one or more groups selected from halogen, —NH$_2$, —NO$_2$, —CN, —OH, —CO$_2$H$_2$, —CONH$_2$, —SO$_3$H, —SO$_2$NH$_2$, —SO$_2$CH$_3$, —OCH$_3$, and —CF$_3$;
Z is —NR$^a$C(=O)—, —C(=O)NR$^a$—, —NR$^a$SO$_2$—, —SO$_2$NR$^a$—, —NR$^a$—, —CH$_2$NR$^a$—, —NR$^a$CH$_2$—, —CH$_2$—, —CH$_2$CH$_2$—, —CH=CH—, —CH$_2$C(=O)NR$^a$—, —NR$^a$C(=O)CH$_2$—, —SO$_2$—, or —SO—;
R$^a$ is H or alkyl.
In one aspect, X is N. In another aspect, X is —C(R$^3$)—.
In some embodiments. Z is —NR$^a$—.
In some embodiments, R$^1$ is unsubstituted C$_1$-C$_6$ alkyl or unsubstituted or substituted phenyl. In some other embodiments, R$^1$ is unsubstituted C$_1$-C$_6$ alkyl.
In some embodiments, each R$^3$ is independently selected from the group consisting of H, halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, —CF$_3$, and —CH$_3$.
In some embodiments, R$^2$, R$^5$ and R$^6$ are each H.
In other embodiments, R$^7$, R$^8$, R$^9$, R$^{10}$ and R$^{11}$ are each independently selected from the group consisting of H, halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, —CF$_3$, —CH$_3$, and -L$^A$-L$^B$-R$^{32}$; L$^A$ is a covalent bond or an alkyl group; L$^B$ is a covalent bond, —O—, —NR$^{32}$—, —NH—, —C(=O)O—, —C(=O)NR$^{32}$—, —C(=O)NH—, —SO$_2$NR$^{32}$—, or —SO$_2$NH—; R$^{32}$ is H, substituted or unsubstituted alkyl, haloalkyl, substituted or unsubstituted aryl, substituted or unsubstituted heteroaryl, substituted or unsubstituted non-aromatic heterocycle, or substituted or unsubstituted cycloalkyl; wherein any R$^{32}$ group, when substituted, is substituted with one or more groups selected from halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, and —CF$_3$.

In one aspect, provided herein is a compound, or pharmaceutically acceptable salt, solvate, or prodrug thereof, having the structure of Formula (Ib):

Formula (Ib)

wherein:
R$^1$, R$^2$, R$^3$, R$^5$, R$^6$, R$^7$, R$^8$, R$^9$, R$^{10}$ and R$^{11}$ are each independently selected from the group consisting of H, halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, —CF$_3$, —CH$_3$, and -L$^A$-L$^B$-R$^{32}$;
L$^A$ is a covalent bond or an alkyl group;
L$^B$ is a covalent bond, —O—, —NR$^{32}$—, —NH—, —C(=O)—, —C(=O)O—, —OC(=O)—, —C(=O)NR$^{32}$—, —C(=O)NH—, —NR$^{32}$C(=O)—, —NHC(=O)—, —SO$_2$—, —SO$_2$NR$^{32}$—, —NR$^{32}$SO$_2$—, —SO$_2$NH—, or —NHSO$_2$—;
R$^{32}$ is H, substituted or unsubstituted alkyl, haloalkyl, substituted or unsubstituted aryl, substituted or unsubstituted heteroaryl, substituted or unsubstituted non-aromatic heterocycle, or substituted or unsubstituted cycloalkyl;
wherein any R$^{32}$ group, when substituted, is substituted with one or more groups selected from halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, and —CF$_3$;
Z is —NR$^a$C(=O)—, —C(=O)NR$^a$—, —NR$^a$SO$_2$—, —SO$_2$NR$^a$—, —NR$^a$—, —CH$_2$NR$^a$—, —NR$^a$CH$_2$—, —CH$_2$—, —CH$_2$CH$_2$—, —CH=CH—, —CH$_2$C(=O)NR$^a$—, —NR$^a$C(=O)CH$_2$—, —SO$_2$—, or —SO—;
R$^a$ is H or alkyl.
In some embodiments, Z is —NR$^a$—.
In some embodiments, R$^1$ is unsubstituted C$_1$-C$_6$ alkyl.
In some embodiments, each R$^3$ is independently selected from the group consisting of H, halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, —CF$_3$, and —CH$_3$.
in other embodiments, R$^2$, R$^5$ and R$^6$ are each H.
In some embodiments, R$^7$, R$^8$, R$^9$, R$^{10}$ and R$^{11}$ are each independently selected from the group consisting of H, halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, —CF$_3$, —CH$_3$, and -L$^A$-L$^B$-R$^{32}$, L$^A$ is a covalent bond or an alkyl group: L$^B$ is a covalent bond, —O—, —NR$^{32}$—, —NH—, —C(=O)O—, —C(=O)NR$^{32}$—, —C(=O)NH—, —SO$_2$NR$^{32}$—, or —SO$_2$NH—; R$^{32}$ is H, substituted or unsubstituted alkyl, haloalkyl, substituted or unsubstituted aryl, substituted or unsubstituted heteroaryl, substituted or unsubstituted non-aromatic heterocycle, or substituted or unsubstituted cycloalkyl; wherein any R$^{32}$ group, when substituted, is substituted with one or more groups selected from halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, and —CF$_3$.

In one aspect, provided herein is a compound, or pharmaceutically acceptable salt, solvate, or prodrug thereof, having the structure of Formula (Ic):

Formula (Ic)

wherein:
R$^1$, R$^2$, R$^3$, R$^5$, R$^6$, R$^7$, R$^8$, R$^9$, R$^{10}$ and R$^{11}$ are each independently selected from the group consisting of H, halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, —CF$_3$, —CH$_3$, and -L$^A$-L$^B$-R$^{32}$;
L$^A$ is a covalent bond or an alkyl group;
L$^B$ is a covalent bond, —O—, —NR$^{32}$—, —NH—, —C(=O)—, —C(=O)O—, —OC(=O)—, —C(=O)NR$^{32}$—, —C(=O)NH—, —NR$^{32}$C(=O)—, —NHC(=O)—, —SO$_2$—, —SO$_2$NR$^{32}$—, —NR$^{32}$SO$_2$—, —SO$_2$NH—, or —NHSO$_2$—;
R$^{32}$ is H, substituted or unsubstituted alkyl, haloalkyl, substituted or unsubstituted aryl, substituted or unsubstituted heteroaryl, substituted or unsubstituted non-aromatic heterocycle, or substituted or unsubstituted cycloalkyl;
wherein any R$^{32}$ group, when substituted, is substituted with one or more groups selected from halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, and —CF$_3$;
Z is —NR$^a$C(=O)—, —C(=O)NR$^a$—, —NR$^a$SO$_2$—, —SO$_2$NR$^a$—, —NR$^a$—, —CH$_2$NR$^a$—, —NR$^a$CH$_2$—, —CH$_2$—, —CH$_2$CH$_2$—, —CH=CH—, —CH$_2$C(=O)NR$^a$—, —NR$^a$C(=O)CH$_2$—, —SO$_2$—, or —SO—;
R$^a$ is H or alkyl.

In some embodiments, Z is —NR$^a$—.
In some embodiments, R$^1$ is unsubstituted C$_1$-C$_6$ alkyl.
In some embodiments, each R$^3$ is independently selected from the group consisting of H, halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, —CF$_3$, and —CH$_3$.
In some embodiments, R$^2$, R$^5$ and R$^6$ are each H.
In some other embodiments, R$^7$, R$^8$, R$^9$, R$^{10}$ and R$^{11}$ are each independently selected from the group consisting of H, halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, —CF$_3$, —CH$_3$, and -L$^A$-L$^B$-R$^{32}$, L$^A$ is a covalent bond or an alkyl group; L$^B$ is a covalent bond, —O—, —NR$^{32}$—, —NH—, —C(=O)O—, —C(=O)NR$^{32}$—, —C(=O)NH—, —SO$_2$NR$^{32}$—, or —SO$_2$NH—; R$^{32}$ is H, substituted or unsubstituted alkyl, haloalkyl, substituted or unsubstituted aryl, substituted or unsubstituted heteroaryl, substituted or unsubstituted non-aromatic heterocycle, or substituted or unsubstituted cycloalkyl; wherein any R$^{32}$ group, when substituted, is substituted with one or more groups selected from halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, and —CF$_3$.

In some embodiments, L$^A$ is a covalent bond.
In some embodiments. L$^B$ is a covalent bond, —O—, —NH—, —C(=O)O—, —C(=O)NH—, or —SO$_2$NH—.
In some embodiments. R$^{32}$ is H, substituted or unsubstituted alkyl, or haloalkyl; wherein any R$^{32}$ group, when substituted, is substituted with one or more groups selected from halogen, —NH$_2$, —NO$_2$, —CN, —OH, —CO$_2$H, —CONH$_2$, —SO$_3$H, —SO$_2$NH$_2$, —SO$_2$CH$_3$, —OCH$_3$, and —CF$_3$. In some embodiments, R$^{32}$ is H, substituted or unsubstituted alkyl, or haloalkyl.

In one aspect, R$^1$, R$^3$, R$^7$, R$^8$, R$^9$, R$^{10}$, R$^{11}$ are as defined in Table 1, Table 2, Table 3 and Table 4. In one aspect, R$^2$, R$^5$, and R$^6$ are each H and R$^1$, R$^3$, R$^7$, R$^8$, R$^9$, R$^{10}$, R$^{11}$ are as defined in Table 1, Table 2, Table 3 and Table 4.

Any combination of the groups described above for the various variables is contemplated herein.

In one aspect, the compound of Formula (I) inhibits at least one kinase selected from among a Cyclin-dependent kinase (CDK), a Glycogen synthase kinase (GSK), an aurora kinase, a polo-like kinase (PLK), BCR-ABL, IkappaB kinase complex (IKK), Fms-like tyrosine kinase 3 (FLT3), Janus kinase (JAK), lymphocyte-specific protein tyrosine kinase (LCK), Platelet-derived growth factor receptor kinase (PDGFR), a Src kinase, and vascular endothelial growth factor (VEGF) receptor.

In one aspect, provided is a pharmaceutical composition comprising a compound of Formula (I) and a pharmaceutically excipient.

In one aspect, the pharmaceutical composition is in the form of an aqueous dispersion, liquid, gel, syrup, elixir, slurry, suspension, aerosol, controlled release formulation, fast melt formulation, effervescent formulation, lyophilized formulation, tablet, powder, pill, dragee, capsule, delayed release formulation, extended release formulation, pulsatile release formulation, multiparticulate formulation, or immediate release formulation.

In one aspect, provided is a method for treating or preventing a kinase mediated or kinase dependent disease, disorder or condition in a patient, comprising administrating to the patient an effective amount of a compound of Formula (I). In one aspect, the kinase is selected from among a Cyclin-dependent kinase (CDK), a Glycogen synthase kinase (GSK), an aurora kinase, a polo-like kinase (PLK), BCR-ABL, IkappaB kinase complex (IKK), Fms-like tyrosine kinase 3 (FLT3), Janus kinase (JAK), lymphocyte-specific protein tyrosine kinase (LCK), Platelet-derived growth factor receptor kinase (PDGFR), a Src kinase, and vascular endothelial growth factor (VEGF) receptor. In some embodiments, the kinase is a Cyclin-dependent kinase (CDK). In some embodiments, the kinase mediated or kinase dependent disease, disorder or condition is a proliferative disorder. In some embodiments, the proliferative disorder is cancer or leukemia. In some embodiments, the proliferative disorder is cancer or leukemia selected from cervical cancer, osteosarcoma, esophageal cancer, liver cancer, myelogenous leukaemia, melanoma, acute lymphoblastic leukemia, lung cancer, breast cancer, or renal cancer.

In one aspect, provided is a pharmaceutical composition comprising an amount of a compound of Formula (I) effective for inhibiting cyclin-dependent kinase 2 activity in a cell, and a pharmaceutically acceptable excipient.

In one aspect, provided is a method for inhibiting undesired cyclin-dependent kinase 2 activity in a cell comprising contacting the cell with a compound of Formula (I).

In one aspect, provided is a method for treating cancer in a patient, in which the cancer is characterized by undesired cyclin-dependent kinase 2 activity, comprising administering to the patient an amount of a compound of Formula (I) effective for inhibiting the undesired cyclin-dependent kinase 2 activity. In some embodiments, the cancer is selected from breast cancer and cervical cancer.

In one aspect, described herein is a pharmaceutical composition comprising a pharmaceutically acceptable diluent, excipient or binder, and a compound of Formula (I), or pharmaceutically acceptable salt, pharmaceutically acceptable prodrug, or pharmaceutically acceptable solvate thereof.

In one aspect, described herein is a pharmaceutical composition, which includes an effective amount of a compound provided herein, and a pharmaceutically acceptable excipient. In a further aspect, provided are compositions further including a second pharmaceutically active ingredient in addition to the compound of Formula (I).

In certain embodiments, provided herein is a pharmaceutical composition comprising: i) a physiologically acceptable carrier, diluent, and/or excipient; and ii) one or more compounds described herein.

In any of the aforementioned aspects are further embodiments that include single administrations of the effective amount of the compound of Formula (I), including further embodiments in which: (i) the compound of Formula (I) is administered once; (ii) the compound of Formula (I) is administered to the mammal multiple times over the span of one day; (iii) the compound of Formula (I) is administered continually; or (iv) the compound of Formula (I) is administered continuously.

In any of the aforementioned aspects are further embodiments that include multiple administrations of the effective amount of the compound of Formula (I), including further embodiments in which (i) the compound of Formula (I) is administered in a single dose; (ii) the time between multiple administrations is every 6 hours; (iii) the compound of Formula (I) is administered to the mammal every 8 hours. In further or alternative embodiments, the method comprises a drug holiday, wherein the administration of the compound of Formula (I) is temporarily suspended or the dose of the compound of Formula (I) being administered is temporarily reduced; at the end of the drug holiday, dosing of the compound of Formula (I) is resumed. The length of the drug holiday can vary from 2 days to 1 year.

In one aspect, compounds of Formula (I) described herein are administered to a human. In some embodiments, compounds of Formula (I) described herein are orally administered.

A further aspect relates to the use of a compound of Formula (I) in the manufacture of a medicament for treating a condition mediated by an enzyme selected from one or more CDK, aurora kinase, GSK, PLK, BCR-ABL, FLT, IKK, JAK, PDGF or VEGF and Src family enzymes. In another aspect is the use of a compound of Formula (I) in the manufacture of a medicament for treating a condition mediated by at least one enzyme selected from CDK1, CDK2, CDK4/6, CDK5, CDK7, CDK8, CDK9, CDK11, GSK-3, aurora kinase, PLK and a tyrosine kinase.

In another aspect, there is provided a method for treating a condition mediated by one or more enzymes selected from CDK, aurora kinase, GSK, PLK, BCR-ABL, FLT, IKK, JAK, PDGF or VEGF and Src family enzymes, particularly from one or more CDK1, CDK2, CDK4/6, CDK5, CDK7, CDK8, CDK9, CDK11, GSK-3, aurora kinase, PLK or tyrosine kinase enzyme, in a human or animal subject, the method comprising administering to a human or animal in need thereof a therapeutically effective amount of a compound of Formula (I).

In a further aspect, there is provided the use of a compound of Formula (I) in a method for treating a condition mediated by an enzyme selected from one or more CDK, aurora kinase, GSK, PLK, BCR-ABL, FLT, IKK, JAK, PDGF or VEGF and Src family enzymes, particularly from one or more CDK1, CDK2, CDK4/6, CDK5, CDK7, CDK8, CDK9, CDK11, GSK-3, aurora kinase, PLK or tyrosine kinase.

A further aspect relates to the use of a compound of Formula (I) or a pharmaceutically acceptable salt or solvate or physiologically hydrolysable, solubilising or immobilising derivative thereof, in an assay for identifying candidate compounds capable of treating a condition mediated by an enzyme selected from one or more CDK, aurora kinase, GSK, PLK, BCR-ABL, FLT, IKK, JAK, PDGF or VEGF and Src family enzymes, particularly from one or more CDK1, CDK2, CDK4/6, CDK5, CDK7, CDK8, CDK9, CDK11, GSK-3, aurora kinase, PLK or tyrosine kinase. In one aspect, provided is a method for treating or preventing inflammatory disorders by administrating to the patient an effective amount of a compound, or pharmaceutically acceptable salt, solvate, or prodrug thereof, the compound having the structure of Formula (I), preferably the compound having the structure of Formula (Ia), (Ib), or (Ic). The inflammatory disorder is selected from ARDS, SepticSepsis, or Rheumatoid Arthritic. In one aspect, provided is a method for inhibiting undesired cyclin-dependent kinase 9 activity in a cell comprising contacting the cell with a compound of Formula (I).

In one aspect, provided is a method for treating inflammatory disorder in a patient, in which the inflammatory disorder is characterized by undesired cyclin-dependent kinase 9 activity, comprising administering to the patient an amount of a compound of Formula (I) effective for inhibiting the undesired cyclin-dependent kinase 9 activity. In some embodiments, the inflammatory disorder is selected from ARDS, SepticSepsis, or Rheumatoid Arthritic.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Figure 1:
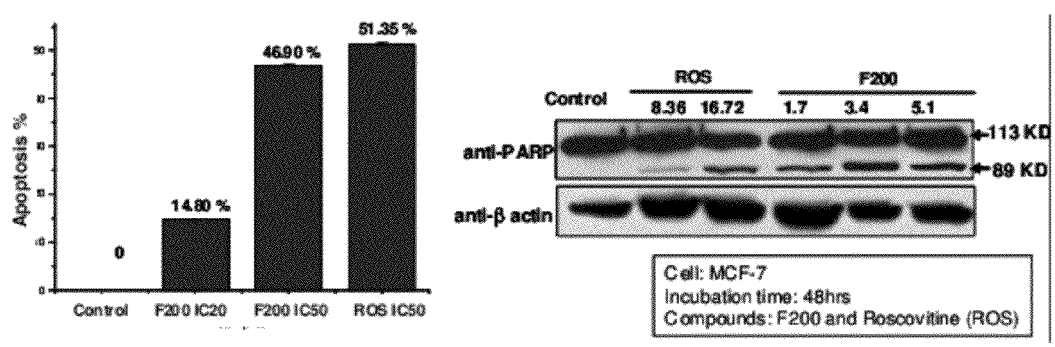
FIG. 1 showed that compound 18 induced cell apoptosis with dose-dependent manner.

The protein kinase family is one of the largest in the human genome, comprising 500 genes. The majority of kinases contain a 250-300 amino acid residue catalytic domain with a conserved core structure. This domain comprises a binding pocket for ATP, whose terminal phosphate group transfers covalently to its macromolecular substrates. The protein kinases may be categorized by the substrates they phosphorylate, e.g. protein-serine/threonine, protein-tyrosine.

Protein kinases mediate intracellular signalling by affecting a phosphoryl transfer from a nucleoside triphosphate to a protein acceptor that is involved in a signalling pathway. These phosphorylation events are triggered in response to a variety of extracellular and other stimuli and act as molecular on/off switches that can modulate or regulate the target protein biological function. An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Many diseases are associated with abnormal cellular responses triggered by protein kinase-mediated events. These diseases include, but are not limited to allergies, asthma, Alzheimer's disease, autoimmune diseases, bone diseases, cancer, cardiovascular diseases, inflammatory diseases, hormone-related diseases, metabolic diseases, neurological and neurodegenerative diseases. There is a need for protein kinase inhibitors that are effective as therapeutic agents.

Cyclin-dependent kinases (CDKs) are serine/threonine protein kinases that associate with various cyclin subunits, playing pivotal roles in the regulation of cell cycle progression and transcriptional cycle. Ten distinct CDKs (CDK1-9 and 11) are involved in a variety of important regulatory pathways in eukaryotic cells, including cell-cycle control, apoptosis, neuronal physiology, differentiation and transcription.

In one aspect, CDKs are classified into two major groups, reflecting their functions. The cell cycle regulator CDKs composed primarily of CDK1, CDK2, CDK3, CDK4 and CDK6 function with their cyclin partners including cyclin A, B, D1, D2, D3, E, and F to regulate promotion of the cell cycle. The transcription regulator CDKs, which include CDK7, CDK8, CDK9 and CDK11 work together with cyclin C, H, K, L1, L2, T1 and T2, tend to play roles in transcriptional regulation.

The CDKs are implicated in cell proliferation disorders, particularly in cancer. Cell proliferation is a result of the direct or indirect deregulation of the cell division cycle and the CDKs play a critical role in the regulation of the various phases of this cycle. Therefore, inhibitors of CDKs and their associated cyclins are useful targets for cancer therapy.

CDKs also play a role in apoptosis and T-cell development, which is predominantly due to the CDK functions in regulation of transcription.

Furthermore, numerous viruses require CDKs, particular CDK2, CDK7, and CDK9, for their replication process. CDK inhibitors have been reported to restrain viral replication including human immunodeficiency virus, human cytomegalovirus, herpes virus, and varicella-zoster virus.

Inhibition of CDK is also useful for the treatment of neurodegenerative disorders such as Alzheimer's disease. The appearance of Paired Helical Filaments, associated with Alzheimer's disease, is caused by the hyperphosphorylation of Tau protein by CDK5/p25.

Inhibition of one or more other serine/threonine kinases including the Aurora kinases, Glycogen synthesis kinases (GSKs), polo-like kinases (PLKs) and tyrosine kinases including Ableson tyrosine kinase (BCR-ABL), FMS-related tyrosine kinases (FLT), IkB kinases (IKK), Janus kinases (JAK), platelet-derived growth factor (PDGF) receptor tyrosine kinases, vascular endothelial growth factor (VEGF) receptor tyrosine kinases, and Src family are also useful for the treatment of numerous diseases, conditions or disorders mediated by these kinases.

GSK3 is known to phosphorylate many substrates and is thus involved in the regulation of multiple biochemical pathways. For example, GSK3 is over-expressed in muscle cells of type II diabetics and that an inverse correlation exists between skeletal muscle GSK3 activity and insulin action. GSK3 inhibition is therefore of therapeutic significance in the treatment of diabetes, particularly type II, and diabetic neuropathy.

Furthermore, GSK is highly expressed in the central and peripheral nervous systems. GSK3 inhibition is therefore of therapeutic significance in the treatment of CNS disorders such as Parkinsons and Alzheimers diseases.

Aurora kinases and PLK are also important therapeutic targets for treatment of proliferative disorders. Based on their known functions inhibition of Aurora kinases and PLKs activity should disrupt mitosis leading to cell cycle arrest and therefore slowing tumor growth and induce apoptosis.

Described herein are compounds that inhibit one or more protein kinases. In one aspect, the compounds described herein are heteroaryl-pyrimidine derivatives. More specifically, described herein are substituted 4-(indol-3-yl)-N-phenylpyrimidin-2-amine compounds, substituted 4-(pyrrolo[2,3-b]pyridin-3-yl)-N-phenylpyrimidin-2-amine compounds, 4-(pyrrolo[2,3-c]pyridin-3-yl)-N-phenylpyrimidin-2-amine compounds, substituted 4-(pyrrolo[3,2-b]pyridin-3-yl)-N-phenylpyrimidin-2-amine compounds, and substituted 4-(pyrrolo[3,2-c]pyridin-3-yl)-N-phenylpyrimidin-2-amine compounds. In one aspect, the compounds described herein have broad therapeutic use as protein kinase inhibitors.

Compounds

In one aspect, described herein is a compound of Formula (I), or pharmaceutically acceptable salt, solvate, or prodrug thereof:

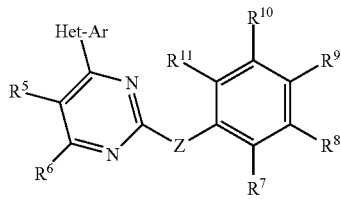

wherein,
Het-Ar is an unsubstituted or substituted indolyl ring, or an unsubstituted or substituted azaindolyl ring;
Z is —NR$^a$C(=O)—, —C(=O)NR$^a$—, —NR$^a$SO$_2$—, —SO$_2$NR$^a$—, —NR$^a$—, —CH$_2$NR$^a$—, —NR$^a$CH$_2$—, —CH$_2$—, —CH$_2$CH$_2$—, —CH=CH—, —CH$_2$C(=O)NR$^a$—, —NR$^a$C(=O)CH$_2$—, —SO$_2$—, or —SO—;
R$^a$ is H or alkyl;
R$^5$, R$^6$, R$^7$, R$^8$, R$^9$, R$^{10}$, and R$^{11}$, are each independently H, alkyl, alkyl-R$^{19}$, aryl, aryl-R$^{19}$, aralkyl, aralkyl-R$^{19}$, halogen, —NO$_2$, —CN, —OH, —O-alkyl, —COR$^{19}$, —COOR$^{19}$, —O-aryl, —O—R$^{19}$, —NH$_2$, —NH-alkyl, —NH-aryl, —N-(alkyl)$_2$, —N-(aryl)$_2$, —N-(alkyl)(aryl), —NH—R$^{19}$, —N—(R$^{19}$)(R$^{20}$), —N-(alkyl)(R$^{19}$), —N-(aryl)(R$^{19}$), —COOH, —CONH$_2$, —CONH-alkyl, —CONH-aryl, —CON-(alkyl)(R$^{19}$), —CON(aryl)(R$^{19}$), —CONH—R$^{19}$, —CON—(R$^{19}$)(R$^{20}$), —SO$_3$H, —SO$_2$-alkyl, —SO$_2$-alkyl-R$^{19}$, —SO$_2$-aryl, —SO$_2$-aryl-R$^{19}$, —SO$_2$NH$_2$, —SO$_2$NH—R$^{19}$, —SO$_2$N—(R$^{19}$)(R$^{20}$), —CF$_3$, —CO-alkyl, —CO-alkyl-R$^{19}$, —CO-aryl, —CO-aryl-R$^{19}$ or —R$^{21}$, wherein alkyl, aryl, aralkyl groups may be further substituted with one or more groups selected from halogen, —NO$_2$, —OH, —O-methyl, —NH$_2$, —COOH, —CONH$_2$ and —CF$_3$;
where R$^{19}$, R$^{20}$, and R$^{21}$ are physiologically hydrolysable group, solubilising group or immobilisable group.

In one aspect, R$^{19}$ and R$^{20}$ are each independently solubilising groups selected from:
(i) a mono-, di- or polyhydroxylated alicyclic group;
a di- or polyhydroxylated aliphatic or aromatic group;
a carbohydrate derivative;
an O- and/or S-containing heterocyclic group optionally substituted by one or more hydroxyl groups;
an aliphatic or aromatic group containing a carboxamide, sulfoxide, sulfone, or sulfonamide function; or
a halogenated alkylcarbonyl group;
(ii) COOH, SO$_3$H, OSO$_3$H, PO$_3$H$_2$, or OPO$_3$H$_2$;
(iii) Y, where Y is selected from an alicyclic, aromatic, or heterocyclic group comprising one or more of the functions =N—, —O—, —NH$_2$, —NH—, a quaternary amine salt, guanidine, and amidine, where Y is optionally substituted by one or more substituents selected from: SO$_2$-alkyl; alkyl optionally substituted by one or more OH groups; CO-alkyl; aralkyl; COO-alkyl; and an ether group optionally substituted by one or more OH groups; and
(iv) a natural or unnatural amino acid, a peptide or a peptide derivative;
each R$^{21}$ is a solubilising group as defined for R$^{19}$ and R$^{20}$ in (i) or (iv) above; or is selected from:
(v) OSO$_3$H, PO$_3$H$_2$, or OPO$_3$H$_2$;
(vi) Y as defined above, but excluding guanidine and quarternary amine salts;
(vii) NHCO(CH$_2$)$_m$[NHCO(CH$_2$)$_{m'}$]$_p$[NHCO(CH$_2$)$_{m''}$]$_q$Y or NHCO(CH$_2$)$_t$NH(CH$_2$)$_{t'}$Y where p and q are each 0 or 1, and m, m', m'', t and t' are each independently an integer from 1 to 10; and
(viii) (CH$_2$)$_n$NR$^{14}$COR$^{12}$, (CH$_2$)$_n$NR$^{15}$SO$_2$R$^{13}$, or SO$_2$R$^{16}$, where R$^{12}$, R$^{13}$ and R$^{16}$ are each alkyl groups optionally comprising one or more heteroatoms, and which are optionally substituted by one or more substituents selected from OH, NH$_2$, halogen and NO$_2$, R$^{14}$ and R$^{15}$ are each independently H or alkyl, and n and n' are each independently 0, 1, 2, or 3:
(ix) an ether or polyether optionally substituted by one or more hydroxyl groups or one or more Y groups;
(x) (CH$_2$)$_r$NH$_2$; where r is 0, 1, 2, or 3;
(xi) (CH$_2$)$_{r'}$OH; where r' is 0, 1, 2, or 3;
(xii) (CH$_2$)$_{n''}$NR$^{17}$COR$^{18}$ where R$^{17}$ is H or alkyl, n'' is 0, 1, 2 or 3 and R$^{18}$ is an aryl group optionally substituted by one or more substituents selected from halogen, NO$_2$, OH, alkoxy, NH$_2$, COOH, CONH$_2$ and CF$_3$;
(xiii) SO$_2$NR$^{22}$R$^{23}$ where R$^{22}$ and R$^{23}$ are each independently H, alkyl or aryl, with the proviso that at least one of R$^{22}$ and R$^{23}$ is other than H, or R$^{22}$ and R$^{23}$ are linked to form a cyclic group optionally containing one or more heteroatoms selected from N, O and S, and wherein said alkyl, aryl or cyclic group is optionally substituted by one or more substituents selected from halogen, NO$_2$, OH, alkoxy, NH$_2$, COOH, CONH$_2$ and CF$_3$.

In one aspect, at least one of R$^7$, R$^8$, R$^9$, R$^{10}$, and R$^{11}$ is selected from (CH$_2$)$_{n''}$NR$^{17}$COR$^{18}$, (CH$_2$)$_{n''}$C(=O)NR$^{17}$R$^{18}$ and SO$_2$NR$^{22}$R$^{23}$.

In one aspect, Het-Ar is a substituted or unsubstituted group selected from indol-3-yl, pyrrolo[2,3-b]pyridin-3-yl, pyrrolo[2,3-c]pyridin-3-yl, pyrrolo[3,2-b]pyridin-3-yl, and pyrrolo[3,2-c]pyridin-3-yl.

In one aspect, Het-Ar is a substituted or unsubstituted group selected from 1-(alkyl)-indol-3-yl, 1-(alkyl)-pyrrolo[2,3-b]pyridin-3-yl, 1-(alkyl)-pyrrolo[2,3-c]pyridin-3-yl, 1-(alkyl)-pyrrolo[3,2-b]pyridin-3-yl, and 1-(alkyl)-pyrrolo[3,2-c]pyridin-3-yl.

In one aspect, the compound of Formula (I) has the structure:

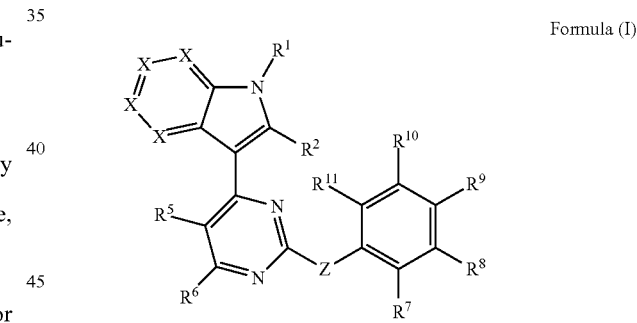

Formula (I)

wherein each X is —C(R$^3$)— or —N—, provided that at least two X are —C(R$^3$)—;
Z is —NR$^a$C(=O)—, —C(=O)NR$^a$—, —NR$^a$SO$_2$—, —SO$_2$NR$^a$—, —NR$^a$—, —CH$_2$NR$^a$—, —NR$^a$CH$_2$—, —CH$_2$—, —CH$_2$CH$_2$—, —CH=CH—, —CH$_2$C(=O)NR$^a$—, —NR$^a$C(=O)CH$_2$—, —SO$_2$—, or —SO—;
R$^a$ is H or alkyl;
and wherein R$^1$, R$^2$, R$^3$, R$^5$, R$^6$, R$^7$, R$^8$, R$^9$, R$^{10}$, and R$^{11}$, are each independently H, alkyl, alkyl-R$^{19}$, aryl, aryl-R$^{19}$, aralkyl, aralkyl-R$^{19}$, halogen, —NO$_2$, —CN, —OH, —O-alkyl, —COR$^{19}$, —COOR$^{19}$, —O-aryl, —O—R$^{19}$, —NH$_2$, —NH-alkyl, —NH-aryl, —N-(alkyl)$_2$, —N-(aryl)$_2$, —N-(alkyl)(aryl), —NH—R$^{19}$, —N—(R$^{19}$)(R$^{20}$), —N-(alkyl)(R$^{19}$), —N-(aryl)(R$^{19}$), —COOH, —CONH$_2$, —CONH-alkyl, —CONH-aryl, —CON-(alkyl)(R$^{19}$), —CON(aryl)(R$^{19}$), —CONH—R$^{19}$, —CON—(R$^{19}$)(R$^{20}$), —SO$_3$H, —SO$_2$-alkyl, —SO$_2$-alkyl-R$^{19}$, —SO$_2$-aryl, —SO$_2$-aryl-R$^{19}$, —SO$_2$NH$_2$, —SO$_2$NH—R$^{19}$, —SO$_2$N—(R$^{19}$)(R$^{20}$), —CF$_3$, —CO-alkyl, —CO-alkyl-R$^{19}$, —CO-aryl, —CO-aryl-R$^{19}$ or —R$^{21}$, wherein alkyl, aryl, aralkyl groups may be further substituted with one or more groups selected from halogen, —NO₂, —OH, —O-methyl, —NH₂, —COOH, —CONH₂ and —CF₃;
where $R^{19}$, $R^{20}$, and $R^{21}$ are physiologically hydrolysable group, solubilising group or immobilisable group.

In one aspect, $R^1$, $R^2$, $R^3$, $R^5$, $R^6$, $R^7$, $R^8$, $R^9$, $R^{10}$, and $R^{11}$, are each independently H, alkyl, aryl, aralkyl, halogen, —NO₂, —CN, —OH, —O-alkyl, —O-aryl, —NH₂, —NH-alkyl, —NH-aryl, —N-(alkyl)₂, —N-(aryl)₂, —N-(alkyl)(aryl), —COOH, —CONH₂, —CONH-alkyl, —CONH-aryl, —SO₃H, —SO₂-alkyl, —SO₂-aryl, —SO₂NH₂, —CF₃, —CO-alkyl, —CO-aryl, wherein alkyl, aryl, aralkyl groups may be further substituted with one or more groups selected from halogen, —NO₂, —OH, —O-methyl, —NH₂, —COOH, —CONH₂ and —CF₃.

In one aspect, $R^5$ and $R^6$ are each H.

In one aspect, $R^2$ is H or alkyl. In another aspect, $R^2$ is H.

In one aspect, at least one $R^3$ is H. In another aspect, at least two $R^3$ are H.

In one aspect, at least one of $R^7$, $R^8$, $R^9$, $R^{10}$, and $R^{11}$ is H. In another aspect, at least two of $R^7$, $R^8$, $R^9$, $R^{10}$, and $R^{11}$ are H.

In one aspect, the compound of Formula (I) has the structure:

Formula (I)

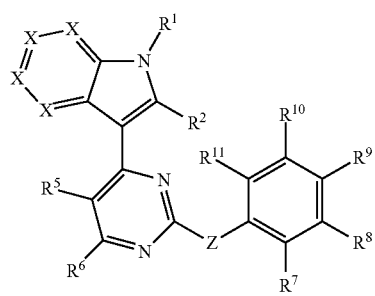

wherein each X is —C(R³)— or —N—, provided that at least two X are —C(R³)—;
Z is —NRᵃC(=O)—, —C(=O)NRᵃ—, —NRᵃSO₂—, —SO₂NRᵃ—, —NRᵃ—, —CH₂NRᵃ—, —NRᵃCH₂—, —CH₂—, —CH₂CH₂—, —CH=CH—, —CH₂C(=O)NRᵃ—, —NRᵃC(=O)CH₂—, —SO₂—, or —SO—;
$R^a$ is H or alkyl; and wherein $R^1$, $R^2$, $R^3$, $R^5$, $R^6$, $R^7$, $R^8$, $R^9$, $R^{10}$, and $R^{11}$, are as described herein.

In one aspect, the compound of Formula (I) has the structure of Formula (Ia):

Formula (Ia)

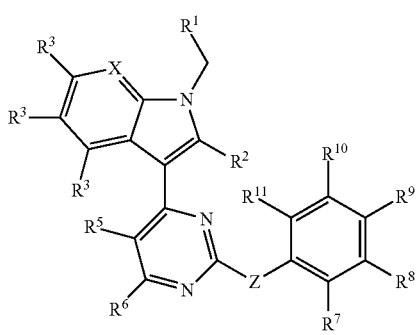

wherein X is —C(R³)— or —N—;
Z is —NRᵃC(=O)—, —C(=O)NRᵃ—, —NRᵃSO₂—, —SO₂NRᵃ—, —NRᵃ—, —CH₂NRᵃ—, —NRᵃCH₂—, —CH₂—, —CH₂CH₂—, —CH=CH—, —CH₂C(=O)NRᵃ—, —NRᵃC(=O)CH₂—, —SO₂—, or —SO—;
$R^a$ is H or alkyl; and wherein $R^1$, $R^2$, $R^3$, $R^5$, $R^6$, $R^7$, $R^8$, $R^9$, $R^{10}$, and $R^{11}$, are as described herein.

In another aspect, the compound of Formula (I) has the structure of Formula (Ib):

Formula (Ib)

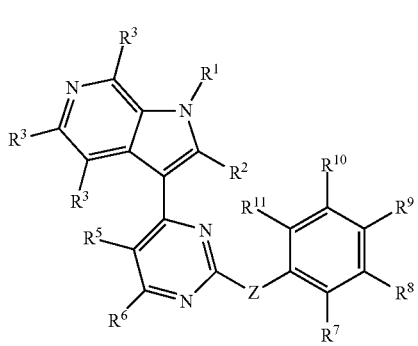

wherein
Z is —NRᵃC(=O)—, —C(=O)NRᵃ—, —NRᵃSO₂—, —SO₂NRᵃ—, —NRᵃ—, —CH₂NRᵃ—, —NRᵃCH₂—, —CH₂—, —CH₂CH₂—, —CH=CH—, —CH₂C(=O)NRᵃ—, —NRᵃC(=O)CH₂—, —SO₂—, or —SO—;
$R^a$ is H or alkyl; and wherein $R^1$, $R^2$, $R^3$, $R^5$, $R^6$, $R^7$, $R^8$, $R^9$, $R^{10}$, and $R^{11}$, are as described herein.

In one aspect, the compound of Formula (I) has the structure of Formula (Ic)

Formula (Ic)

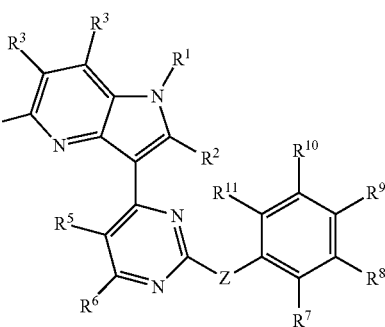

wherein
Z is —NRᵃC(=O)—, —C(=O)NRᵃ—, —NRᵃSO₂—, —SO₂NRᵃ—, —NRᵃ—, —CH₂NRᵃ—, —NRᵃCH₂—, —CH₂—, —CH₂CH₂—, —CH=CH—, —CH₂C(=O)NRᵃ—, —NRᵃC(=O)CH₂—, —SO₂—, or —SO—;
$R^a$ is H or alkyl; and wherein $R^1$, $R^2$, $R^3$, $R^5$, $R^6$, $R^7$, $R^8$, $R^9$, $R^{10}$, and $R^{11}$, are as described herein.

In one aspect, the compound of Formula (I) has the structure of Formula (Id)

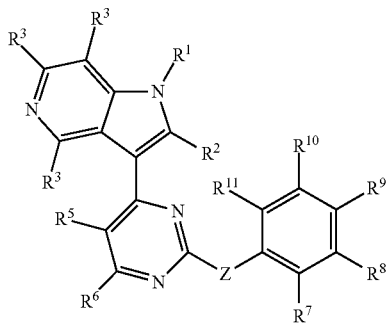

Formula (Id)

wherein
Z is —NR$^a$C(=O)—, —C(=O)NR$^a$—, —NR$^a$SO$_2$—, —SO$_2$NR$^a$—, —NR$^a$—, —CH$_2$NR$^a$—, —NR$^a$CH$_2$—, —CH$_2$—, —CH$_2$CH$_2$—, —CH=CH—, —CH$_2$C(=O)NR$^a$—, —NR$^a$C(=O)CH$_2$—, —SO$_2$—, or —SO—;
R$^a$ is H or alkyl; and wherein R$^1$, R$^2$, R$^3$, R$^5$, R$^6$, R$^7$, R$^8$, R$^9$, R$^{10}$, and R$^{11}$, are as described herein.

In one aspect, Z is —NR$^a$C(=O)—, —C(=O)NR$^a$—, —NR$^a$SO$_2$—, —SO$_2$NR$^a$—, —NR$^a$—, —CH$_2$NR$^a$—, —NR$^a$CH$_2$—, —CH$_2$—, —CH$_2$CH$_2$—, —CH=CH—, —CH$_2$C(=O)NR$^a$—, —NR$^a$C(=O)CH$_2$—, —SO$_2$—, or —SO—; R$^a$ is H or alkyl.

In one aspect, —Z— is —NH—, —NHC(=O)—, —NHSO$_2$—, —NHCH$_2$—, —CH$_2$—, —CH$_2$CH$_2$—, —CH=CH—, —CH$_2$C(=O)NH—, —SO$_2$—, or —SO—.

In one aspect, R$^a$ is H.

In one aspect, Z is —NR$^a$—. In one aspect, Z is —NH—.

In one aspect, R$^{19}$ and R$^{20}$ are each independently solubilising groups selected from a mono-, di- or polyhydroxylated alicyclic group; a di- or polyhydroxylated aliphatic or aromatic group; a carbohydrate derivative; an O- and/or S-containing heterocyclic group optionally substituted by one or more hydroxyl groups; an aliphatic or aromatic group containing a carboxamide, sulfoxide, sulfone, or sulfonamide function; or a halogenated alkylcarbonyl group; COOH, SO$_3$H, OSO$_3$H, PO$_3$H$_2$, or OPO$_3$H$_2$.

In one aspect, at least one of R$^{19}$ or R$^{20}$ comprises an ionisable basic group selected from an alicyclic, aromatic, or heterocyclic group comprising one or more of the functions =N—, —O—, —NH$_2$, —NH—, a quarternary amine salt, guanidine, amidine, optionally substituted by one or more substituents selected from: SO$_2$-alkyl; alkyl optionally substituted by one or more OH groups; CO-alkyl; aralkyl; COO-alkyl; and an ether group optionally substituted by one or more OH groups.

In one aspect, at least one of R$^{19}$ and R$^{20}$ is a natural or unnatural amino acid residues and peptides, or their derivatives.

In one aspect, R$^{19}$ or R$^{20}$ is selected from:
OSO$_3$H, PO$_3$H$_2$, or OPO$_3$H$_2$;
Y, where Y is selected from an alicyclic, aromatic, or heterocyclic group comprising one or more of the functions =N—, —O—, —NH$_2$, —NH—, a quarternary amine salt, guanidine, and amidine, where Y is optionally substituted by one or more substituents selected from: SO$_2$-alkyl; alkyl optionally substituted by one or more OH groups; CO-alkyl; aralkyl; COO-alkyl; and an ether group optionally substituted by one or more OH groups.

In one aspect, each R$^{21}$ is a solubilising group as defined for R$^{19}$ and R$^{20}$ hereinbefore defined; or is selected from: OSO$_3$H, PO$_3$H$_2$, or OPO$_3$H$_2$; Y as defined above, but excluding guanidine and quarternary amine salts; NHCO(CH$_2$)$_m$[NHCO(CH$_2$)$_{m'}$]$_p$[NHCO(CH$_2$)$_{m''}$]$_q$Y or NHCO(CH$_2$)$_t$NH(CH$_2$)$_{t'}$Y where p and q are each 0 or 1, and m, m', m'', t and t' are each independently an integer from 1 to 10; and (CH$_2$)$_1$NR$^{14}$COR$^{12}$, (CH$_2$)$_n$NR$^{15}$SO$_2$R$^{13}$, or SO$_2$R$^{16}$, where R$^{12}$, R$^{13}$ and R$^{16}$ are each alkyl groups optionally comprising one or more heteroatoms, and which are optionally substituted by one or more substituents selected from OH, NH$_2$, halogen and NO$_2$, R$^{14}$ and R$^{15}$ are each independently H or alkyl, and n and n' are each independently 0, 1, 2, or 3; an ether or polyether optionally substituted by one or more hydroxyl groups or one or more Y groups; (CH$_2$)$_r$NH$_2$; where r is 0, 1, 2, or 3; (CH$_2$)$_{r'}$OH; where r' is 0, 1, 2, or 3; (CH$_2$)$_{n''}$NR$^{17}$COR$^{18}$ where R$^{17}$ is H or alkyl, n'' is 0, 1, 2 or 3 and R$^{18}$ is an aryl group optionally substituted by one or more substituents selected from halogen, NO$_2$, OH, alkoxy, NH$_2$, COOH, CONH$_2$ and CF$_3$; SO$_2$NR$^{22}$R$^{23}$ where R$^{22}$ and R$^{23}$ are each independently H, alkyl or aryl, with the proviso that at least one of R$^{22}$ and R$^{23}$ is other than H, or R$^{22}$ and R$^{23}$ are linked to form a cyclic group optionally containing one or more heteroatoms selected from N, O and S, and wherein said alkyl, aryl or cyclic group is optionally substituted by one or more substituents selected from halogen, NO$_2$, OH, alkoxy, NH$_2$, COOH, CONH$_2$ and CF$_3$.

In one aspect, R$^7$, R$^8$, R$^9$, R$^{10}$ and R$^{11}$ are each independently H, alkyl, alkyl-R$^{19}$, aryl, aryl-R$^{19}$, aralkyl, aralkyl-R$^{19}$, halogen, —NO$_2$, —CN, —OH, —O-alkyl, —COR$^{19}$, —COOR$^{19}$, —O-aryl, —O—R$^{19}$, —NH$_2$, NH-alkyl, NH-aryl, N-(alkyl)$_2$, N-(aryl)$_2$, —N-(alkyl)(aryl), NH—R$^{19}$, N—(R$^{19}$)(R$^{20}$), N-(alkyl)(R$^{19}$), —N-(aryl)(R$^{19}$), —COOH, —CONH$_2$, —CONH-alkyl, —CONH-aryl, —CON-(alkyl)(R$^{19}$), —CON(aryl)(R$^{19}$), —CONH—R$^{19}$, —CON—(R$^{19}$)(R$^{20}$), —SO$_3$H, —SO$_2$-alkyl, —SO$_2$-alkyl-R$^{19}$, —SO$_2$-aryl, —SO$_2$-aryl-R$^{19}$, —SO$_2$NH$_2$, —SO$_2$NH—R$^{19}$, —SO$_2$N—(R$^{19}$)(R$^{20}$), —CF$_3$, —CO-alkyl, —CO-alkyl-R$^{19}$, —CO-aryl, —CO-aryl-R$^{19}$ or R$^{21}$, wherein alkyl, aryl, aralkyl groups may be further substituted with one or more groups selected from halogen, —NO$_2$, —OH, —O-methyl, —NH$_2$, —COOH, —CONH$_2$ and —CF$_3$.

In another embodiment, at least one of R$^1$, R$^2$, R$^3$, R$^5$, R$^6$, R$^7$, R$^8$, R$^9$, R$^{10}$ and R$^{11}$ is R$^{21}$.

In one aspect, R$^1$ is selected from H, alkyl, aryl, heteroaryl, cycloalkyl, alkyl-aryl, alkyl-heteroaryl and alkyl-cycloalkyl.

In one aspect, R$^1$ is selected from H, C$_1$-C$_5$-alkyl, aryl, heteroaryl, cycloalkyl, alkyl-aryl, alkyl-heteroaryl and alkyl-cycloalkyl.

In one aspect, R$^2$ is selected from H, alkyl, C$_1$-C$_5$ alkyl, CONH$_2$, CONH-alkyl, CN, CF$_3$, O-alkyl, halogen, NH$_2$, NH-alkyl, NHCO-alkyl, alkyl-heteroaryl, and alkyl-cycloalkyl.

In one aspect, R$^2$ is selected from H, C$_1$-C$_5$ alkyl, CONH$_2$, CONH-alkyl, CN, CF$_3$, O-alkyl, halogen, NH$_2$, NH-alkyl, NHCO-alkyl, alkyl-heteroaryl, and alkyl-cycloalkyl.

In one aspect, each R$^3$ is independently selected from H, alkyl, CONH$_2$, CONH-alkyl, CN, OH, CF$_3$, O-alkyl, halogen, NH$_2$, NH-alkyl, NHCO-alkyl, alkyl-heteroaryl, alkyl-cycloalkyl.

In one embodiment, R$^7$ is H, O-alkyl, CF$_3$, alkyl or halogen.

In one embodiment, R$^7$ is selected from H, OCH$_3$, CF$_3$, alkyl or halogen.

In one embodiment, R$^8$ and R$^{10}$ are independently selected from H, CONH$_2$, CONH-alkyl, CN, OH, CF$_3$, sulphonyl, carbonyl, amide or sulphonamide, or thioether link to an unsubstituted or substituted 6 membered cyclic or heterocyclic, or aromatic or heteroaromatic ring, wherein substituents are as hereinbefore defined.

In one aspect, $R^8$ and $R^{10}$ are independently selected from $SO_2$—$NR^{20}$, $SO_2$-cycloheteroalkyl, $SO_2$-cycloalkyl, $SO_2$-heteroaryl, SO-cycloheteroalkyl, SO-cycloalkyl, SO-heteroaryl, C(=O)-cycloheteroalkyl, C(=O)-cycloalkyl, C(=O)-heteroaryl, N-(alkyl)(cycloalkyl), N-(alkyl)(cycloheteroalkyl), or N-(alkyl)(heteroaryl) more preferably wherein the cycloheteroalkyl is heteroatom linked and may be unsubstituted or substituted comprising one, two or three heteroatoms selected from N, O, S. More preferably a cycloheteroalkyl is a N-alkyl-morpholino, N-alkyl-piperazine or N-alkyl-piperadine. Most preferably $R^5$ and $R^7$ are independently selected from N-linked N-(alkyl)(cycloheteroalkyl), $SO_2$-cycloheteroalkyl and CO-cycloheteroalkyl most preferably such as N-(alkyl)(morpholino), N-(alkyl)(piperazine), N-(alkyl)(piperadine), $SO_2$-piperazines, $SO_2$-morpholines, —C(=O)-piperazines, —C(=O)-morpholines, —C(=O)-piperadine or the like.

In one aspect, $R^9$ is selected from H, alkyl, for example $C_{1-5}$ alkyl, $CONH_2$, CONH-alkyl, CN, OH, $CF_3$, O-alkyl, halogen, $NH_2$, NH-alkyl, NHCO-alkyl, sulphonyl, carbonyl, amide or sulphonamide, or thioether link to an unsubstituted or substituted 6 membered cyclic or heterocyclic, or aromatic or heteroaromatic ring, wherein substituents are as hereinbefore defined.

In one aspect, $R^{11}$ is selected from H, halogen, O-alkyl. In one aspect, $R^{11}$ is selected from H, halogen and O—$C_1$-$C_5$ alkyl.

In one aspect, up to six of $R^1$, $R^2$, $R^3$, $R^5$, $R^6$, $R^7$, $R^8$, $R^9$, $R^{10}$, and $R^{11}$, for example one, two, three or four thereof, shall correspond to or contain one or more of the group $R^{19}$ or $R^{20}$. Preferably either or all of $R^8$, $R^9$ or $R^{10}$ comprise or contain one or more of the group $R^{20}$ or $R^{21}$. Two or more groups $R^{19}$ and/or $R^{20}$ may be the same or different.

Preferably $R^1$, $R^2$, $R^3$, $R^8$ or $R^9$ comprises or contains a solubilising moiety $R^{19}$ or $R^{20}$.

In one aspect, described herein are compounds of Formula (Ia) wherein: X is $CR^3$ or N; Z is NH;
$R^1$ and $R^2$ are selected from H, alkyl, such as $C_{1-5}$-alkyl or aryl, such as $C_6$ aryl; halogen, or heteroaryl;
$R^3$ is one, two or three groups independently selected from H, amino, $C_{1-4}$ alkyl, CN, $CF_3$, halogen, $NO_2$ O-alkyl, $NH_2$, NH-alkyl, $N(alkyl)_2$, $CO_2$alkyl, CO-alkyl, $CONH_2$, CONH-alkyl or heteroaryl or is contained with $R^{20}$ or $R^{21}$;
$R^7$ is H, OMe, alkyl, or halogen,
each $R^8$, $R^9$ or $R^{10}$ is independently H, alkyl, OH $CF_3$, O-alkyl, halogen, O-heteroaryl, alkyl-heteroaryl, alkyl-cycloalkyl which may be part unsaturated; $NH_2SO_2$—$NH_2$, $SO_2$—$NR^{20}$, $SO_2$-cycloheteroalkyl, SO-cycloheteroalkyl, $SO_2$-heteroaryl, SO-heteroaryl, CO-cycloheteroalkyl or CO-heteroarylalkyl, and the solubilising moiety corresponds to or is contained within $R^1$, $R^2$, $R^3$, or $R^7$; and wherein $R^{11}$ is H and the solubilising moiety corresponds to or is contained within $R^1$, $R^2$, $R^3$ or $R^7$.

In another embodiment, described herein are compounds of Formula (Ib) wherein: Z is NH;
$R^1$ and $R^2$ are selected from H, alkyl, such as $C_{1-5}$-alkyl or aryl, such as $C_6$ aryl; halogen, or heteroaryl;
$R^3$ is one, two or three groups independently selected from H, amino, $C_{1-4}$ alkyl, CN, $CF_3$, halogen, $NO_2$ O-alkyl, $NH_2$, NH-alkyl, $N(alkyl)_2$, $CO_2$alkyl, CO-alkyl, $CONH_2$, CONH-alkyl or heteroaryl or is contained with $R^{20}$ or $R^{21}$;
$R^7$ is H, OMe, alkyl, or halogen,
each $R^8$, $R^9$ or $R^{10}$ is independently alkyl, OH, $CF_3$, O-alkyl, halogen, O-heteroaryl, alkyl-heteroaryl, alkyl-cycloalkyl which may be part unsaturated; $NH_2$ $SO_2$—$NH_2$, $SO_2$—$NR^{20}$, $SO_2$-cycloheteroalkyl, SO-cycloheteroalkyl, $SO_2$-heteroaryl, SO-heteroaryl, CO-cycloheteroalkyl or CO-heteroarylalkyl, and the solubilising moiety corresponds to or is contained within $R^1$, $R^2$, $R^3$ or $R^7$; and wherein $R^{11}$ is H and the solubilising moiety corresponds to or is contained within $R^1$, $R^2$, $R^3$ or $R^7$.

In another embodiment, described herein are compounds of Formula (Ic) wherein:
Z is NH;
$R^1$ and $R^2$ are selected from H, alkyl, such as $C_{1-5}$-alkyl or aryl, such as $C_6$ aryl, halogen, or heteroaryl;
$R^3$ is one or more groups selected from H, amino, $C_{1-4}$ alkyl, CN, $CF_3$, halogen, $NO_2$ O-alkyl, $NH_2$, NH-alkyl, $N(alkyl)_2$, $CO_2$alkyl, CO-alkyl, $CONH_2$, CONH-alkyl or heteroaryl or is contained with $R^{10}$ or $R^{11}$;
$R^7$ is H, OMe, alkyl, or halogen,
each $R^8$, $R^9$ or $R^{10}$ is independently alkyl, OH, $CF_3$, O-alkyl, halogen, O-heteroaryl, alkyl-heteroaryl, alkyl-cycloalkyl which may be part unsaturated; $NH_2$ $SO_2$—$NH_2$, $SO_2$—$NR^{20}$, $SO_2$-cycloheteroalkyl, SO-cycloheteroalkyl, $SO_2$-heteroaryl, SO-heteroaryl, CO-cycloheteroalkyl or CO-heteroaryl alkyl, and the solubilising moiety corresponds to or is contained within $R^1$, $R^2$, $R^3$ or $R^7$; and wherein $R^{11}$ is H and the solubilising moiety corresponds to or is contained within $R^1$, $R^2$, $R^3$ or $R^7$.

In a further aspect of the invention there is provided a compound of formula I as hereinbefore defined wherein one or more $R^{19}$ or $R^{20}$ alternatively or additionally comprise devices for immobilization thereof. Such devices may be chemical functions that can be used for covalent attachment to solid phases such as functionalized polymers (e.g. agarose, polyacrylamide, polystyrene etc.) as commonly found in matrices (microtitre plate wells, microbeads, membranes, etc.) used for biochemical assays and affinity chromatography. Alternatively, the devices may be small molecules (e.g. biotin) or polypeptides (e.g. antigens), which can be used for non-covalent immobilization through binding to an immobilized receptor (e.g. avidin or streptavidin in the case of biotin, or a specific antibody in the case of antigens).

In a further aspect of the invention there is provided a precursor to a compound of formula I as hereinbefore defined wherein one or more $R^{19}$ or $R^{20}$ is a solubilising moiety comprising a natural or unnatural amino acid residue, peptide or derivative as hereinbefore defined.

In one aspect, $R^1$, $R^2$, $R^3$, $R^5$, $R^6$, $R^7$, $R^8$, $R^9$, $R^{10}$ and $R^{11}$ are each independently selected from the group consisting of H, halogen, —$NH_2$, —$NO_2$, —CN, —OH, —$CO_2H$, —$CONH_2$, —$SO_3H$, —$SO_2NH_2$, —$SO_2CH_3$, —$OCH_3$, —$CF_3$, —$CH_3$, and -$L^A$-$L^B$-$R^{32}$; $L^A$ is a covalent bond or an alkyl group; $L^B$ is a covalent bond, —O—, —$NR^{32}$—, —NH—, —C(=O)—, —C(=O)O—, —OC(=O)—, —C(=O)$NR^{32}$—, —C(=O)NH—, —$NR^{32}$C(=O)—, —NHC(=O)—, —$SO_2$—, —$SO_2NR^{32}$—, —$NR^{32}SO_2$—, —$SO_2NH$—, or —$NHSO_2$—; $R^{32}$ is H, substituted or unsubstituted alkyl, haloalkyl, substituted or unsubstituted aryl, substituted or unsubstituted heteroaryl, substituted or unsubstituted non-aromatic heterocycle, or substituted or unsubstituted cycloalkyl; wherein any $R^{32}$ group, when substituted, is substituted with one or more groups selected from halogen, —$NH_2$, —$NO_2$, —CN, —OH, —$CO_2H$, —$CONH_2$, —$SO_3H$, —$SO_2NH_2$, —$SO_2CH_3$, —$OCH_3$, and —$CF_3$.

In one aspect, described herein is a compound, or pharmaceutically acceptable salt, solvate, or prodrug thereof, having the structure of Formula (Ia):

Formula (Ia)

wherein:
X is —C(R³)— or —N—;
R¹ is unsubstituted $C_1$-$C_6$ alkyl, unsubstituted or substituted aryl, or unsubstituted or substituted heteroaryl;
R², R³, R⁵, R⁶, R⁷, R⁸, R⁹, R¹⁰ and R¹¹ are each independently selected from the group consisting of H, halogen, —NH₂, —NO₂, —CN, —OH, —CO₂H, —CONH₂, —SO₃H, —SO₂NH₂, —SO₂CH₃, —OCH₃, —CF₃, —CH₃, and -$L^A$-$L^B$-$R^{32}$;
$L^A$ is a covalent bond or an alkyl group;
$L^B$ is a covalent bond, —O—, —NR³²—, —NH—, —C(=O)—, —C(=O)O—, —OC(=O)—, —C(=O)NR³²—, —C(=O)NH—, —NR³²C(=O)—, —NHC(=O)—, —SO₂—, —SO₂NR³²—, —NR³²SO₂—, —SO₂NH—, or —NHSO₂—;
R³² is H, substituted or unsubstituted alkyl, haloalkyl, substituted or unsubstituted aryl, substituted or unsubstituted heteroaryl, substituted or unsubstituted non-aromatic heterocycle, or substituted or unsubstituted cycloalkyl;
wherein any R³² group, when substituted, is substituted with one or more groups selected from halogen, —NH₂, —NO₂, —CN, —OH, —CO₂H, —CONH₂, —SO₃H, —SO₂NH₂, —SO₂CH₃, —OCH₃, and —CF₃;
Z is —NR^aC(=O)—, —C(=O)NR^a—, —NR^aSO₂—, —SO₂NR^a—, —NR^a—, —CH₂NR^a—, —NR^aCH₂—, —CH₂—, —CH₂CH₂—, —CH=CH—, —CH₂C(=O)NR^a—, —NR^aC(=O)CH₂—, —SO₂—, or —SO—;
R^a is H or alkyl.

In one aspect, X is N. In another aspect, X is —C(R³)—.
In some embodiments, Z is —NR^a—.
In some embodiments, R¹ is unsubstituted $C_1$-$C_6$ alkyl or unsubstituted or substituted phenyl.
In some embodiments, each R³ is independently selected from the group consisting of H, halogen, —NH₂, —NO₂, —CN, —OH, —CO₂H, —CONH₂, —SO₃H, —SO₂NH₂, —SO₂CH₃, —OCH₃, —CF₃, and —CH₃.
In some embodiments, R², R⁵ and R⁶ are each H.
In other embodiments, R⁷, R⁸, R⁹, R¹⁰ and R¹¹ are each independently selected from the group consisting of H, halogen, —NH₂, —NO₂, —CN, —OH, —CO₂H, —CONH₂, —SO₃H, —SO₂NH₂, —SO₂CH₃, —OCH₃, —CF₃, —CH₃, and -$L^A$-$L^B$-$R^{32}$; $L^A$ is a covalent bond or an alkyl group; $L^B$ is a covalent bond, —O—, —NR³²—, —NH—, —C(=O)O—, —C(=O)NR³²—, —C(=O)NH—, —SO₂NR³²—, or —SO₂NH—; R³² is H, substituted or unsubstituted alkyl, haloalkyl, substituted or unsubstituted aryl, substituted or unsubstituted heteroaryl, substituted or unsubstituted non-aromatic heterocycle, or substituted or unsubstituted cycloalkyl; wherein any R³² group, when substituted, is substituted with one or more groups selected from halogen, —NH₂, —NO₂, —CN, —OH, —CO₂H, —CONH₂, —SO₃H, —SO₂NH₂, —SO₂CH₃, —OCH₃, and —CF₃.

In one aspect, provided herein is a compound, or pharmaceutically acceptable salt, solvate, or prodrug thereof, having the structure of Formula (Ib):

Formula (Ib)

wherein:
R¹, R², R³, R⁵, R⁶, R⁷, R⁸, R⁹, R¹⁰ and R¹¹ are each independently selected from the group consisting of H, halogen, —NH₂, —NO₂, —CN, —OH, —CO₂H, —CONH₂, —SO₃H, —SO₂NH₂, —SO₂CH₃, —OCH₃, —CF₃, —CH₃, and -$L^A$-$L^B$-$R^{32}$;
$L^A$ is a covalent bond or an alkyl group;
$L^B$ is a covalent bond, —O—, —NR³²—, —NH—, —C(=O)—, —C(=O)O—, —OC(=O)—, —C(=O)NR³²—, —C(=O)NH—, —NR³²C(=O)—, —NHC(=O)—, —SO₂—, —SO₂NR³²—, —NR³²SO₂—, —SO₂NH—, or —NHSO₂—;
R³² is H, substituted or unsubstituted alkyl, haloalkyl, substituted or unsubstituted aryl, substituted or unsubstituted heteroaryl, substituted or unsubstituted non-aromatic heterocycle, or substituted or unsubstituted cycloalkyl;
wherein any R³² group, when substituted, is substituted with one or more groups selected from halogen, —NH₂, —NO₂, —CN, —OH, —CO₂H, —CONH₂, —SO₃H, —SO₂NH₂, —SO₂CH₃, —OCH₃, and —CF₃;
Z is —NR^aC(=O)—, —C(=O)NR^a—, —NR^aSO₂—, —SO₂NR^a—, —NR^a—, —CH₂NR^a—, —NR^aCH₂—, —CH₂—, —CH₂CH₂—, —CH=CH—, —CH₂C(=O)NR^a—, —NR^aC(=O)CH₂—, —SO₂—, or —SO—;
R^a is H or alkyl.

In some embodiments, Z is —NR^a—.
In some embodiments, R¹ is unsubstituted $C_1$-$C_6$ alkyl.
In some embodiments, each R³ is independently selected from the group consisting of H, halogen, —NH₂, —NO₂, —CN, —OH, —CO₂H, —CONH₂, —SO₃H, —SO₂NH₂, —SO₂CH₃, —OCH₃, —CF₃, and —CH₃.
In other embodiments, R², R⁵ and R⁶ are each H.
In some embodiments, R⁷, R⁸, R⁹, R¹⁰ and R¹¹ are each independently selected from the group consisting of H, halogen, —NH₂, —NO₂, —CN, —OH, —CO₂H, —CONH₂, —SO₃H, —SO₂NH₂, —SO₂CH₃, —OCH₃, —CF₃, —CH₃, and -$L^A$-$L^B$-$R^{32}$; $L^A$ is a covalent bond or an alkyl group; $L^B$ is a covalent bond, —O—, —NR³²—, —NH—, —C(=O)O—, —C(=O)NR³²—, —C(=O)NH—, —SO₂NR³²—, or —SO₂NH—; R³² is H, substituted or unsubstituted alkyl, haloalkyl, substituted or unsubstituted aryl, substituted or unsubstituted heteroaryl, substituted or unsubstituted non-aromatic heterocycle, or substituted or unsubstituted cycloalkyl; wherein any $R^{32}$ group, when substituted, is substituted with one or more groups selected from halogen, —$NH_2$, —$NO_2$, —CN, —OH, —$CO_2H$, —$CONH_2$, —$SO_3H$, —$SO_2NH_2$, —$SO_2CH_3$, —$OCH_3$, and —$CF_3$.

In one aspect, provided herein is a compound, or pharmaceutically acceptable salt, solvate, or prodrug thereof, having the structure of Formula (Ic):

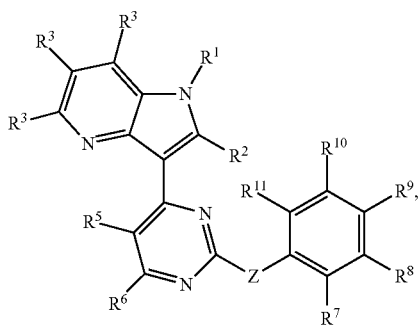

Formula (Ic)

wherein:
- $R^1$, $R^2$, $R^3$, $R^5$, $R^6$, $R^7$, $R^8$, $R^9$, $R^{10}$ and $R^{11}$ are each independently selected from the group consisting of H, halogen, —$NH_2$, —$NO_2$, —CN, —OH, —$CO_2H$, —$CONH_2$, —$SO_3H$, —$SO_2NH_2$, —$SO_2CH_3$, —$OCH_3$, —$CF_3$, —$CH_3$, and -$L^A$-$L^B$-$R^{32}$;
- $L^A$ is a covalent bond or an alkyl group;
- $L^B$ is a covalent bond, —O—, —$NR^{32}$—, —NH—, —C(=O)—, —C(=O)O—, —OC(=O)—, —C(=O)$NR^{32}$—, —C(=O)NH—, —$NR^{32}$C(=O)—, —NHC(=O)—, —$SO_2$—, —$SO_2NR^{32}$—, —$NR^{32}SO_2$—, —$SO_2NH$—, or —$NHSO_2$—;
- $R^{32}$ is H, substituted or unsubstituted alkyl, haloalkyl, substituted or unsubstituted aryl, substituted or unsubstituted heteroaryl, substituted or unsubstituted non-aromatic heterocycle, or substituted or unsubstituted cycloalkyl;
  - wherein any $R^{32}$ group, when substituted, is substituted with one or more groups selected from halogen, —$NH_2$, —$NO_2$, —CN, —OH, —$CO_2H$, —$CONH_2$, —$SO_3H$, —$SO_2NH_2$, —$SO_2CH_3$, —$OCH_3$, and —$CF_3$;
- Z is —$NR^aC(=O)$—, —$C(=O)NR^a$—, —$NR^aSO_2$—, —$SO_2NR^a$—, —$NR^a$—, —$CH_2NR^a$—, —$NR^aCH_2$—, —$CH_2$—, —$CH_2CH_2$—, —CH=CH—, —$CH_2C(=O)NR^a$—, —$NR^aC(=O)CH_2$—, —$SO_2$—, or —SO—;
- $R^a$ is H or alkyl.

In some embodiments. Z is —$NR^a$—.

In some embodiments, $R^1$ is unsubstituted $C_1$-$C_6$ alkyl.

In some embodiments, each $R^3$ is independently selected from the group consisting of H, halogen, —$NH_2$, —$NO_2$, —CN, —OH, —$CO_2H$, —$CONH_2$, —$SO_3H$, —$SO_2NH_2$, —$SO_2CH_3$, —$OCH_3$, —$CF_3$, and —$CH_3$.

In some embodiments, $R^2$, $R^5$ and $R^6$ are each H.

In some other embodiments, $R^2$, $R^8$, $R^9$, $R^{10}$ and $R^{11}$ are each independently selected from the group consisting of H, halogen, —$NH_2$, —$NO_2$, —CN, —OH, —$CO_2H$, —$CONH_2$, —$SO_3H$, —$SO_2NH_2$, —$SO_2CH_3$, —$OCH_3$, —$CF_3$, —$CH_3$, and -$L^A$-$L^B$-$R^{32}$, $L^A$ is a covalent bond or an alkyl group; $L^B$ is a covalent bond, —O—, —$NR^{32}$—, —NH—, —C(=O)O—, —C(=O)$NR^{32}$—, —C(=O)NH—, —$SO_2NR^{32}$—, or —$SO_2NH$—; $R^{32}$ is H, substituted or unsubstituted alkyl, haloalkyl, substituted or unsubstituted aryl, substituted or unsubstituted heteroaryl, substituted or unsubstituted non-aromatic heterocycle, or substituted or unsubstituted cycloalkyl; wherein any $R^{32}$ group, when substituted, is substituted with one or more groups selected from halogen, —$NH_2$, —$NO_2$, —CN, —OH, —$CO_2H$, —$CONH_2$, —$SO_3H$, —$SO_2NH_2$, —$SO_2CH_3$, —$OCH_3$, and —$CF_3$.

In some embodiments, $L^A$ is a covalent bond.

In some embodiments, $L^B$ is a covalent bond, —O—, —NH—, —C(=O)O—, —C(O)NH—, or —$SO_2NH$—.

In some embodiments, $R^{32}$ is H, substituted or unsubstituted alkyl, or haloalkyl; wherein any $R^{32}$ group, when substituted, is substituted with one or more groups selected from halogen, —$NH_2$, —$NO_2$, —CN, —OH, —$CO_2H$, —$CONH_2$, —$SO_3H$, —$SO_2NH_2$, —$SO_2CH_3$, —$OCH_3$, and —$CF_3$. In some embodiments, $R^{32}$ is H, substituted or unsubstituted alkyl, or haloalkyl.

In one aspect, $R^1$, $R^3$, $R^7$, $R^8$, $R^9$, $R^{10}$, $R^{11}$ are as defined in Table 1, Table 2, Table 3 and Table 4. In one aspect, $R^2$, $R^5$, and $R^6$ are each H and $R^1$, $R^3$, $R^7$, $R^8$, $R^9$, $R^{10}$, $R^{11}$ are as defined in Table 1, Table 2, Table 3 and Table 4.

Any combination of the groups described above for the various variables is contemplated herein.

In one aspect, compounds of Formula (I) include, but are not limited to, those described in Table 1:

TABLE 1

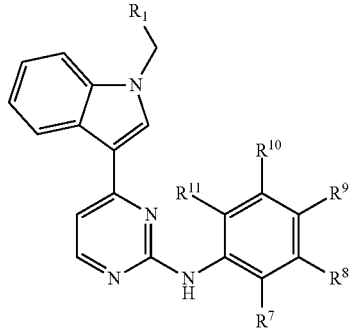

| Compound no. | $R^1$ | $R^7$ | $R^8$ | $R^9$ | $R^{10}$ | $R^{11}$ |
|---|---|---|---|---|---|---|
| 1 | —H | H | —OH | H | H | H |
| 2 | —H | H | H | —OH | H | H |
| 3 | —H | —Cl | H | —OH | H | H |
| 4 | —H | —$CH_3$ | H | —OH | H | H |
| 5 | —H | —$CH_3$ | H | —OH | H | —$CH_3$ |
| 6 | —$CH_3$ | H | H | —OH | H | H |
| 7 | —$CH_3$ | H | —OH | H | H | H |
| 8 | —$CH_3$ | —$CH_3$ | H | —OH | H | H |
| 9 | —$CH_3$ | —$CH_3$ | H | —OH | H | —$CH_3$ |
| 10 | -Phenyl | H | H | —OH | H | H |
| 11 | -Phenyl | H | —OH | H | H | H |

Compound in Table 1 are named:
3-(4-(1-Methyl-1H-indol-3-yl)pyrimidin-2-ylamino)phenol (Compound 1)
4-(4-(1-Methyl-1H-indol-3-yl)pyrimidin-2-ylamino)phenol (Compound 2)
3-Chloro-4-(4-(1-methyl-1H-indol-3-yl)pyrimidin-2-ylamino)phenol (Compound 3)
3-Methyl-4-[4-(1-methyl-1H-indol-3-yl)-pyrimidin-2-ylamino]-phenol (Compound 4)

3,5-Dimethyl-4-[4-(1-methyl-1H-indol-3-yl)-pyrimidin-2-ylamino]-phenol (Compound 5)
4-[4-(1-Ethyl-1H-indol-3-yl)-pyrimidin-2-ylamino]-phenol (Compound 6)
3-[4-(1-Ethyl-1H-indol-3-yl)-pyrimidin-2-ylamino]-phenol (Compound 7)
4-[4-(1-Ethyl-1H-indol-3-yl)-pyrimidin-2-ylamino]-3-methyl-phenol (Compound 8)
4-[4-(1-Ethyl-1H-indol-3-yl)-pyrimidin-2-ylamino]-3,5-dimethyl-phenol (Compound 9)
4-[4-(1-Benzyl-1H-indol-3-yl)-pyrimidin-2-ylamino]-phenol (Compound 10)
3-[4-(1-Benzyl-1H-indol-3-yl)-pyrimidin-2-ylamino]-phenol (Compound 11)

In one aspect, compounds of Formula (I) include, but are not limited to, those described in Table 2:

(3-Nitro-phenyl)-[4-(1-propyl-1H-pyrrolo[2,3-b]pyridin-3-yl)-pyrimidin-2-yl]-amine (Compound 17)
3-(4-(1-Ethyl-1H-pyrrolo[2,3-b]pyridin-3-yl)pyrimidin-2-ylamino)benzenesulfonamide (Compound 18)
3-(4-(1-Ethyl-1H-pyrrolo[2,3-b]pyridin-3-yl)pyrimidin-2-ylamino)benzamide (Compound 19).
3-(4-(1-ethyl-1H-pyrrolo[2,3-b]pyridin-3-yl)pyrimidin-2-ylamino)benzonitrile (Compound 20).
4-(4-(1-ethyl-1H-pyrrolo[2,3-b]pyridin-3-yl)pyrimidin-2-ylamino)benzenesulfonamide (Compound 21).
3-(4-(1-propyl-1H-pyrrolo[2,3-b]pyridin-3-yl)pyrimidin-2-ylamino)benzenesulfonamide (Compound 22).
4-(4-(1-Propyl-1H-pyrrolo[2,3-b]pyridin-3-yl)pyrimidin-2-ylamino)benzenesulfonamide (Compound 23).

TABLE 2

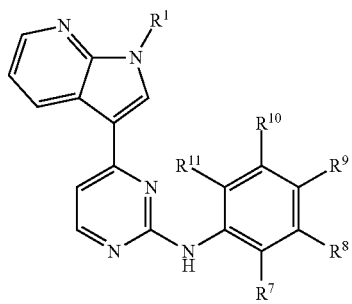

| Compound no. | $R^1$ | $R^7$ | $R^8$ | $R^9$ | $R^{10}$ | $R^{11}$ |
|---|---|---|---|---|---|---|
| 12 | —CH$_2$CH$_3$ | H | H | —OH | H | H |
| 13 | —CH$_2$CH$_3$ | H | —OH | H | H | H |
| 14 | —CH$_2$CH$_3$ | H | —NO$_2$ | H | H | H |
| 15 | —CH$_2$CH$_2$CH$_3$ | H | H | —OH | H | H |
| 16 | CH$_2$CH$_2$CH$_3$ | H | —OH | H | H | H |
| 17 | CH$_2$CH$_2$CH$_3$ | H | —NO$_2$ | H | H | H |
| 18 | CH$_2$CH$_3$ | H | —SO$_2$NH$_2$ | H | H | H |
| 19 | CH$_2$CH$_3$ | H | —CONH$_2$ | H | H | H |
| 20 | CH$_2$CH$_3$ | H | CN | H | H | H |
| 21 | CH$_2$CH$_3$ | H | H | —SO$_2$NH$_2$ | H | H |
| 22 | CH$_2$CH$_2$CH$_3$ | H | —SO$_2$NH$_2$ | H | H | H |
| 23 | CH$_2$CH$_2$CH$_3$ | H | H | SO$_2$NH$_2$ | H | H |
| 24 | CH$_2$CH$_2$CH$_3$ | H | -sulfonylmorpholine | Me | H | H |
| 25 | CH$_2$CH$_2$CH$_3$ | H | -sulfonylpiperazine | H | H | H |
| 26 | CH$_2$CH$_2$CH$_3$ | H | H | -sulfonylpiperazine | H | H |
| 27 | CH$_2$CH$_2$CH$_3$ | H | H | -sulfonylmorpholine | H | H |
| 28 | CH$_2$CH$_2$CH$_3$ | H | -sulfonyl-4-methylpiperazine | H | H | H |
| 29 | CH$_2$CH$_2$CH$_3$ | H | H | -sulfonyl-4-methylpiperazine | H | H |
| 30 | CH$_2$CH$_2$CH$_3$ | H | -morpholine | H | H | H |
| 31 | CH$_2$CH$_2$CH$_3$ | H | H | -morpholine | H | H |
| 32 | CH$_2$CH$_2$CH$_3$ | H | -piperazine | | H | H |
| 33 | CH$_2$CH$_2$CH$_3$ | H | H | -piperazine | H | H |
| 34 | CH$_2$CH$_2$CH$_3$ | H | —C(=O)-4-methylpiperazine | H | H | H |
| 35 | CH$_2$CH$_2$CH$_3$ | H | | -4-methylpiperazine | H | H |
| 36 | CH$_2$CH$_2$CH$_3$ | H | —C(=O)-(4-acetyl piperazin-1-yl)- | H | H | H |
| 37 | CH$_2$CH$_2$CH$_3$ | H | H | —C(=O)-(4-acetyl piperazin-1-yl)- | H | H |

Compound in Table 2 are named:
4-[4-(1-Ethyl-1H-pyrrolo[2,3-b]pyridin-3-yl)-pyrimidin-2-ylamino]-phenol (Compound 12)
3-[4-(1-Ethyl-1H-pyrrolo[2,3-b]pyridin-3-yl)-pyrimidin-2-ylamino]-phenol (Compound 13)
[4-(1-Ethyl-1H-pyrrolo[2,3-b]pyridin-3-yl)-pyrimidin-2-yl]-(3-nitro-phenyl)-amine (Compound 14)
4-[4-(1-Propyl-1H-pyrrolo[2,3-b]pyridin-3-yl)-pyrimidin-2-ylamino]-phenol (Compound 15)
3-[4-(1-Propyl-1H-pyrrolo[2,3-b]pyridin-3-yl)-pyrimidin-2-ylamino]-phenol (Compound 16)

N-(4-Methyl-3-(morpholinosulfonyl)phenyl)-4-(1-propyl-1H-pyrrolo[2,3-b]pyridin-3-yl)pyrimidin-2-amine (Compound 24).
N-(3-(piperazin-1-ylsulfonyl)phenyl)-4-(1-propyl-1H-pyrrolo[2,3-b]pyridin-3-yl)pyrimidin-2-amine (Compound 25).
N-(4-(piperazin-1-yl sulfonyl)phenyl)-4-(1-propyl-1H-pyrrolo[2,3-b]pyridin-3-yl)pyrimidin-2-amine (Compound 26).
N-(4-(Morpholinosulfonyl)phenyl)-4-(1-propyl-1H-pyrrolo[2,3-b]pyridin-3-yl)pyrimidin-2-amine (Compound 27).

N-(3-(4-Methylpiperazin-1-ylsulfonyl)phenyl)-4-(1-propyl-1H-pyrrolo[2,3-b]pyridin-3-yl)pyrimidin-2-amine (Compound 28).

N-(4-(4-Methylpiperazin-1-ylsulfonyl)phenyl)-4-(1-propyl-1H-pyrrolo[2,3-b]pyridin-3-yl)pyrimidin-2-amine (Compound 29).

N-(3-Morpholinophenyl)-4-(1-propyl-1H-pyrrolo[2,3-b]pyridin-3-yl)pyrimidin-2-amine (Compound 30).

N-(4-Morpholinophenyl)-4-(1-propyl-1H-pyrrolo[2,3-b]pyridin-3-yl)pyrimidin-2-amine (Compound 31).

1-(4-(3-(4-(1-Propyl-1H-pyrrolo[2,3-b]pyridin-3-yl)pyrimidin-2-ylamino)phenyl)piperazin-1-yl)ethanone (Compound 36).

1-(4-(4-(4-(1-Propyl-1H-pyrrolo[2,3-b]pyridin-3-yl)pyrimidin-2-ylamino)phenyl)piperazin-1-yl)ethanone (Compound 37).

In one aspect, compounds of Formula (I) include, but are not limited to, those described in Table 3:

TABLE 3

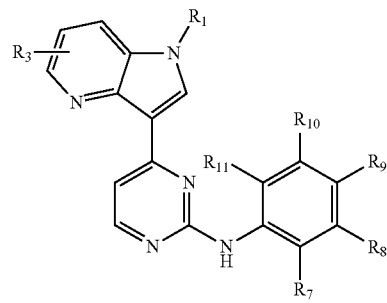

| Compound no. | $R^1$ | $R^3$ | $R^7$ | $R^8$ | $R^9$ | $R^{10}$ | $R^{11}$ |
|---|---|---|---|---|---|---|---|
| 38 | $CH_2CH_2H_3$ | 5-Cl, 7-$CH_3$ | H | H | —OH | H | H |
| 39 | $CH_2CH_2H_3$ | 5-Cl, 7-$CH_3$ | H | H | —$SO_2NH_2$ | H | H |
| 40 | $CH_2CH_2H_3$ | 5-Cl, 7-$CH_3$ | H | —OH | H | H | H |
| 41 | $CH_2CH_2H_3$ | 5-Cl, 7-$CH_3$ | Me | H | —OH | H | H |
| 42 | $CH_2CH_2H_3$ | 5-Cl, 7-$CH_3$ | H | —$SO_2NH_2$ | H | H | H |
| 43 | $CH_2CH_2H_3$ | 5-Cl, 7-$CH_3$ | H | -sulfonylmorpholine | Me | H | H |
| 44 | $CH_2CH_2H_3$ | 5-Cl, 7-$CH_3$ | H | -sulfonylpiperazine | H | H | H |
| 45 | $CH_2CH_2H_3$ | 5-Cl, 7-$CH_3$ | H | H | -sulfonylpiperazine | H | H |
| 46 | $CH_2CH_2H_3$ | 5-Cl, 7-$CH_3$ | H | -piperazine | H | H | H |
| 47 | $CH_2CH_2H_3$ | 5-Cl, 7-$CH_3$ | H | H | -piperazine | H | H |
| 48 | $CH_2CH_2H_3$ | 5-Cl, 7-$CH_3$ | H | -morpholine | H | H | H |
| 49 | $CH_2CH_2H_3$ | 5-Cl, 7-$CH_3$ | H | H | -morpholine | H | H |
| 50 | $CH_2CH_2H_3$ | 5-Cl, 7-$CH_3$ | H | —C(=O)-(4-acetyl piperazin-1-yl)- | H | H | H |
| 51 | $CH_2CH_2H_3$ | 5-Cl, 7-$CH_3$ | H | H | —C(=O)-(4-acetyl piperazin-1-yl) | H | H |
| 52 | $CH_2CH_2H_3$ | 5-Cl, 7-$CH_3$ | H | C(=O)-morpholine | H | H | H |
| 53 | $CH_2CH_2H_3$ | 5-Cl, 7-$CH_3$ | H | H | C(=O)-morpholine | H | H |
| 54 | $CH_2CH_2H_3$ | 7-$CH_3$ | H | —$SO_2NH_2$ | H | H | H |
| 55 | $CH_2CH_2H_3$ | 7-$CH_3$ | H | H | —$SO_2NH_2$ | H | H |
| 56 | $CH_2CH_2H_3$ | 7-$CH_3$ | H | -sulfonylpiperazine | H | H | H |
| 57 | $CH_2CH_2H_3$ | 7-$CH_3$ | H | H | -sulfonylpiperazine | H | H |
| 58 | $CH_2CH_2H_3$ | 7-$CH_3$ | H | -piperazine | H | H | H |
| 59 | $CH_2CH_2H_3$ | 7-$CH_3$ | H | H | -piperazine | H | H |
| 60 | $CH_2CH_2H_3$ | 7-$CH_3$ | H | -morpholine | H | H | H |
| 61 | $CH_2CH_2H_3$ | 7-$CH_3$ | H | H | -morpholine | H | H |
| 62 | $CH_2CH_2H_3$ | 7-$CH_3$ | H | —C(=O)-(4-acetyl piperazin-1-yl)- | H | H | H |
| 63 | $CH_2CH_2H_3$ | 7-$CH_3$ | H | H | —C(=O)-(4-acetyl piperazin-1-yl)- | H | H |
| 64 | $CH_2H_3$ | 7-$CH_3$ | H | —$SO_2NH_2$ | H | H | H |
| 65 | $CH_2H_3$ | 7-$CH_3$ | H | H | —$SO_2NH_2$ | H | H |
| 66 | $CH_2H_3$ | 7-$CH_3$ | H | —C(=O)-morpholine | H | H | H |
| 67 | $CH_2H_3$ | 7-$CH_3$ | H | H | —C(=O)-morpholine | H | H |
| 68 | $CH_2H_3$ | 7-$CH_3$ | H | -piperazine | H | H | H |
| 69 | $CH_2H_3$ | 7-$CH_3$ | H | H | -piperazine | H | H |

N-(3-(piperazin-1-yl)phenyl)-4-(1-propyl-1H-pyrrolo[2,3-b]pyridin-3-yl)pyrimidin-2-amine (Compound 32).

N-(4-(piperazin-1-yl)phenyl)-4-(1-propyl-1H-pyrrolo[2,3-b]pyridin-3-yl)pyrimidin-2-amine (Compound 33).

(4-Methylpiperazin-1-yl)(3-(4-(1-propyl-1H-pyrrolo[2,3-b]pyridin-3-yl)pyrimidin-2-ylamino)phenyl)methanone (Compound 34).

N-(4-(4-Methylpiperazin-1-yl)phenyl)-4-(1-propyl-1H-pyrrolo[2,3-b]pyridin-3-yl)pyrimidin-2-amine (Compound 35).

Compound in Table 3 are named:

4-(4-(5-Chloro-7-methyl-1-propyl-1H-pyrrolo[3,2-b]pyridin-3-yl)pyrimidin-2-ylamino)phenol (Compound 38).

4-(4-(5-Chloro-7-methyl-1-propyl-1H-pyrrolo[3,2-b]pyridin-3-yl)pyrimidin-2-ylamino)benzenesulfonamide (Compound 39)

3-(4-(5-Chloro-7-methyl-1-propyl-1H-pyrrolo[3,2-b]pyridin-3-yl)pyrimidin-2-ylamino)phenol (Compound 40).

4-(4-(5-Chloro-7-methyl-1-propyl-1H-pyrrolo[3,2-b]pyridin-3-yl)pyrimidin-2-ylamino)-3-methylphenol (Compound 41).

3-(4-(5-Chloro-7-methyl-1-propyl-1H-pyrrolo[3,2-b]pyridin-3-yl)pyrimidin-2-ylamino)benzenesulfonamide (Compound 42)

4-(5-Chloro-7-methyl-1-propyl-1H-pyrrolo[3,2-b]pyridin-3-yl)-N-(4-methyl-3-(morpholinosulfonyl)phenyl)pyrimidin-2-amine (Compound 43)

4-(5-Chloro-7-methyl-1-propyl-1H-pyrrolo[3,2-b]pyridin-3-yl)-N-(3-(piperazin-1-ylsulfonyl)phenyl)pyrimidin-2-amine (Compound 44)

4-(5-Chloro-7-methyl-1-propyl-1H-pyrrolo[3,2-b]pyridin-3-yl)-N-(4-(piperazin-1-ylsulfonyl)phenyl)pyrimidin-2-amine (Compound 45)

4-(5-Chloro-7-methyl-1-propyl-1H-pyrrolo[3,2-b]pyridin-3-yl)-N-(3-(piperazin-1-yl)phenyl)pyrimidin-2-amine (Compound 46).

4-(5-Chloro-7-methyl-1-propyl-1H-pyrrolo[3,2-b]pyridin-3-yl)-N-(4-(piperazin-1-yl)phenyl)pyrimidin-2-amine (Compound 47)

4-(5-Chloro-7-methyl-1-propyl-1H-pyrrolo[3,2-b]pyridin-3-yl)-N-(3-morpholinophenyl)pyrimidin-2-amine (Compound 48).

4-(5-Chloro-7-methyl-1-propyl-1H-pyrrolo[3,2-b]pyridin-3-yl)-N-(4-morpholinophenyl)pyrimidin-2-amine (Compound 49).

1-(4-(3-(4-(5-Chloro-7-methyl-1-propyl-1H-pyrrolo[3,2-b]pyridin-3-yl)pyrimidin-2-ylamino)phenyl)piperazin-1-yl)ethanone (Compound 50).

1-(4-(4-(4-(5-Chloro-7-methyl-1-propyl-1H-pyrrolo[3,2-b]pyridin-3-yl)pyrimidin-2-ylamino)phenyl)piperazin-1-yl)ethanone (Compound 51).

(3-(4-(5-Chloro-7-methyl-1-propyl-1H-pyrrolo[3,2-b]pyridin-3-yl)pyrimidin-2-ylamino)phenyl)(morpholino)methanone (Compound 52).

(4-(4-(5-Chloro-7-methyl-1-propyl-1H-pyrrolo[3,2-b]pyridin-3-yl)pyrimidin-2-ylamino)phenyl)(morpholino)methanone (Compound 53).

3-(4-(7-Methyl-1-propyl-1H-pyrrolo[3,2-b]pyridin-3-yl)pyrimidin-2-ylamino)benzenesulfonamide (Compound 54).

4-(4-(7-Methyl-1-propyl-1H-pyrrolo[3,2-b]pyridin-3-yl)pyrimidin-2-ylamino)benzenesulfonamide (Compound 55).

4-(7-Methyl-1-propyl-1H-pyrrolo[3,2-b]pyridin-3-yl)-N-(3-(piperazin-1-ylsulfonyl)phenyl)pyrimidin-2-amine (Compound 56).

4-(7-Methyl-1-propyl-1H-pyrrolo[3,2-b]pyridin-3-yl)-N-(4-(piperazin-1-ylsulfonyl)phenyl)pyrimidin-2-amine (Compound 57).

4-(7-Methyl-1-propyl-1H-pyrrolo[3,2-b]pyridin-3-yl)-N-(3-(piperazin-1-yl)phenyl)pyrimidin-2-amine (Compound 58).

4-(7-Methyl-1-propyl-1H-pyrrolo[3,2-b]pyridin-3-yl)-N-(4-(piperazin-1-yl)phenyl)pyrimidin-2-amine (Compound 59).

4-(7-Methyl-1-propyl-1H-pyrrolo[3,2-b]pyridin-3-yl)-N-(3-morpholinophenyl)pyrimidin-2-amine (Compound 60).

4-(7-Methyl-1-propyl-1H-pyrrolo[3,2-b]pyridin-3-yl)-N-(4-morpholinophenyl)pyrimidin-2-amine (Compound 61).

1-(4-(3-(4-(7-Methyl-1-propyl-1H-pyrrolo[3,2-b]pyridin-3-yl)pyrimidin-2-ylamino)phenyl)piperazin-1-yl)ethanone (Compound 62).

1-(4-(4-(4-(7-Methyl-1-propyl-1H-pyrrolo[3,2-b]pyridin-3-yl)pyrimidin-2-ylamino)phenyl)piperazin-1-yl)ethanone (Compound 63).

3-(4-(1-Ethyl-7-methyl-1H-pyrrolo[3,2-b]pyridin-3-yl)pyrimidin-2-ylamino)benzenesulfonamide (Compound 64).

4-(4-(1-Ethyl-7-methyl-1H-pyrrolo[3,2-b]pyridin-3-yl)pyrimidin-2-ylamino)benzenesulfonamide (Compound 65).

(3-(4-(1-Ethyl-7-methyl-1H-pyrrolo[3,2-b]pyridin-3-yl)pyrimidin-2-ylamino)phenyl)(morpholino)methanone (Compound 66).

(4-(4-(1-Ethyl-7-methyl-1H-pyrrolo[3,2-b]pyridin-3-yl)pyrimidin-2-ylamino)phenyl)(morpholino)methanone (Compound 67).

4-(1-Ethyl-7-methyl-1H-pyrrolo[3,2-b]pyridin-3-yl)-N-(3-(piperazin-1-yl)phenyl)pyrimidin-2-amine (Compound 68).

4-(1-Ethyl-7-methyl-1H-pyrrolo[3,2-b]pyridin-3-yl)-N-(4-(piperazin-1-yl)phenyl)pyrimidin-2-amine (Compound 69).

TABLE 4

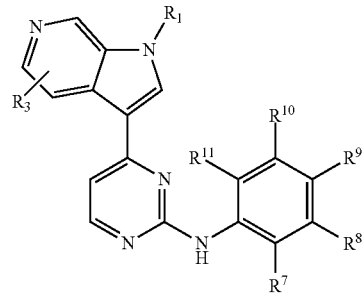

| Comp. no. | $R^1$ | $R^3$ | $R^7$ | $R^8$ | $R^9$ | $R^{10}$ | $R^{11}$ |
|---|---|---|---|---|---|---|---|
| 70 | —CH$_2$CH$_3$ | 7-Cl | H | H | —OH | H | H |
| 71 | —CH$_2$CH$_3$ | 7-Cl | H | H | —SO$_2$NH$_2$ | H | H |
| 72 | —CH$_2$CH$_3$ | 7-Cl | H | —OH | H | H | H |
| 73 | —CH$_2$CH$_3$ | 7-Cl | H | —SO$_2$NH$_2$ | H | H | H |
| 74 | —CH$_2$CH$_3$ | 7-Cl | H | -sulfonylmorpholine | Me | H | H |
| 75 | —CH$_2$CH$_3$ | 7-Cl | H | —C(=O)-morpholine | H | H | H |
| 76 | —CH$_2$CH$_3$ | 7-Cl | H | H | —C(=O)-morpholine | H | H |
| 77 | —CH$_2$CH$_3$ | 7-Cl | H | -sulfonylpiperazine | H | H | H |
| 78 | —CH$_2$CH$_3$ | 7-Cl | H | H | -sulfonylpiperazine | H | H |
| 79 | —CH$_2$CH$_3$ | 7-Cl | H | -piperazine | H | H | H |
| 80 | —CH$_2$CH$_3$ | 7-Cl | H | H | -piperazine | H | H |

TABLE 4-continued

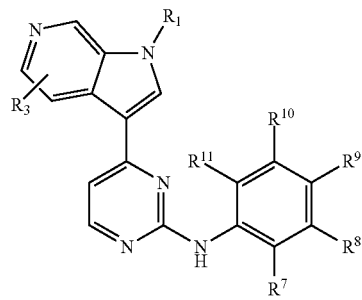

| Comp. no. | R¹ | R³ | R⁷ | R⁸ | R⁹ | R¹⁰ | R¹¹ |
|---|---|---|---|---|---|---|---|
| 81 | —CH₂CH₃ | 7-Cl | H | -morpholine | H | H | H |
| 82 | —CH₂CH₃ | 7-Cl | H | H | -morpholine | H | H |
| 83 | —CH₂CH₃ | H | H | OH | H | H | H |
| 84 | —CH₂CH₃ | H | H | —SO₂NH₂ | H | H | H |
| 85 | —CH₂CH₃ | H | H | H | OH | H | H |
| 86 | —CH₂CH₃ | H | H | H | —SO₂NH₂ | H | H |
| 87 | —CH₂CH₃ | H | H | -sulfonylmorpholine | Me | H | H |
| 88 | —CH₂CH₃ | H | H | —C(=O)-morphline | H | H | H |
| 89 | CH₂CH₃ | H | H | H | —C(=O)-morphline | H | H |
| 90 | CH₂CH₃ | H | H | —C(=O)-(4-acetyl piperazin-1-yl)- | H | H | H |
| 91 | CH₂CH₃ | H | H | H | —C(=O)-(4-acetyl piperazin-1-yl)- | H | H |
| 92 | CH₂CH₃ | H | H | -piperazine | H | H | H |
| 93 | CH₂CH₃ | H | H | H | -piperazine | H | H |
| 94 | CH₂CH₃ | H | H | -morpholine | H | H | H |
| 95 | CH₂CH₃ | H | H | H | -morpholine | H | H |
| 96 | CH₂CH₂CH₃ | 7-Cl | H | —SO₂NH₂ | H | H | H |
| 97 | CH₂CH₂CH₃ | 7-Cl | H | H | —SO₂NH₂ | H | H |
| 98 | CH₂CH₂CH₃ | 7-Cl | H | —C(=O)-(4-acetyl piperazin-1-yl)- | H | H | H |
| 99 | CH₂CH₂CH₃ | 7-Cl | H | H | —C(=O)-(4-acetyl piperazin-1-yl)- | H | H |
| 100 | CH₂CH₂CH₃ | 7-Cl | H | H | -morpholine | H | H |
| 101 | CH₂CH₂CH₃ | 7-Cl | H | —SO₂-morpholine | Me | H | H |
| 102 | CH₂CH₂CH₃ | H | H | —SO₂-morpholine | Me | H | H |
| 103 | CH₂CH₂CH₃ | H | H | H | -morpholine | H | H |
| 104 | CH₂CH₂CH₃ | H | H | -piperazine | H | H | H |
| 105 | CH₂CH₂CH₃ | H | H | H | -piperazine | H | H |
| 106 | CH₂CH₂CH₃ | H | H | H | —C(=O)-(4-acetyl piperazin-1-yl)- | H | H |
| 107 | CH₂CH₂CH₃ | H | H | —C(=O)-piperazin- | H | H | H |
| 108 | CH₂CH₂CH₃ | H | H | —C(=O)-morpholine | H | H | H |
| 109 | CH₂CH₂CH₃ | H | H | H | —C(=O)-piperazin- | H | H |
| 110 | CH₂CH₂CH₃ | H | H | H | —C(=O)-morpholine | H | H |
| 111 | CH₂CH₂CH₃ | H | H | —SO₂NH₂ | H | H | H |
| 112 | CH₂CH₂CH₃ | H | H | H | —SO₂NH₂ | H | H |

Compound in Table 4 are named:

4-(4-(7-Chloro-1-ethyl-1H-pyrrolo[2,3-c]pyridin-3-yl)pyrimidin-2-ylamino)phenol (Compound 70)

4-(4-(7-Chloro-1-ethyl-1H-pyrrolo[2,3-c]pyridin-3-yl)pyrimidin-2-ylamino)benzenesulfonamide (Compound 71)

3-(4-(7-Chloro-1-ethyl-1H-pyrrolo[2,3-c]pyridin-3-yl)pyrimidin-2-ylamino)phenol (Compound 72)

3-(4-(7-Chloro-1-ethyl-1H-pyrrolo[2,3-c]pyridin-3-yl)pyrimidin-2-ylamino)benzenesulfonamide (Compound 73)

4-(7-Chloro-1-ethyl-1H-pyrrolo[2,3-c]pyridin-3-yl)-N-(4-methyl-3-(morpholinosulfonyl)phenyl)pyrimidin-2-amine (Compound 74)

(3-(4-(7-Chloro-1-ethyl-1H-pyrrolo[2,3-c]pyridin-3-yl)pyrimidin-2-ylamino)phenyl)(morpholino)methanone (Compound 75)

(4-(4-(7-Chloro-1-ethyl-1H-pyrrolo[2,3-c]pyridin-3-yl)pyrimidin-2-ylamino)phenyl)(morpholino)methanone (Compound 76)

4-(7-Chloro-1-ethyl-1H-pyrrolo[2,3-c]pyridin-3-yl)-N-(3-(piperazin-1-ylsulfonyl)phenyl)pyrimidin-2-amine (Compound 77)

4-(7-Chloro-1-ethyl-1H-pyrrolo[2,3-c]pyridin-3-yl)-N-(4-(piperazin-1-ylsulfonyl)phenyl)pyrimidin-2-amine (Compound 78).

4-(7-Chloro-1-ethyl-1H-pyrrolo[2,3-c]pyridin-3-yl)-N-(3-(piperazin-1-yl)phenyl)pyrimidin-2-amine (Compound 79).

4-(7-Chloro-1-ethyl-1H-pyrrolo[2,3-c]pyridin-3-yl)-N-(4-(piperazin-1-yl)phenyl)pyrimidin-2-amine (Compound 80).

4-(7-Chloro-1-ethyl-1H-pyrrolo[2,3-c]pyridin-3-yl)-N-(3-morpholinophenyl)pyrimidin-2-amine (Compound 81).

4-(7-Chloro-1-ethyl-1H-pyrrolo[2,3-c]pyridin-3-yl)-N-(4-morpholinophenyl)pyrimidin-2-amine (Compound 82).

3-(4-(1-Ethyl-1H-pyrrolo[2,3-c]pyridin-3-yl)pyrimidin-2-ylamino)phenol (Compound 83).

3-(4-(1-Ethyl-1H-pyrrolo[2,3-c]pyridin-3-yl)pyrimidin-2-ylamino)benzenesulfonamide (Compound 84).

4-(4-(1-Ethyl-1H-pyrrolo[2,3-c]pyridin-3-yl)pyrimidin-2-ylamino)phenol (Compound 85).

4-(4-(1-Ethyl-1H-pyrrolo[2,3-c]pyridin-3-yl)pyrimidin-2-ylamino)benzenesulfonamide (Compound 86).

4-(1-Ethyl-1H-pyrrolo[2,3-c]pyridin-3-yl)-N-(4-methyl-3-(morpholinosulfonyl)phenyl)pyrimidin-2-amine (Compound 87).

(3-(4-(1-Ethyl-1H-pyrrolo[2,3-c]pyridin-3-yl)pyrimidin-2-ylamino)phenyl)(morpholino)methanone (Compound 88).

(4-(4-(1-Ethyl-1H-pyrrolo[2,3-c]pyridin-3-yl)pyrimidin-2-ylamino)phenyl)(morpholino)methanone (Compound 89).

1-(4-(3-(4-(1-Ethyl-1H-pyrrolo[2,3-c]pyridin-3-yl)pyrimidin-2-ylamino)benzoyl)piperazin-1-yl)ethanone (Compound 90).

1-(4-(4-(4-(1-Ethyl-1H-pyrrolo[2,3-c]pyridin-3-yl)pyrimidin-2-ylamino)benzoyl)piperazin-1-yl)ethanone (Compound 91).

4-(1-Ethyl-1H-pyrrolo[2,3-c]pyridin-3-yl)-N-(3-(piperazin-1-yl)phenyl)pyrimidin-2-amine (Compound 92).

4-(1-Ethyl-1H-pyrrolo[2,3-c]pyridin-3-yl)-N-(4-(piperazin-1-yl)phenyl)pyrimidin-2-amine (Compound 93).

4-(1-Ethyl-1H-pyrrolo[2,3-c]pyridin-3-yl)-N-(3-morpholinophenyl)pyrimidin-2-amine (Compound 94).

4-(1-Ethyl-1H-pyrrolo[2,3-c]pyridin-3-yl)-N-(4-morpholinophenyl)pyrimidin-2-amine (Compound 95).

4-(4-(7-Chloro-1-propyl-1H-pyrrolo[2,3-c]pyridin-3-yl)pyrimidin-2-ylamino)benzenesulfonamide (Compound 96).

3-(4-(7-Chloro-1-propyl-1H-pyrrolo[2,3-c]pyridin-3-yl)pyrimidin-2-ylamino)benzenesulfonamide (Compound 97).

1-(4-(3-(4-(7-Chloro-1-propyl-1H-pyrrolo[2,3-c]pyridin-3-yl)pyrimidin-2-ylamino)benzoyl)piperazin-1-yl)ethanone (Compound 98).

1-(4-(4-(4-(7-Chloro-1-propyl-1H-pyrrolo[2,3-c]pyridin-3-yl)pyrimidin-2-ylamino)benzoyl)piperazin-1-yl)ethanone (Compound 99).

4-(7-Chloro-1-propyl-1H-pyrrolo[2,3-c]pyridin-3-yl)-N-(4-morpholinophenyl)pyrimidin-2-amine (Compound 100).

4-(7-Chloro-1-propyl-1H-pyrrolo[2,3-c]pyridin-3-yl)-N-(4-methyl-3-(morpholinosulfonyl)phenyl)pyrimidin-2-amine (Compound 101).

N-(4-Methyl-3-(morpholinosulfonyl)phenyl)-4-(1-propyl-1H-pyrrolo[2,3-c]pyridin-3-yl)pyrimidin-2-amine (Compound 102).

N-(4-Morpholinophenyl)-4-(1-propyl-1H-pyrrolo[2,3-c]pyridin-3-yl)pyrimidin-2-amine (Compound 103).

N-(3-(piperazin-1-yl)phenyl)-4-(1-propyl-1H-pyrrolo[2,3-c]pyridin-3-yl)pyrimidin-2-amine (Compound 104).

N-(4-(piperazin-1-yl)phenyl)-4-(1-propyl-1H-pyrrolo[2,3-c]pyridin-3-yl)pyrimidin-2-amine (Compound 105).

1-(4-(4-(4-(1-Propyl-1H-pyrrolo[2,3-c]pyridin-3-yl)pyrimidin-2-ylamino)benzoyl)piperazin-1-yl)ethanone (Compound 106).

Piperazin-1-yl(3-(4-(1-propyl-1H-pyrrolo[2,3-c]pyridin-3-yl)pyrimidin-2-ylamino)phenyl)methanone (Compound 107).

Morpholino(3-(4-(1-propyl-1H-pyrrolo[2,3-c]pyridin-3-yl)pyrimidin-2-ylamino)phenyl)methanone (Compound 108).

Piperazin-1-yl(4-(4-(1-propyl-1H-pyrrolo[2,3-c]pyridin-3-yl)pyrimidin-2-ylamino)phenyl)methanone (Compound 109).

Morpholino(4-(4-(1-propyl-1H-pyrrolo[2,3-c]pyridin-3-yl)pyrimidin-2-ylamino)phenyl)methanone (Compound 110).

3-(4-(1-Propyl-1H-pyrrolo[2,3-c]pyridin-3-yl)pyrimidin-2-ylamino)benzenesulfonamide (Compound 111).

4-(4-(1-Propyl-1H-pyrrolo[2,3-c]pyridin-3-yl)pyrimidin-2-ylamino)benzenesulfonamide (Compound 112).

Synthesis of Compounds

Compounds of Formula (I) described in the prior section are synthesized using standard synthetic techniques or using methods known in the art in combination with methods described herein. In additions, solvents, temperatures and other reaction conditions presented herein may vary.

The starting material used for the synthesis of the compounds of Formula (I) described in the prior section are either synthesized or obtained from commercial sources, such as, but not limited to, Aldrich Chemical Co. (Milwaukee, Wis.), or Sigma Chemical Co. (St. Louis, Mo.). The compounds described herein, and other related compounds having different substituents are synthesized using known techniques and materials, including those found in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001), and Green and Wuts, PROTECTIVE GROUPS IN ORGANIC SYNTHESIS 3$^{rd}$ Ed., (Wiley 1999). General methods for the preparation of compounds can be modified by the use of appropriate reagents and conditions for the introduction of the various moieties found in the formulae as provided herein.

In one aspect, compounds described herein are prepared according to methods known in the art. In one aspect, compounds disclosed herein are prepared as outlined in Scheme 1 and Scheme 2.

Scheme 1

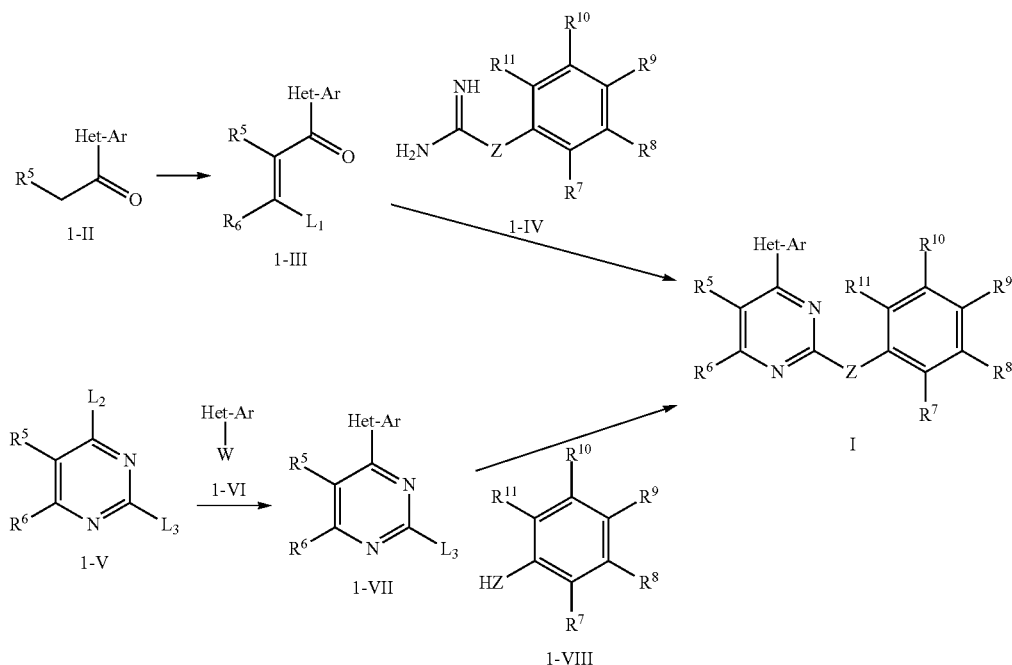

In one aspect, acylheteroaryl compounds of structure 1-II are converted to an acrylate compound of structure 1-III. In one aspect, Het-Ar is a bicyclic heteroaryl that includes at least one nitrogen in the bicyclic ring. In one aspect, Het-Ar is selected from indole, pyrrolo[2,3-b]pyridine, pyrrolo[2,3-c]pyridine, pyrrolo[3,2-b]pyridine, and pyrrolo[3,2-c]pyridine, where Het-Ar is substituted or unsubstituted. In one aspect, Het-Ar is selected from indol-3-yl, pyrrolo[2,3-b]pyridine-2-yl, pyrrolo[2,3-c]pyridine-3-yl, pyrrolo[3,2-b]pyridine-3-yl and pyrrolo[3,2-c]pyridine-3-yl, where Het-Ar is substituted or unsubstituted.

In one aspect, acrylate compounds of structure 1-III are reacted with phenylguanidine compounds of structure 1-IV to provide compounds of Formula (I). In one aspect, $L_1$ is any leaving group. In some embodiments, $L_1$ is N(alkyl)$_2$, halogen, ester (—OC(=O)R), or thioester. In one aspect, $L_1$ is —NMe$_2$.

In another aspect, a compound of structure 1-VI, where W is a halide, triflate or boronic acid, boronate ester, or other suitable group, is reacted with a pyrimidine compound of structure 1-V, where $L_2$ and $L_3$ are leaving groups, such as a halide. Suitable reaction conditions include, but are not limited to, metal-mediated reactions such as Suzuki reactions, Stille cross couplings, Negishi couplings, Kumada couplings, Ullmann reactions, Hiyama Coupling, and variants thereof (Metal-Catalyzed Cross-Coupling Reactions, Armin de Meijere (Editor), Francois Diederich (Editor), John Wiley & Sons; 2nd edition, 2004; Özdemir, et al., *Tetrahedron,* 2005, 61, 9791-9798; Ackermann, et al., *Org. Lett.,* 2006, 8, 3457-3460; Blakey, et al., *J. Am. Chem. Soc.,* 2003, 125, 6046-6047; Dai, et al., *Org. Lett.,* 2004, 6, 221-224; Yoshikai, et al, *J. Am. Chem. Soc.,* 2005, 127, 17978-17979; Tang, et al, *J. Org. Chem.,* 2006, 71, 2167-2169; Murata, et al., *Synthesis,* 2001, 2231-2233).

In one aspect, compounds of structure 1-VII are reacted with compounds of 1-VIII to provide compounds of Formula (I). In one aspect, Z is NH. Suitable reaction conditions include, but are not limited to, metal-catalyzed cross couplings and SN$_{AR}$ reaction conditions.

In one aspect, treatment of 1-V with 1-VI, and a Grignard reagent such as alkyl magnesium bromide, forms 1-VII which reacts as hereinbefore defined with 1-VIII to provide the compounds of formula I.

In one aspect, Het-Ar is a 1-substituted indol-3-yl, 1-substituted pyrrolo[2,3-b]pyridine-3-yl, 1-substituted pyrrolo[2,3-c]pyridine-3-yl, or 1-substituted pyrrolo[3,2-b]pyridine-3-yl. In one aspect, the 1-substitutent of the 1-substituted indol-3-yl, 1-substituted pyrrolo[2,3-b]pyridine-3-yl, 1-substituted pyrrolo[2,3-c]pyridine-3-yl, or 1-substituted pyrrolo[3,2-b]pyridine-3-yl is selected from —C$_1$-C$_6$alkyl, and —C$_1$-C$_6$alkyl(substituted or unsubstituted aryl). In one aspect, the 1-substitutent of the 1-substituted indol-3-yl, 1-substituted pyrrolo[2,3-b]pyridine-3-yl, 1-substituted pyrrolo[2,3-c]pyridine-3-yl, or 1-substituted pyrrolo[3,2-b]pyridine-3-yl is selected from —CH$_3$, —CH$_2$CH$_3$, —CH$_2$CH$_2$CH$_3$, and benzyl.

In one aspect, methods and reaction conditions are as described in Wang, S, et al. *J. Med. Chem.* 2004, 47, 1662.

In another aspect, compounds described herein are prepared as outlined in Scheme 2.

Scheme 2

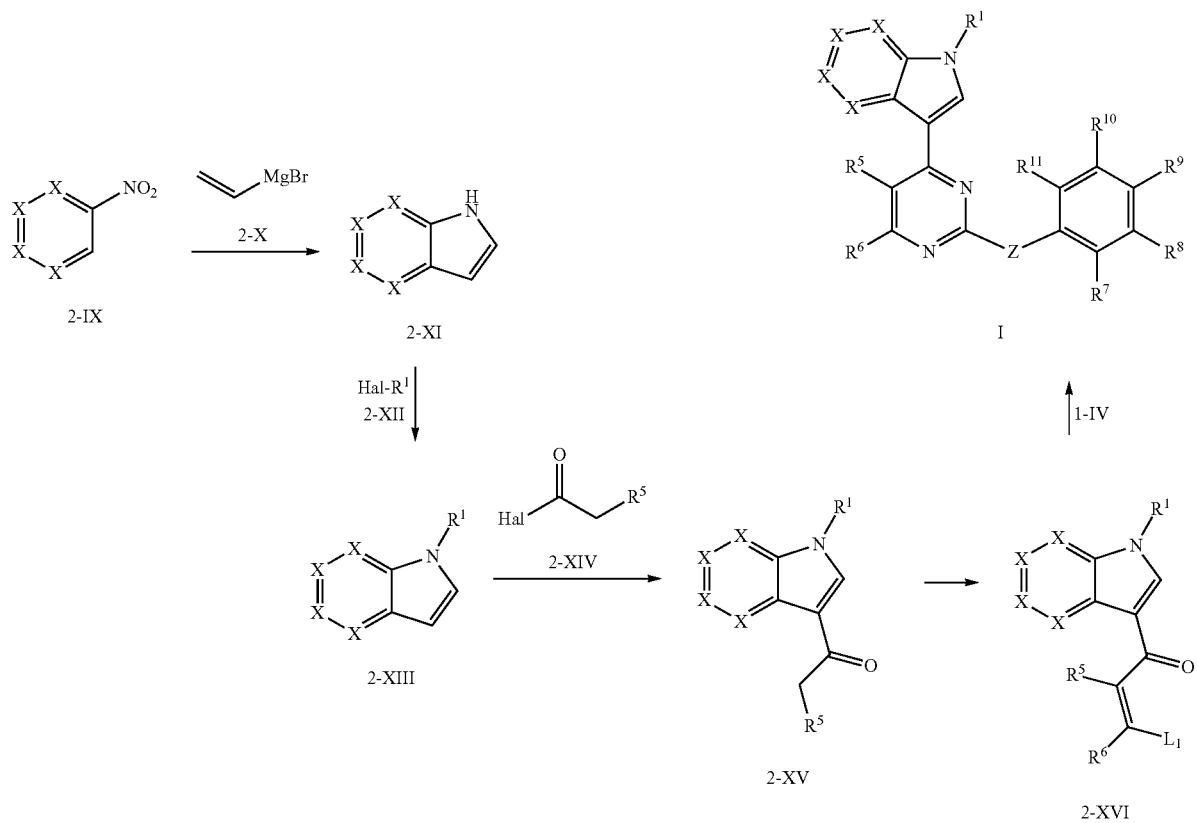

In one aspect, nitrobenzene compounds or nitro-pyridine compounds of structure 2-IX, where X is either N or C—$R^3$, are reacted with vinylmagnesium bromide to provide compounds of structure 2-XI. In one aspect, at least two X are C—$R^3$. In one aspect, at least three X are C—$R^3$. In one aspect, the process of reacting 2-IX with a Grignard agent is as described in Zhang, Z, et al. *J. Org. Chem.*, 2002, 67, 2345.

N-Alkylation of compounds of structure 2-XI with compounds of 2-XII (where Hal is a halide) provides compounds of structure 2-XIII. In one aspect, compounds of structure 2-XI are reacted with compounds of 2-XII in the presence of a base, such as, but not limited to NaH or KOH.

Compounds of structure 2-XIII are acylated with compounds of structure 2-XIV to provide compounds of structure 2-XV. Suitable reaction conditions include, but are not limited to, Friedel-Crafts acylation conditions.

Compounds of structure 2-XV are converted to acrylate compounds of structure 2-XVI, where $L_1$ is any leaving group. In some embodiments, $L_1$ is N(alkyl)$_2$, halogen, ester (—OC(=O)R), or thioester. In one aspect, $L_1$ is —NMe$_2$. In one aspect, compounds of structure 2-XV are reacted with N,N'-dimethylformamide dimethylacetal (where $R^6$=H, $L_1$=NMe$_2$) or tert-butoxy-bis(dimethylamino)methane (Bredereck, H.; et al. *Chemische Berichte* 1964, 97, (12), 3397) to provide acrylate compounds of structure 2-XVI.

Compounds of structure 2-XVI are reacted with phenylguanidine of structure 1-IV to provide compounds of Formula (I).

In one aspect, phenylguanidines of structure 1-IV are obtained by reaction of cyanamide or cyanamide derivatives using the method of Katritzky, A. R: et al. *Synthetic Communications* 1995, 25, 1173.

In one aspect, compounds of Formula (I) are synthesized as outlined in the Examples.

Use of Protecting Groups

In the reactions described, it is necessary in certain embodiments to protect reactive functional groups, for example hydroxy, amino, thiol or carboxy groups, where these are desired in the final product, to avoid their unwanted participation in the reactions. Protecting groups are used to block some or all reactive moieties and prevent such groups from participating in chemical reactions until the protective group is removed. In one embodiment, each protective group is removable by a different means. Protective groups that are cleaved under totally disparate reaction conditions fulfill the requirement of differential removal. In some embodiments, protective groups are removed by acid, base, and/or hydrogenolysis. Groups such as trityl, dimethoxytrityl, acetal and t-butyldimethylsilyl are acid labile and are used in certain embodiments to protect carboxy and hydroxy reactive moieties in the presence of amino groups protected with Cbz groups, which are removable by hydrogenolysis, and/or Fmoc groups, which are base labile. In other embodiments, carboxylic acid and hydroxy reactive moieties are blocked with base labile groups such as, but not limited to, methyl, ethyl, and acetyl in the presence of amines blocked with acid labile groups such as t-butyl carbamate or with carbamates that are both acid and base stable but hydrolytically removable.

In another embodiment, carboxylic acid and hydroxy reactive moieties are blocked with hydrolytically removable protective groups such as the benzyl group, while amine groups capable of hydrogen bonding with acids are blocked with base labile groups such as Fmoc. In another embodiment, carboxylic acid reactive moieties are protected by conversion to simple ester compounds as exemplified herein, or they are, in yet another embodiment, blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a Pd(0)-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and cannot react. Once released from the resin, the functional group is available to react.

Typically blocking/protecting groups are, by way of example only:

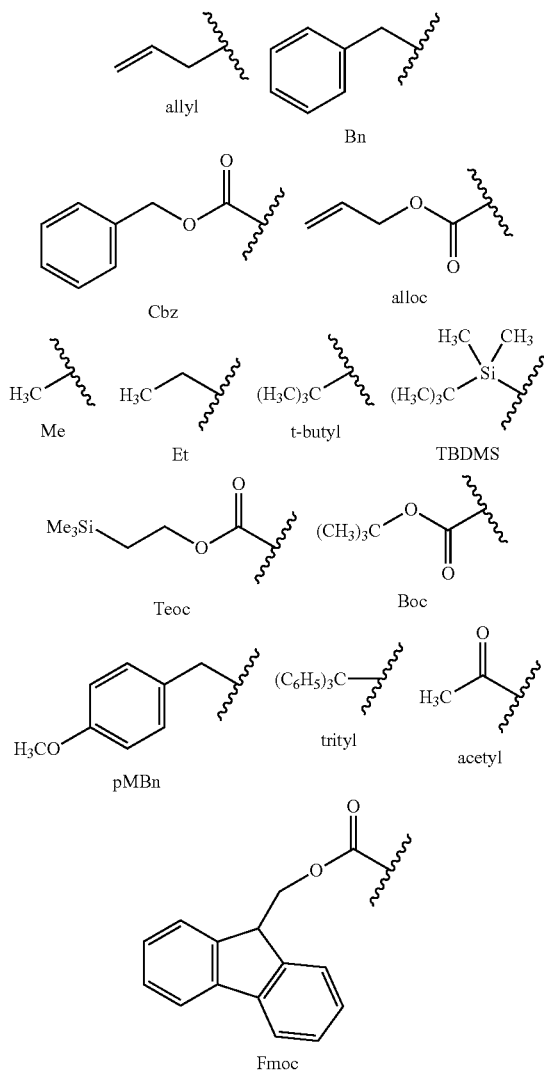

Other protecting groups, plus a detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Further Forms of Compounds

In certain embodiments, compounds of Formula (I) are prepared as a pharmaceutically acceptable acid addition salt (which is a type of a pharmaceutically acceptable salt) by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

By "pharmaceutically acceptable," as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of Formula (I) with acids such as hydrochloric acid, hydrobromic acid, sulfuric acid, nitric acid, phosphoric acid, methanesulfonic acid, ethanesulfonic acid, p-toluenesulfonic acid, salicylic acid and the like. Pharmaceutically acceptable salts are also obtained by reacting a compound of Formula (I) with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

In other embodiments, compounds of Formula (I) are prepared as a pharmaceutically acceptable salts by reacting the free acid form of the compound with a pharmaceutically acceptable inorganic or organic base, including, but not limited to organic bases such as ethanolamine, diethanolamine, triethanolamine, tromethamine, N-methylglucamine, and the like, or with an inorganic base such as aluminum hydroxide, calcium hydroxide, potassium hydroxide, sodium carbonate, sodium hydroxide, and the like.

It should be understood that a reference to a pharmaceutically acceptable salt includes the solvent addition forms or crystal forms thereof, particularly solvates or polymorphs. Solvates contain either stoichiometric or non-stoichiometric amounts of a solvent, and are optionally formed during the process of crystallization with pharmaceutically acceptable solvents such as water, ethanol, and the like. Hydrates are formed when the solvent is water, or alcoholates are formed when the solvent is alcohol. Solvates of compounds of Formula (I) are conveniently prepared or formed during the processes described herein. By way of example only, hydrates of compounds of Formula (I) are conveniently prepared by recrystallization from an aqueous/organic solvent mixture, using organic solvents including, but not limited to, dioxane, tetrahydrofuran, ethanol, or methanol. In addition, the compounds provided herein can exist in unsolvated as well as solvated forms. In general, the solvated forms are considered equivalent to the unsolvated forms for the purposes of the compounds and methods provided herein.

In yet other embodiments, the compounds of Formula (I) are prepared in various forms, including but not limited to, amorphous forms, milled forms and nano-particulate forms. In addition, compounds of Formula (I) include crystalline forms, also known as polymorphs. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

In some embodiments, compounds of Formula (I) are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of Formula (I) which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some situations, they are easier to administer than the parent drug. In certain embodiments, the prodrug of a compound described herein is bioavailable by oral administration whereas the parent is not. Furthermore, in some embodiments, the prodrug of a compound described herein has improved solubility in pharmaceutical compositions over the parent drug.

In other embodiments, prodrugs are designed as reversible drug derivatives, for use as modifiers to enhance drug transport to site-specific tissues. In specific embodiments, the design of prodrugs to date is to increase the effective water solubility of the therapeutic compound for targeting to regions where water is the principal solvent. Fedorak et al., *Am. J. Physiol.,* 269:G210-218 (1995); McLoed et al., *Gastroenterol,* 106:405-413 (1994); Hochhaus et al., *Biomed. Chrom.,* 6:283-286 (1992); J. Larsen and H. Bundgaard, *Int. J. Pharmaceutics,* 37, 87 (1987); J. Larsen et al., *Int. J. Pharmaceutics,* 47, 103 (1988); Sinkula et al. *J. Pharm. Sci.,* 64:181-210 (1975); T. Higuchi and V. Stella, *Prodrugs as Novel Delivery Systems,* Vol. 14 of the A. C. S. Symposium Series; and Edward B. Roche, *Bioreversible Carriers in Drug Design,* American Pharmaceutical Association and Pergamon Press, 1987.

In some embodiments, sites on the aromatic ring portion of compounds of Formula (I) are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

In yet another embodiment, the compounds of Formula (I) possess one or more stereocenters and each center exists independently in either the R or S configuration. The compounds presented herein include all diastereomeric, enantiomeric, and epimeric forms as well as the appropriate mixtures thereof. In certain embodiments, compounds of Formula (I) are prepared as their individual stereoisomers by reacting a racemic mixture of the compound with an optically active resolving agent to form a pair of diastereoisomeric compounds, separating the diastereomers and recovering the optically pure enantiomers. In some embodiments, resolution of enantiomers is carried out using covalent diastereomeric derivatives of the compounds described herein. In other embodiments, dissociable complexes are utilized (e.g., crystalline diastereomeric salts). Diastereomers have distinct physical properties (e.g., melting points, boiling points, solubilities, reactivity, etc.) and are, in specific embodiments, separated by taking advantage of these dissimilarities. In these embodiments, the diastereomers are separated by chiral chromatography or by separation/resolution techniques based upon differences in solubility. The optically pure enantiomer is then recovered, along with the resolving agent, by any practical means that does not result in racemization. Jean Jacques, Andre Collet, Samuel H. Wilen, "Enantiomers, Racemates and Resolutions", John Wiley And Sons, Inc., 1981.

Additionally, in certain embodiments, the compounds provided herein exist as geometric isomers. The compounds and methods provided herein include all cis, trans, syn, anti, entgegen (E), and zusammen (Z) isomers as well as the appropriate mixtures thereof. In some embodiments, the compounds described herein exist as tautomers. All tautomers are intended to be within the scope of the molecular formulas described herein. In additional embodiments of the compounds and methods provided herein, mixtures of enantiomers and/or diastereoisomers, resulting from a single preparative step, combination, or interconversion are envisioned.

Certain Terminology

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. In this application, the use of "or" or "and" means "and/or" unless stated otherwise.

Furthermore, use of the term "including" as well as other forms, such as "include", "includes," and "included," is not limiting.

"Compound of Formula (I)" refers to compound of Formula (I), compound of Formula (Ia), compound of Formula (Ib), compound of Formula (Ic), compound of Formula (Id).

An "alkyl" group refers to an aliphatic hydrocarbon group. The alkyl moiety may be a saturated alkyl group (which means that it does not contain any units of unsaturation, e.g. carbon-carbon double bonds or carbon-carbon triple bonds) or the alkyl moiety may be an unsaturated alkyl group (which means that it contains at least one unit of unsaturation). The alkyl moiety, whether saturated or unsaturated, may be branched, or straight chain.

The "alkyl" moiety may have 1 to 8 carbon atoms (whenever it appears herein, a numerical range such as "1 to 8" refers to each integer in the given range; e.g., "1 to 8 carbon atoms" means that the alkyl group may consist of 1 carbon atom, 2 carbon atoms, 3 carbon atoms, etc., up to and including 8 carbon atoms, although the present definition also covers the occurrence of the term "alkyl" where no numerical range is designated). The alkyl group of the compounds described herein may be designated as "$C_1$-$C_6$ alkyl" or similar designations. By way of example only, "$C_1$-$C_6$ alkyl" indicates that there are one, two, three, four, five, or six carbon atoms in the alkyl chain. Typical alkyl groups include, but are in no way limited to, methyl, ethyl, propyl, isopropyl, butyl, isobutyl, tertiary butyl, pentyl, hexyl, and the like. The term "lower alkyl" is similarly used for groups having from 1 to 4 carbon atoms.

The term "aralkyl" is refers to -alkyl-aryl, where alkyl and aryl are as defined herein.

The term "alicyclic" refers to a cyclic aliphatic group.

The term "aliphatic" takes its normal meaning in the art and includes non-aromatic groups such as alkanes, alkenes and alkynes and substituted derivatives thereof.

An "alkoxy" group refers to a (alkyl)O— group, where alkyl is as defined herein.

The term "alkylamine" refers to the —N(alkyl)$_x$H$_y$ group, where x and y are selected from the group x=1, y=1 and x=2, y=0. In some embodiments, when x=2 and y=0, the alkyl groups taken together with the nitrogen atom to which they are attached form a cyclic ring system.

An "amide" is a chemical moiety with formula —C(=O)NHR or —NHC(=O)R, where R is selected from the group consisting of alkyl, cycloalkyl, aryl, heteroaryl (bonded through a ring carbon) and heteroalicyclic (bonded through a ring carbon). An amide may be an amino acid or a peptide molecule attached to a compound of Formula (I), thereby forming a prodrug. Any amine, or carboxyl side chain on the compounds described herein is optionally amidified, as desired. See, e.g., Greene and Wuts, Protective Groups in Organic Synthesis, 3$^{rd}$ Ed., John Wiley & Sons, New York, N.Y., 1999, is incorporated herein by reference for such disclosure.

The term "aromatic" refers to a planar ring having a delocalized π-electron system containing 4n+2 π electrons, where n is an integer. Aromatic rings can be formed from five, six, seven, eight, nine, ten, or more than ten atoms. Aromatics are optionally substituted. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" refers to a ring or ring system where the atoms forming the backbone of the ring are all carbon atoms. The term thus distinguishes carbocyclic from heterocyclic rings in which the ring backbone contains at least one atom which is different from carbon.

As used herein, the term "aryl" refers to an aromatic ring wherein each of the atoms forming the ring is a carbon atom. Aryl rings are formed by five, six, seven, eight, nine, or more than nine carbon atoms. Aryl groups are optionally substituted. In one aspect, an aryl is a phenyl or a naphthalenyl. Depending on the structure, an aryl group can be a monoradical or a diradical (i.e., an arylene group). In one aspect, an aryl is a $C_6$-$C_{10}$aryl. The term "cycloalkyl" refers to a monocyclic or polycyclic aliphatic, non-aromatic radical, wherein each of the atoms forming the ring (i.e. skeletal atoms) is a carbon atom. Cycloalkyls may be saturated, or partially unsaturated. Cycloalkyls may be fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclohexyl, cycloheptyl, and cyclooctyl. Cycloalkyl groups may be substituted or unsubstituted.

As used herein, the term "carbohydrate derivative" refers to a compound of general formula $C_x(H_2O)_y$ or a derivative thereof. Preferably, the carbohydrate is a mono-, di- or tri-saccharide. Monosaccharides can exist as either straight chain or ring-shaped molecules and are classified according to the number of carbon atoms they possess; trioses have three carbons, tetroses four, pentoses five and hexoses six. Each of these subgroups may be further divided into aldoses and ketoses, depending on whether the molecule contains an aldehyde group (—CHO) or a ketone group (C=O). Typical examples of monosaccharides include glucose, fructose, and galactose. Disaccharides consist of two linked monosaccharide molecules, and include for example, maltose and lactose. Trisaccharides consist of three linked monosaccharide molecules.

The term "ester" refers to a chemical moiety with formula —COOR, where R is selected from the group consisting of alkyl, cycloalkyl, aryl, heteroaryl (bonded through a ring carbon) and heteroalicyclic (bonded through a ring carbon). Any hydroxy, or carboxyl side chain on the compounds described herein is esterified, if desired. Examples of procedures and specific groups to make such esters are found in sources such as Greene and Wuts, Protective Groups in Organic Synthesis, 3$^{1d}$ Ed., John Wiley & Sons, New York, N.Y., 1999.

The term "halo" or, alternatively, "halogen" or "halide" means fluoro, chloro, bromo or iodo.

The term "haloalkyl" refers to an alkyl group in which one or more hydrogen atoms are replaced by one or more halide atoms. In one aspect, a haloalkyl is a $C_1$-$C_6$haloalkyl.

The term "fluoroalkyl" refers to a alkyl in which one or more hydrogen atoms are replaced by a fluorine atom. In one aspect, a fluoralkyl is a $C_1$-$C_6$fluoroalkyl.

The term "heteroalkyl" refers to an alkyl group in which one or more skeletal atoms of the alkyl are selected from an atom other than carbon, e.g., oxygen, nitrogen, sulfur, phosphorus or combinations thereof. In one aspect, a heteroalkyl is a $C_1$-$C_6$ heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 4 to 10 atoms in its ring system, and with the proviso that the any ring does not contain two adjacent O or S atoms. Non-aromatic heterocyclic groups (also known as heterocycloalkyls) include groups having only 3 atoms in their ring system, but aromatic heterocyclic groups must have at least 5 atoms in their ring system. The heterocyclic groups include benzo-fused ring systems. An example of a 3-membered heterocyclic group is aziridinyl. An example of a 4-membered heterocyclic group is azetidinyl. An example of a 5-membered heterocyclic group is thiazolyl. An example of a 6-membered heterocyclic group is pyridyl, and an example of a 10-membered heterocyclic group is quinolinyl. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups may be C-attached or N-attached where such is possible. For instance, a group derived from pyrrole may be pyrrol-1-yl (N-attached) or pyrrol-3-yl (C-attached). Further, a group derived from imidazole may be imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles may be substituted with one or two oxo (=O) moieties, such as pyrrolidin-2-one.

The terms "heteroaryl" or, alternatively, "heteroaromatic" refers to an aryl group that includes one or more ring heteroatoms selected from nitrogen, oxygen and sulfur. Preferred heteroaryl groups include indole, azaindole, pyrrole, pyrazole, pyrimidine, pyrazine, pyridine, quinoline, thiophene and furan. In one aspect, a heteroaryl contains 0-3 N atoms. In another aspect, a heteroaryl contains 0-3 N atoms, 0-1 O atoms, and 0-1 S atoms. In another aspect, a heteroaryl is a monocyclic or bicyclic heteroaryl.

A "heterocycloalkyl", "heteroalicyclic" or "non-aromatic heterocycle" refers to a cycloalkyl group that includes at least one heteroatom selected from nitrogen, oxygen and sulfur. The radicals may be fused with an aryl or heteroaryl. In some embodiments, the heterocycloalkyl is selected from oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, and indolinyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In one aspect, a heterocycloalkyl contains 0-2 N atoms. In another aspect, a heterocycloalkyl contains 0-2 N atoms, 0-2 O atoms or 0-1 S atoms.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "membered ring" includes any cyclic structure. The term "membered" is meant to denote the number of skeletal atoms that constitute the ring. Thus, for example, cyclohexyl, pyridinyl, pyranyl and thiopyranyl are 6-membered rings and cyclopentyl, pyrrolyl, furanyl, and thienyl are 5-membered rings.

The term "moiety" refers to a specific segment or functional group of a molecule. Chemical moieties are often recognized chemical entities embedded in or appended to a molecule.

The term "optionally substituted" or "substituted" means that the referenced group may be substituted with one or more additional group(s) individually and independently selected from alkyl, cycloalkyl, aryl, heteroaryl, heteroalicyclic, hydroxy, alkoxy, aryloxy, alkylthio, arylthio, alkylsulfoxide, arylsulfoxide, alkylsulfone, arylsulfone, cyano, halo, carbonyl, thiocarbonyl, nitro, haloalkyl, fluoroalkyl, and amino, including mono- and di-substituted amino groups, and the protected derivatives thereof. By way of example an optional substituents may be halide, —CN, —NO$_2$, or L$_s$R$_s$, wherein each L$_s$ is independently selected from a bond, —O—, —C(=O)—, —C(=O)O—, —S—, —S(=O)—, —S(=O)$_2$—, —NH—, —NHC(=O)—, —C(=O)NH—, S(=O)$_2$NH—, —NHS(=O)$_2$, —OC(=O)NH—, —NHC(=O)O—, or —(C$_1$-C$_6$ alkyl)-; and each R$_s$ is selected from H, alkyl, fluoroalkyl, heteroalkyl, cycloalkyl, aryl, heteroaryl, or heterocycloalkyl. The protecting groups that may form the protective derivatives of the above substituents may be found in sources such as Greene and Wuts, above. In one aspect, optional substituents are selected from halogen, CF$_3$, OH, CN, NO$_2$, SO$_3$H, SO$_2$NH$_2$, SO$_2$Me, NH$_2$, COOH, CONH$_2$, alkoxy, —N(CH$_3$)$_2$, and alkyl.

In certain embodiments, the compounds presented herein possess one or more stereocenters and each center independently exists in either the R or S configuration. The compounds presented herein include all diastereomeric, enantiomeric, and epimeric forms as well as the appropriate mixtures thereof. Stereoisomers are obtained, if desired, by methods such as, the separation of stereoisomers by chiral chromatographic columns.

The methods and formulations described herein include the use of N-oxides (if appropriate), crystalline forms (also known as polymorphs), or pharmaceutically acceptable salts of compounds having the structure of Formula (I), as well as active metabolites of these compounds having the same type of activity. In some situations, compounds may exist as tautomers. All tautomers are included within the scope of the compounds presented herein. In specific embodiments, the compounds described herein exist in solvated forms with pharmaceutically acceptable solvents such as water, ethanol, and the like. In other embodiments, the compounds described herein exist in unsolvated form.

Certain Pharmaceutical and Medical Terminology

The term "acceptable" with respect to a formulation, composition or ingredient, as used herein, means having no persistent detrimental effect on the general health of the subject being treated.

The term "kinase-dependent", as used herein, refers to conditions or disorders that would not occur, or would not occur to the same extent, in the absence of a kinase enzyme.

The term "kinase-mediated", as used herein, refers to refers to conditions or disorders that might occur in the absence of kinase enzyme but can occur in the presence of kinase enzyme.

The term "asthma" as used herein refers to any disorder of the lungs characterized by variations in pulmonary gas flow associated with airway constriction of whatever cause (intrinsic, extrinsic, or both; allergic or non-allergic). The term asthma may be used with one or more adjectives to indicate cause.

The term "bone disease," as used herein, refers to a disease or condition of the bone, including, but not limited to, inappropriate bone remodeling, loss or gain, osteopenia, osteomalacia, osteofibrosis, and Paget's disease.

The term "cardiovascular disease," as used herein refers to diseases affecting the heart or blood vessels or both, including but not limited to: arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumaticshock; hypertension, valvular heart disease, heart failure, abnormal blood pressure; shock; vasoconstriction (including that associated with migraines); vascular abnormality, inflammation, insufficiency limited to a single organ or tissue.

The term "cancer," as used herein refers to an abnormal growth of cells which tend to proliferate in an uncontrolled way and, in some cases, to metastasize (spread). The types of cancer include, but are not limited to, solid tumors (such as those of the bladder, bowel, brain, breast, endometrium, heart, kidney, lung, lymphatic tissue (lymphoma), ovary, pancreas or other endocrine organ (thyroid), prostate, skin (melanoma) or hematological tumors (such as the leukemias).

The terms "co-administration" or the like, as used herein, are meant to encompass administration of the selected therapeutic agents to a single patient, and are intended to include treatment regimens in which the agents are administered by the same or different route of administration or at the same or different time.

The term "dermatological disorder," as used herein refers to a skin disorder. Such dermatological disorders include, but are not limited to, proliferative or inflammatory disorders of the skin such as, atopic dermatitis, bullous disorders, collagenoses, contact dermatitis eczema, Kawasaki Disease, rosacea, Sjogren-Larsso Syndrome, urticaria.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "iatrogenic" means a condition, disorder, or disease created or worsened by medical or surgical therapy.

The term "inflammatory disorders" refers to those diseases or conditions that are characterized by one or more of the signs of pain, heat, redness, swelling, and loss of function (temporary or permanent). Inflammation takes many forms and includes, but is not limited to, inflammation that is one or more of the following: acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative. Inflammatory disorders further include, without being limited to those affecting the blood vessels (polyarteritis, temporal arteritis); joints (arthritis: crystalline, osteo-, psoriatic, reactive, rheumatoid, Reiter's); gastrointestinal tract (colitis); skin (dermatitis); or multiple organs and tissues (systemic lupus erythematosus).

The term "immunological disorders" refers to those diseases or conditions that are characterized by inappropriate or deleterious response to an endogenous or exogenous antigen that may result in cellular dysfunction or destruction and consequently dysfunction or destruction of an organ or tissue and which may or may not be accompanied by signs or symptoms of inflammation.

The term "ARDS," as used herein, refers to a disease or condition of the lung, called Acute Respiratory Distress Syndrome, which is a fulminant lung condition in which trauma to the lungs leads to inflammation of the lungs, accumulation of fluid in the alveolar air sacs, low blood oxygen, and respiratory distress.

The term "Septic or Sepsis," as used herein refers to diseases a potentially serious medical condition that is characterized by a whole-body inflammatory state and the presence of a known or suspected infection.

The term "Rheumatoic Rheumatoid Arthritis," as used herein refers to a chronic, systemic inflammatory disorder that may affect many tissues and organs, but principally attacks synovial joints.

The terms "kit" and "article of manufacture" are used as synonyms.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

The terms "neurogenerative disease" or "nervous system disorder," as used herein, refers to conditions that alter the structure or function of the brain, spinal cord or peripheral nervous system, including but not limited to Alzheimer's Disease, cerebral edema, cerebral ischemia, multiple sclerosis, neuropathies, Parkinson's Disease, those found after blunt or surgical trauma (including post-surgical cognitive dysfunction and spinal cord or brain stem injury), as well as the neurological aspects of disorders such as degenerative disk disease and sciatica. The acronym "CNS" refers to disorders of the central nervous system, i.e., brain and spinal cord.

The term "subject" or "patient" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment, the mammal is a human.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

As used herein, amelioration of the symptoms of a particular disease, disorder or condition by administration of a particular compound or pharmaceutical composition refers to any lessening of severity, delay in onset, slowing of progression, or shortening of duration, whether permanent or temporary, lasting or transient that can be attributed to or associated with administration of the compound or composition.

Therapeutic Use

In one aspect, the compounds of Formula (I) inhibit one or more protein kinase(s). In one aspect, the compounds of Formula (I) demonstrate anti-proliferative activity and are useful in the treatment of proliferative disorders. In one aspect, the compounds of Formula (I) demonstrate anti-proliferative activity and are useful in the treatment of proliferative disorders such as cancers, leukaemias and other disorders associated with uncontrolled cellular proliferation such as psoriasis and restenosis.

In one aspect, an anti-proliferative effect within the scope of the present disclosure is the ability to inhibit cell proliferation in an in vitro whole cell assay. In one aspect, the in vitro whole cell assay uses any one of the cell lines selected from A549, A2780, HepG2, HCT-116, HeLa, HT29, MCF-7, NCI-H460, and Saos-2. In one aspect, an anti-proliferative effect within the scope of the present disclosure is the ability to inhibit at least one CDK enzyme, such as CDK1, CDK2, CDK4, CDK5, CDK6, CDK7, CDK8, CDK9, CDK11, or other protein kinases; or inhibition of the interaction between HDM2 and p53 in an appropriate assay. These assays, including methods for their performance, are known in the art and/or are described in more detail in the accompanying Examples.

In one aspect, the compounds of Formula (I) are used in the treatment of proliferative disorders. In a further aspect, there is provided the use of one or more compounds of Formula (I) in the manufacture of a medicament for treating proliferative disorders. In one aspect, the proliferative disorder is a cancer or leukaemia. The term proliferative disorder is used herein in a broad sense to include any disorder that requires control of the cell cycle, for example cardiovascular disorders, auto-immune disorders, dermatological disorders, inflammatory, fungal, parasitic disorders, emphysema and alopecia. In one aspect, the compounds of Formula (I) induce apoptosis or maintain stasis in these disorders within the appropriate cells as required.

In one aspect, cardiovascular disorders include, but are not limited to, restenosis and cardiomyopathy. In one aspect, auto-immune disorders include, but are not limited to, glomerulonephritis and rheumatoid arthritis. In one aspect, dermatological disorders include, but are not limited to, psoriasis. In one aspect, parasitic disorders include, but are not limited to, malaria.

In one aspect, the compounds of Formula (I) are used in the treatment of a disease, disorder, or condition mediated by one or more protein kinase selected from a CDK, aurora kinase, GSK, PLK and one of Tyrosine kinases. In one aspect, the compounds of Formula (I) inhibit such protein kinases.

In one aspect, the compounds of Formula (I) are used in the treatment of a disease, disorder, or condition mediated by one or more protein kinase selected from a CDK (such as CDK1, CDK2, CDK4, CDK5, CDK6, CDK7, CDK8, CDK9, CDK11, or other protein kinases), aurora kinase, GSK, PLK and one of Tyrosine kinases. In one aspect, the compounds of Formula (I) inhibit such protein kinases, preferably CDK9.

In one aspect, the compounds of Formula (I) inhibit any of the steps or stages in the cell cycle, for example, formation of the nuclear envelope, exit from the quiescent phase of the cell cycle (G0), G1 progression, chromosome decondensation, nuclear envelope breakdown, START, initiation of DNA replication, progression of DNA replication, termination of DNA replication, centrosome duplication, G2 progression, activation of mitotic or meiotic functions, chromosome condensation, centrosome separation, microtubule nucleation, spindle formation and function, interactions with microtubule motor proteins, chromatid separation and segregation, inactivation of mitotic functions, formation of contractile ring, and cytokinesis functions. In particular, the compounds of Formula (I) influence certain gene functions such as chromatin binding, formation of replication complexes, replication licensing, phosphorylation or other secondary modification activity, proteolytic degradation, microtubule binding, actin binding, septin binding, microtubule organising centre nucleation activity and binding to components of cell cycle signalling pathways.

In one embodiment, compounds of Formula (I) are useful in the treatment of a proliferative disorder, disease or condition mediated by at least one of a CDK, Auora kinase and/or PLK. In one aspect, the proliferative disorder, disease or condition mediated by at least one of a CDK, Auora kinase and/or PLK include, but are not limited to cancers, leukaemias and other disorders associated with uncontrolled cellular proliferation such as psoriasis and restenosis, a viral disorder, a cardiovascular disease, a CNS disorder, an autoimmune disease, a bone disease, a hormone-related disease, a metabolic disorder, stroke, alopecia, an inflammatory disease or an infectious disease.

In one aspect, the compounds of Formula (I) inhibit one or more of the host cell kinases involved in cell proliferation, viral replication, a cardiovascular disorder, neurodegeneration, autoimmunity, a metabolic disorder, stroke, alopecia, an inflammatory disease or an infectious disease.

A proliferative disorder requires treatment of a susceptible neoplasm and may be selected from the group consisting of chronic lymphocytic leukaemia, lymphoma, leukaemia, breast cancer, lung cancer, prostate cancer, colon cancer, melanoma, pancreatic cancer, ovarian cancer, squamous carcinoma, carcinoma of head and neck, endometrial cancer, and aesophageal carcinoma.

In one aspect, the compounds, compositions and methods provided herein are useful for the treatment and prevention of cancer including solid tumors such as skin, breast, brain, cervical carcinomas, testicular carcinomas, etc. In one aspect, compounds described herein are useful for treating cancer. In one aspect, cancers include, but are not limited to:

Cardiac cancers, such as, but not limited to, sarcoma (angiosarcoma, fibrosarcoma, rhabdomyosarcoma, liposarcoma), myxoma, rhabdomyoma, fibroma, lipoma and teratoma;

Lung cancers, such as, but not limited to, bronchogenic carcinoma (squamous cell, undifferentiated small cell, undifferentiated large cell, non-small cell, adenocarcinoma), alveolar (bronchiolar) carcinoma, bronchial adenoma, sarcoma, lymphoma, chondromatous hamartoma, mesothelioma;

Gastrointestinal cancers, such as, but not limited to: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), rectal, colorectal and colon;

Genitourinary tract cancers, such as, but not limited to: kidney (adenocarcinoma, Wilm's tumor [nephroblastoma], lymphoma, leukemia, papillary renal carcinoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver cancers, such as, but not limited to: hepatoma (hepatocellular carcinoma), cholangiocarcinoma, hepatoblastoma, angiosarcoma, hepatocellular adenoma, hemangioma;

Bone cancers, such as, but not limited to: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

Nervous system cancers, such as, but not limited to: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma);

Gynecological cancers, such as, but not limited to: uterus (endometrial carcinoma), cervix (cervical carcinoma, pretumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma, vagina (clear cell carcinoma, squamous cell carcinoma, botryoid sarcoma (embryonal rhabdomyosarcoma), fallopian tubes (carcinoma);

Hematologic cancers, such as, but not limited to: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma];

Skin cancers, such as, but not limited to: malignant melanoma, basal cell carcinoma, squamous cell carcinoma, head and neck squamous cell carcinomas, Karposi's sarcoma, moles dysplastic nevi, lipoma, angioma, dermatofibroma, keloids, psoriasis; and Adrenal glands: neuroblastoma.

The term "cancerous cell" as provided herein, includes a cell afflicted by any one of the above-identified conditions.

In another embodiment, compound described herein are useful for treating or preventing cancer selected from: head and neck squamous cell carcinomas, histiocytic lymphoma, lung adenocarcinoma, small cell lung cancer, non-small cell lung cancer, pancreatic cancer, papillary renal carcinoma, liver cancer, gastric cancer, colon cancer, multiple myeloma, glioblastomas and breast carcinoma.

In another embodiment, compounds described herein are useful for the prevention or modulation of the metastases of cancer cells and cancer. In yet another embodiment, compounds described herein are useful to prevent or modulate the metastases of ovarian cancer, childhood hepatocellular carcinoma, metastatic head and neck squamous cell carcinomas, gastric cancers, breast cancer, colorectal cancer, cervical cancer, lung cancer, nasopharyngeal cancer, pancreatic cancer, glioblastoma and sarcomas.

A further embodiment relates to the use of compounds of Formula (I) described herein, or pharmaceutically acceptable salts thereof, in the manufacture of a medicament capable of treating a viral disorder mediated by one or more of the host cell CDKs involved in viral replication. In one aspect, the one or more CDKs are selected from among CDK1, CDK2, CDK4, CDK7, CDK8, CDK9 and CDK11.

Assays for determining CDK activity are described in more detail in the accompanying examples. Using such enzymes assays it may be determined whether a compound is anti-viral in the context of the present invention.

In one aspect, compounds of Formula (I), or pharmaceutical compositions comprising compounds of Formula (I) are used in the treatment of viral disorders. In one aspect, the viral disorder is selected from among human cytomegalovirus (HCMV), herpes simplex virus type 1 (HSV-1), human immunodeficiency virus type 1 (HIV-1), and varicella zoster virus (VZV). Typically such disorder is CDK dependent or sensitive. CDK dependent disorders are associated with an above normal level of activity of one or more CDK enzymes. In one aspect, such disorders are typically associated with an abnormal level of activity of CDK1, CDK2, CDK4, CDK6, CDK7, CDK8, CDK9 and/or CDK11.

A CDK sensitive disorder is a disorder in which an aberration in the CDK level is not the primary cause, but is downstream of the primary metabolic aberration. In such scenarios, CDK1, CDK2, CDK4, CDK6, CDK7, CDK8 CDK9 and/or CDK11 can be said to be part of the sensitive metabolic pathway and inhibitors of one or more of these CDKs are therefore useful in treating such disorders.

In one aspect, for use in the treatment of viral disorders, the compound of Formula (I) is capable of inhibiting one or more CDKs selected from among CDK2, CDK7, and CDK9.

In another aspect, compounds of Formula (I) are used in the treatment of cardiovascular diseases mediated by one or more CDKs. A cardiovascular disease may be selected from the group consisting of ischaemic heart disease (also known as myocardial infarction or angina), hypertension, heart failure, restenosis and cardiomyopathy.

Cardiac hypertrophy is characterized by global increases in mRNA and protein synthesis. CDK9 activity has been demonstrated to be necessary for hypertrophy in cardiomyocytes. Heart-specific activation of CDK9 by cyclin T1 was found to provoke hypertrophy. In one aspect, compounds of Formula (I) inhibit one or more CDKs and are therefore useful in the prevention and treatment of cardiac hypertrophy.

Yet another embodiment relates to the use of a compound of Formula (I) in the treatment of neurodegenerative disorders mediated by one or more GSKs or CDKs. In one aspect, the neurodegenerative disorder is Alzheimer's disease.

The appearances of Paired Helical Filaments, associated with Alzheimer's disease, are caused by the hyperphosphorylation of Tau protein by CDK5-p25. In one aspect, compounds of Formula (I) inhibit CDK5 and are useful in the prevention and treatment of neurodegenerative disorders.

Tau is a GSK-3 substrate which has been implicated in the etiology of Alzheimer's disease. In healthy nerve cells, Tau co-assembles with tubulin into microtubules. However, in Alzheimer's disease, tau forms large tangles of filaments, which disrupt the microtubule structures in the nerve cell, thereby impairing the transport of nutrients as well as the transmission of neuronal messages. In one aspect, GSK3 inhibitors prevent and/or reverse the abnormal hyperphosphorylation of the microtubule-associated protein tau that is an invariant feature of Alzheimer's disease and a number of other neurodegenerative diseases, such as progressive supranuclear palsy, corticobasal degeneration and Pick's disease. Mutations in the tau gene cause inherited forms of frontotemporal dementia, further underscoring the relevance of tau protein dysfunction for the neurodegenerative process.

In one aspect, compounds of Formula (I) are used in the treatment a metabolic disorder mediated by one or more GSKs. Metabolic disorders include Type II diabetes (non insulin dependent diabetes mellitus) and diabetic neuropathy. In one aspect, compounds of Formula (I) inhibit GSK-3, which is implicated in Type II diabetes.

GSK3 is one of several protein kinases that phosphorylate glycogen synthase (GS) and is involved in the stimulation of glycogen synthesis by insulin in skeletal muscle. GSK3's action on GS thus results in the latter's deactivation and thus suppression of the conversion of glucose into glycogen in muscles. Type II diabetes (non-insulin dependent diabetes mellitus) is a multi-factorial disease. Hyperglycaemia is due to insulin resistance in the liver, muscles, and other tissues, coupled with impaired secretion of insulin. Skeletal muscle is the main site for insulin-stimulated glucose uptake, there it is either removed from circulation or converted to glycogen. Muscle glycogen deposition is the main determinant in glucose homeostasis and type II diabetics have defective muscle glycogen storage. There is evidence that an increase in GSK3 activity is important in type II diabetes.

In one aspect, compounds of Formula (I) are used in the treatment of bipolar disorder mediated by one or more kinases.

In another aspect, compounds of Formula (I) are used for treating a stroke mediated by one or more GSKs.

Reducing neuronal apoptosis is an important therapeutic goal in the context of head trauma, stroke, epilepsy, and motor neuron disease. GSK3 as a pro-apoptotic factor in neuronal cells makes this protein kinase an attractive therapeutic target for the design of inhibitory drugs to treat these diseases.

In one aspect, compounds of Formula (I) are used in the treatment of alopecia mediated by one or more GSKs.

In one aspect, the ectopic application of GSK3 inhibitors is therapeutically useful in the treatment of baldness and in restoring hair growth following chemotherapy-induced alopecia.

In one aspect, described herein is a method of treating a disease, disorder and/or condition mediated by one or more enzymes selected from a CDK, aurora kinase, GSK, PLK or tyrosine kinase enzyme as hereinbefore described.

In one aspect, such condition is a GSK3-dependent disorder, said method comprising administering to a subject in need thereof, a compound of Formula (I) in an amount sufficient to inhibit GSK3. In one aspect, the compound of Formula (I) is administered in an amount sufficient to inhibit GSK3β.

In one aspect, described herein is a method of treating a PLK-dependent disease, disorder and/or condition, said method comprising administering to a subject in need thereof, a compound of the Formula (I) in an amount sufficient to inhibit a PLK. In one aspect, human PLKs regulate fundamental aspects of mitosis. Both PLK1 and PLK2 may have additional post-mitotic functions. Deregulated PLK expressions result in cell cycle arrest and apoptosis. Compounds of Formula (I) are used in treating PLK-mediated diseases, disorders and/or conditions. In one aspect, the PLK-mediated diseases, disorders and/or conditions include proliferative disorders.

In one aspect, the compounds of Formula (I) inhibit one or more PLK enzymes selected from PLK1, PLK2, PLK3 and PLK4

In another embodiment, described herein is a method of treating an aurora kinase-dependent disease, disorder and/or condition, said method comprising administering to a subject in need thereof, a compound of Formula (I).

In one aspect, the compound of Formula (I) inhibits one or more aurora kinases selected from among aurora kinase A, aurora kinase B or aurora kinase C.

In another embodiment, described herein is a method of treating a tyrosine kinase-dependent disorder, said method comprising administering to a subject in need thereof, a compound of Formula (I) in an amount sufficient to inhibit a tyrosine kinase.

In one aspect, compounds of Formula (I) are administered to a subject in an amount sufficient to inhibit at least one protein kinase selected from BCR-ABL, IKK, FLT3, JAK, LCK, PDGF, Src, and VEGF.

In some embodiments, described herein is a method of selectively treating a protein kinase-dependent disorder, said method comprising administering to a subject in need thereof, a compound of the invention or a pharmaceutically acceptable salt thereof, as defined above in an amount sufficient to inhibit a selected protein kinase. In one aspect, said method comprises contacting said protein kinase with a compound described herein.

In some embodiments, the compound of Formula (I) is administered in an amount sufficient to inhibit at least one of a CDK, GSK, aurora kinase, or PLK, or a tyrosine kinase including, but not limiting to BCR-ABL, IKK, FLT3, JAK, LCK, PDGF, Src, or VEGF.

In some embodiments, the protein kinase is a CDK. In one aspect, the protein kinase is CDK1, CDK2, CDK3, CDK4, CDK5, CDK6, CDK7, CDK8, CDK9 or CDK11. In another aspect, the protein kinase is CDK1, CDK2, CDK7 or CDK9.

In one aspect, the compound of Formula (I) inhibits at least one CDK enzyme, preferably at least one of CDK1, CDK2, CDK7 and CDK9.

In one aspect, the compound of Formula (I) inhibits a CDK. In one aspect, the compound of Formula (I) inhibits a CDK selected from CDK1, CDK2, CDK7 and CDK9 at sub-micromolar $IC_{50}$ values, more preferably at $IC_{50}$ of less than 0.5 micromolar, more preferably less than 0.25 micromolar. In one aspect, the compound of Formula (I) inhibits CDK9 at $IC_{50}$ of less than 0.1 micromolar or less than 0.05 micromolar.

In some embodiments, the compound of Formula (I) demonstrates an antiproliferative effect in human cell lines, as measured by a standard 72 h MTT cytotoxicity assay. In some embodiments, the compound of Formula (I) exhibits an $IC_{50}$ value of less than 1 micromolar.

In a further aspect, there is provided a method of treating a proliferative disease or disorder, a viral disorder, a cardiovascular disease, a CNS disorder, an autoimmune disease, a metabolic disorder, stroke, alopecia, an inflammatory disease or an infectious disease, said method comprising administering to a subject in need thereof, a compound of Formula (I) as hereinbefore defined in an effective amount.

The use of a compound of the invention in the manufacture of a medicament as hereinbefore defined includes the use of the compound directly, or in any stage of the manufacture of such a medicament, or in vitro in a screening programme to identify further agents for the prevention or treatment of the hereinbefore defined diseases or conditions.

A further aspect relates to the use of a compound of Formula (I) or a pharmaceutically acceptable salt or solvate or physiologically hydrolysable, solubilising or immobilising derivative thereof, in an assay for identifying candidate compounds capable of treating one or more disorders or diseases as hereinbefore defined. Preferably a compound is of use in identifying candidate compounds capable of inhibiting a protein kinase, more preferably one or more of a CDK, aurora kinase, GSK, PLK or tyrosine kinase enzyme, most preferably CDK9.

Routes of Administration

Suitable routes of administration include, but are not limited to, oral, intravenous, rectal, aerosol, parenteral, ophthalmic, pulmonary, transmucosal, transdermal, vaginal, otic, nasal, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner, for example, via injection of the compound directly into an organ, often in a depot preparation or sustained release formulation. In specific embodiments, long acting formulations are administered by implantation (for example subcutaneously or intramuscularly) or by intramuscular injection. Furthermore, in other embodiments, the drug is delivered in a targeted drug delivery system, for example, in a liposome coated with organ-specific antibody. In such embodiments, the liposomes are targeted to and taken up selectively by the organ. In yet other embodiments, the compound as described herein is provided in the form of a rapid release formulation, in the form of an extended release formulation, or in the form of an intermediate release formulation. In yet other embodiments, the compound described herein is administered topically.

Kits/Articles of Manufacture

For use in the therapeutic applications described herein, kits and articles of manufacture are also described herein. Such kits can comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. The containers are formed from any acceptable material including, e.g., glass or plastic.

For example, the container(s) can comprise one or more compounds described herein, optionally in a composition or in combination with another agent as disclosed herein. The container(s) optionally have a sterile access port (for example the container can be an intravenous solution bag or a vial having a stopper pierceable by a hypodermic injection needle). Such kits optionally comprising a compound with an identifying description or label or instructions relating to its use in the methods described herein.

A kit will typically comprise one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. A set of instructions will also typically be included.

A label can be on or associated with the container. A label can be on a container when letters, numbers or other characters forming the label are attached, molded or etched into the container itself; a label can be associated with a container when it is present within a receptacle or carrier that also holds the container, e.g., as a package insert. A label can be used to indicate that the contents are to be used for a specific therapeutic application. The label can also indicate directions for use of the contents, such as in the methods described herein.

All of the features disclosed in this specification (including any accompanying claims, abstract and drawings), and/or all of the steps of any method or process so disclosed, may be combined in any combination, except combinations where at least some of such features and/or steps are mutually exclusive.

EXAMPLES

These examples are provided for illustrative purposes only and not to limit the scope of the claims provided herein.

General. $^1$H-NMR spectra were obtained using a Broker-400 spectrometer. Chemical shifts are reported in parts per million relative to internal tetramethylsilane standard. Coupling constants (J) are quoted to the nearest 0.1 Hz. The following abbreviations are used: s, singlet; d, doublet; t, triplet; q, quartet; qu, quintuplet; m, multiplet and br, broad. Mass spectra were obtained using a Waters 2795 single quadrupole mass spectrometer with electrospray ionization (ESI). Microwave assisted chemistry was carried out using CEM Discovery model (Biotage Ltd. UK). TLC (thin-layer chromatography) was performed using alumina plates coated with silica gel G60. Developed plates were air dried and analyzed under a UV lamp (254/365 nm). Silica gel (EM Kieselgel 60, 0.040-0.063 mm, Merck) or ISOLUTE prepacked columns was used for flash chromatography.

Example 1

3-(4-(1-Methyl-1H-indol-3-yl)pyrimidin-2-ylamino) phenol (Compound 1)

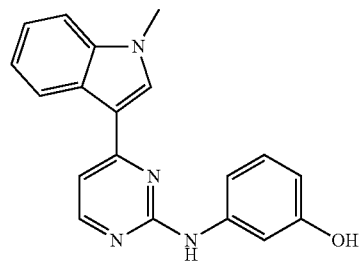

A mixture of 3-acetylindole (20 mmol) and N,N,-dimethylformamide demethylacetal (65 mmol) was heated to reflux for 48 hours. The excess amount of N,N,-dimethylformamide demethylacetal was removed in vacuo. The oil residue was precipitated by the addition of a minima amount of EtOAc. The solid was filtered and washed with EtOAc/PE to give (E)-3-(dimethylamino)-1-(1-methyl-1H-indol-3-yl)prop-2-en-1-one as orange powder. $^1$H-NMR (DMSO-d$_6$) δ: 2.97 (s, 6H, CH$_3$×2), 3.83 (s, 3H, CH$_3$), 2.85 (s, 3H, CH$_3$), 5.71 (d, 1H, J=12.8 Hz, CH), 7.14 (m, 1H, Ph-H), 7.21 (m, 1H, Ar—H), 7.46 (d, 1H, J=8.4 Hz, Ar—H), 7.53 (d, 1H, J=12.4 Hz, CH), 8.15 (s, 1H, Ar—H), 8.28 (d, 1H, J=8.0 Hz, Ar—H). MS (ESI$^+$) m/z 229.3037 (M+H)$^+$.

To a mixture of (E)-3-(dimethylamino)-1-(1-methyl-1H-indol-3-yl)prop-2-en-1-one (1.0 mmol, 0.21 g) in MeCN (3.5 mL) was added 1.0 mmol 1-(3-hydroxyphenyl)guanidine hydrogen chloride salt in the presence of NaOH (1.0 mmol). The mixture was irradiated at 150° C. for 20 minutes in microwave. The mixture was purified by chromatography using EtOAc/PE (1:1, v/v) to elute the titled product as a off-white solid. $^1$H-NMR (DMSO-d$_6$) δ: 3.89 (s, 3H, CH$_3$), 6.38 (m 1H, Ph-H), 7.07 (m, 1H, Ph-H), 7.19 (d, 1H, J=5.6 Hz, Pyrimidin-H), 7.25 (m, 1H, Ar—H), 7.38 (s, 1H, Ph-H), 7.53 (d, 1H, J=8.0 Hz, Ph-H), 8.32 (m, 2H, Ar—H and Pyrimidin-H), 8.64 (d, 1H, J=8.0 Hz, OH), 9.23 (s, 1H, Ar—H), 9.27 (s, 1H, Ar—H). MS (ESI$^+$) m/z 317.1311 (M+H)$^+$ The following compounds were prepared in an analogous manner:

Example 2

4-(4-(1-Methyl-1H-indol-3-yl)pyrimidin-2-ylamino)phenol (Compound 2)

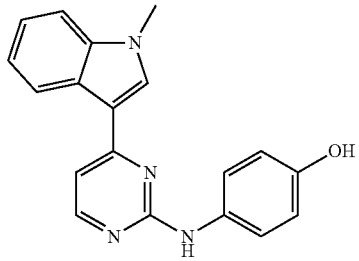

The compound was obtained by treatment of (E)-3-(dimethylamino)-1-(1-methyl-1H-indol-3-yl)prop-2-en-1-one with 1-(4-hydroxyphenyl)guanidine hydrochloride as white solid; $^1$H-NMR (DMSO-d$_6$) δ: 3.88 (s, 3H, CH$_3$), 6.74 (d, 1H, J=8.8 Hz, Ph-H), 7.10 (d, 2H, J=5.6 Hz, Pyrimidin-H), 7.17 (t, 1H, J=7.2 Hz, Ar—H), 7.28 (t, 1H, J=7.2 Hz, Ar—H), 7.53 (m, 3H, Ar—H), 8.26 (m, 2H, Ar—H and Pyrimidin-H), 8.58 (d, 1H, J=7.6 Hz, OH), 9.03 (s, 2H, Ph-H). MS (ESI$^+$) m/z 317.1351 (M+H)$^+$ Example 3

3-Chloro-4-(4-(1-methyl-1H-indol-3-yl)pyrimidin-2-ylamino)phenol (Compound 3)

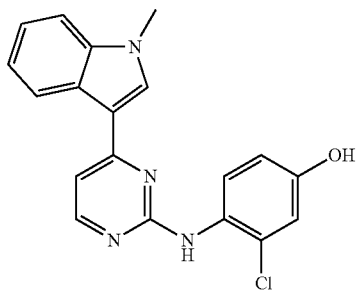

Obtained by treatment of (E)-3-(dimethylamino)-1-(1-methyl-1H-indol-3-yl)prop-2-en-1-one with 1-(2-chloro-4-hydroxyphenyl)guanidine hydrochloride as white solid; $^1$H-NMR (DMSO-d$_6$) δ: 3.85 (s, 3H, CH$_3$), 6.80 (dd, 1H, J=2.8, 8.4 Hz, Ph-H), 6.93 (d, 2H, J=2.8 Hz, Ar—H), 7.04 (t, 1H, J=7.2 Hz, Ar—H), 7.09 (d, 1H J=5.2 Hz, Pyrimidin-H), 7.22 (t, 1H, J=7.2 Hz, Ar—H), 7.45 (d, 1H, J=8.8 Hz, Ph-H), 7.48 (d, 1H, J=8.4 Hz, Ar—H), 8.20 (d, 1H, J=5.2 Hz, Pyrimidin-H), 8.23 (s, 1H, Ph-H), 8.26 (d, 1H, J=8.0 Hz, OH), 8.48 (s, 1H, Ar—H), 9.74 (s, 1H, NH). MS (ESI$^+$) m/z 351.1048 (M+H)$^+$ Example 4

4-(4-(1-Ethyl-1H-pyrrolo[2,3-b]pyridin-3-yl)pyrimidin-2-ylamino)phenol (Compound 12)

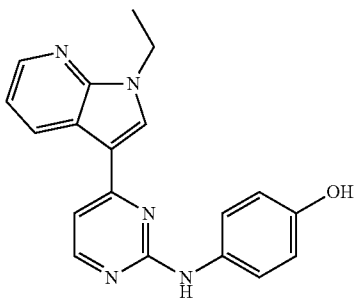

A solution of 1H-pyrrolo[2,3-b]pyridine (10 mmol, 1.18 g) in dry DMF (10 mL) was cooled on a an ice bath. NaH (130 mmol, 3.12 g) was added portion wise under N$_2$ atmosphere. After completion of the addition the reaction mixture was allowed to stir at room temperature for 45 minutes. Upon cooling at 0° C. iodoethane (30 mmol) was added and the reaction mixture was stirred at room temperature for 3 hours. Ice water was added. The mixture was diluted with diethyl ether and extracted with diethyl ether (4×30 mL). The organic layers were combined and washed with brine, dried on MgSO$_4$ and filtered. The solvent was evaporated to give brown oil which was purified by chromatography using EtOAc/PE to elute 1-ethyl-1H-pyrrolo[2,3-b]pyridine as light yellow oil. $^1$H-NMR (CD$_3$Cl) δ: 1.50 (t, 3H, J=7.6 Hz, CH$_3$), 4.37 (q, 2H, J=7.6 Hz, CH$_2$), 6.47 (d, 1H, J=3.6 Hz, Ar—H), 7.07 (m, 1H, Ar—H), 7.26 (d, 1H, J=3.6 Hz, Ar—H), 7.92 (d, 1H, J=8.0 Hz, Ar—H), 8.34 (d, 1H, J=4.8 Hz, Ar—H). MS (ESI$^+$) m/z 147.1001 (M+H)$^+$.

Above compound (8.4 mmol, 1.22 g) was added to stirred suspension of AlCl$_3$ (42 mmol) in dry CH$_2$Cl$_2$. After stirring at room temperature for 1 hour, acylchloride (42 mmol) was added dropwise. The reaction mixture was allowed to sire for further 1 hour at room temperature. Cooling on an ice bath methanol (40 mL) was added cautiously to quench the reaction. The solvent was evaporated in vacuo and the residue was purified by chromatography using EtOAc/MeOH (10:1, v/v) to give 1-(1-ethyl-1H-pyrrolo[2,3-b]pyridin-3-yl)ethanone as light yellow solid (0.69 g, 44% yield). MS (ESI+) m/z 189.0967 (M+H)+.

A mixture of 1-(1-ethyl-1H-pyrrolo[2,3-b]pyridin-3-yl) ethanone (3 mmol) and N,N-dimethylformamide dimethyal acetal (25 mmol) was microwaved at 150° C. for 15 minutes. The precipitate was filtered and washed with EtOAc. The filtrate was concentrated in vacuo. The resulting solid was collected by filtration and washed with EtOAc followed by diethyl ether to result in (E)-3-(dimethylamino)-1-(1-ethyl-1H-pyrrolo[2,3-b]pyridin-3-yl)prop-2-en-1-one. $^1$H-NMR (DMSO-d$_6$) δ: 1.43 (t, 3H, J=7.2 Hz, CH$_3$), 4.33 (q, 2H, J=7.6 Hz, CH$_2$), 5.77 (d, 1H, J=12.4 Hz, CH), 7.20 (q, 1H, J=4.8 Hz, Ar—H), 7.58 (d, 1H, J=12.4 Hz, CH), 8.29 (m, 1H, Ar—H), 8.41 (s, 1H, Ar—H), 8.56 (m, 1H, Ar—H). MS (ESI+) m/z 244.1222 (M+H)+.

A mixture of (E)-3-(dimethylamino)-1-(1-ethyl-1H-pyrrolo[2,3-b]pyridin-3-yl)prop-2-en-1-one (5 mmol) in 3 mL EtOH/MeOH (1:2, v/v) was treated with 1-(4-hydroxyphenyl)guanidine hydrochloride (5 mmol) and NaOH (10 mmol). The reaction mixture was microwaved at 150° C. for 25 minutes. The residue was purified by chromatography using EtOAc to elute the titled compound. Recrystallisation from EtOAc yielded white solid. $^1$H-NMR (DMSO-d$_6$) δ: 1.45 (t, 3H, J=7.2 Hz, CH$_3$), 4.37 (q, 2H, J=7.6 Hz, CH$_2$), 6.74 (d, 2H, J=8.8 Hz, Ph-H), 7.15 (d, 1H, J=5.2 Hz, Pyrimidin-H), 7.20 (q, 1H, J=4.8 Hz, Ar—H), 7.51 (d, 2H, J=8.8 Hz, Ph-H), 8.29 (d, 1H, J=5.2 Hz, Pyrimidin-H), 8.35 (m, 1H, Ar—H), 8.54 (s, 1H, Ar—H), 8.88 (d, 1H, J=6.8 Hz, OH), 9.04 (s, 1H, Ar—H), 9.10 (s, 1H, NH). MS (ESI+) m/z 322.1469 (M+H)+.

The following compounds were synthesized by an analogous route.

Example 5

3-(4-(1-Ethyl-1H-pyrrolo[2,3-b]pyridin-3-yl)pyrimidin-2-ylamino)phenol (Compound 13)

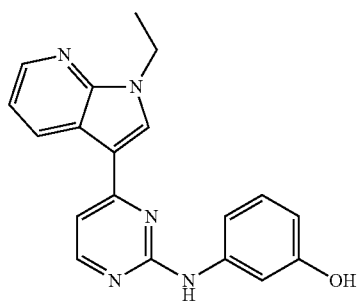

Prepared by treatment of (E)-3-(dimethylamino)-1-(1-ethyl-1H-pyrrolo[2,3-b]pyridin-3-yl)prop-2-en-1-one and 1-(3-hydroxyphenyl)guanidine hydrochloride. $^1$H-NMR (DMSO-d$_6$) δ: 1.18 (t, 3H, J=7.2 Hz, CH$_3$), 4.37 (q, 2H, J=7.2 Hz, CH$_2$), 6.40 (m, 1H, Ph-H), 7.08 (t, 1H, J=7.6 Hz, Ph-H), 7.18 (m, 1H, Ar—H), 7.24 (d, 1H, J=5.6 Hz, Pyrimidin-H), 7.37 (s, 1H, Ph-H), 8.36 (m, 2H, Pyrimidin-H and Ar—H), 8.59 (s, 1H, Ar—H), 9.00 (d, 1H, J=8.0 Hz, Ph-H), 9.24 (s, 1H, Ar—H), 9.33 (s, 1H, NH). MS (ESI+) m/z 332.1355 (M+H)+.

Example 6

4-(1-Ethyl-1H-pyrrolo[2,3-b]pyridin-3-yl)-N-(3-nitrophenyl)pyrimidin-2-amine (Compound 14)

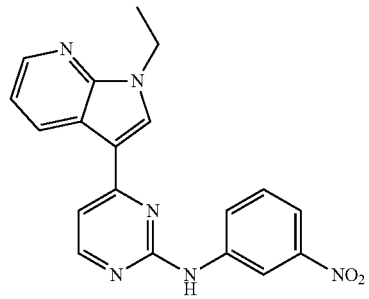

Prepared by treatment of (E)-3-(dimethylamino)-1-(1-ethyl-1H-pyrrolo[2,3-b]pyridin-3-yl)prop-2-en-1-one and 1-(3-nitrophenyl)guanidine hydrochloride. $^1$H-NMR (DMSO-d$_6$) δ: 1.49 (t, 3H, J=7.2 Hz, CH$_3$), 4.37 (q, 2H, J=7.6 Hz, CH$_2$), 7.26 (m, 1H, Ar—H), 7.39 (d, 1H, J=5.2 Hz, Pyrimidin-H), 7.61 (t, 1H, J=8.0 Hz, Ph-H), 7.83 (m, 1H, Ar—H), 8.12 (d, 1H, J=8.0 Hz, Ph-H), 8.38 (m, 1H, Ar—H), 8.49 (d, 1H, J=5.2 Hz, Pyrimidin-H), 8.62 (s, 1H, Ph-H), 8.92 (d, 1H, J=8.0 Hz, Ph-H), 9.01 (s, 1H, Ar—H). MS (ESI+) m/z 361.1308 (M+H)+.

Example 7

4-(4-(1-Propyl-1H-pyrrolo[2,3-b]pyridin-3-yl)pyrimidin-2-ylamino)phenol (Compound 15)

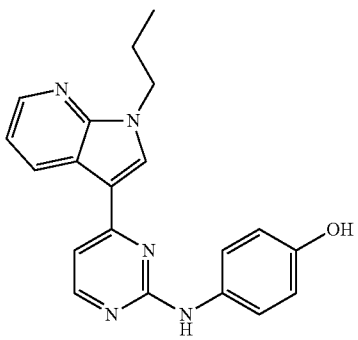

Prepared by treatment of (E)-3-(dimethylamino)-1-(1-propyl-1H-pyrrolo[2,3-b]pyridin-3-yl)prop-2-en-1-one with 1-(4-hydroxyphenyl)guanidine hydrochloride. $^1$H-NMR (DMSO-d$_6$) δ: 0.88 (t, 3H, J=7.2 Hz, CH$_3$), 1.90 (t, 2H, J=7.6 Hz, CH$_2$), 4.30 (t, 2H, J=6.8 Hz, CH$_2$), 6.74 (m, 2H, Ph-H), 7.16 (d, 1H, J=5.6 Hz, Pyrimidin-H), 7.20 (t, 1H, J=4.8 Hz, Ar—H), 7.51 (m, 2H, Ph-H), 8.30 (d, 1H, J=5.6 Hz, Pyrimidin-H), 8.35 (m, 1H, Ar—H), 8.52 (s, 1H, Ar—H), 8.88 (d, 1H, J=7.6 Hz, Ar—H), 9.05 (s, 1H, NH), 9.11 (s, 1H, OH). MS (ESI⁺) m/z 346.1659 (M+H)⁺.

Example 8

3-(4-(1-Propyl-1H-pyrrolo[2,3-b]pyridin-3-yl)pyrimidin-2-ylamino)phenol Compound 16)

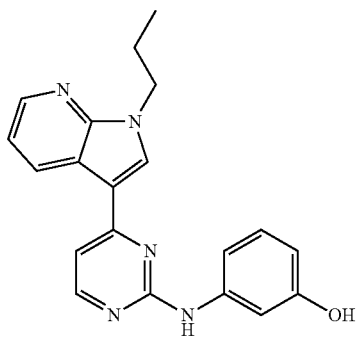

Prepared by treatment of (E)-3-(dimethylamino)-1-(1-propyl-1H-pyrrolo[2,3-b]pyridin-3-yl)prop-2-en-1-one with 1-(3-hydroxyphenyl)guanidine hydrochloride. ¹H-NMR (DMSO-d₆) δ: 0.88 (t, 3H, J=7.2 Hz, CH₃), 1.91 (t, 2H, J=7.6 Hz, CH₂), 4.31 (t, 2H, J=6.8 Hz, CH₂), 6.40 (m, 1H, Ph-H), 7.08 (t, 1H, J=7.6 Hz, Ph-H), 7.18 (m, 1H, Ar—H), 7.24 (d, 1H, J=5.6 Hz, Pyrimidin-H), 7.37 (s, 1H, Ph-H), 8.36 (m, 2H, Pyrimidin-H and Ar—H), 8.57 (s, 1H, Ar—H), 8.30 (d, 1H, J=5.6 Hz, Pyrimidin-H), 8.35 (m, 1H, Ph-H), 8.57 (s, 1H, Ar—H), 9.00 (d, 1H, J=8.0 Hz, Ar—H), 9.24 (s, 1H, NH), 9.33 (s, 1H, OH). MS (ESI⁺) m/z 346.1654 (M+H)⁺.

Example 9

N-(3-Nitrophenyl)-4-(1-propyl-1H-pyrrolo[2,3-b]pyridin-3-yl)pyrimidin-2-amine (Compound 17)

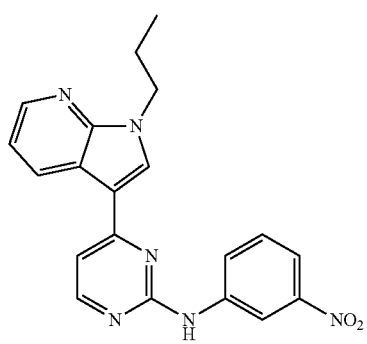

Prepared by treatment of (E)-3-(dimethylamino)-1-(1-propyl-1H-pyrrolo[2,3-b]pyridin-3-yl)prop-2-en-1-one with 1-(3-nitrophenyl)guanidine hydrochloride. ¹H-NMR (DMSO-d₆) δ: 0.90 (t, 3H, J=7.2 Hz, CH₃), 1.93 (t, 2H, J=7.6 Hz, CH₂), 4.33 (t, 2H, J=6.8 Hz, CH₂), 7.26 (q, 1H, J=4.4 Hz, Ar—H), 7.40 (d, 1H, J=5.6 Hz, Pyrimidin-H), 7.61 (t, 1H, J=8.4 Hz, Ph-H), 7.81 (m, 1H, Ph-H), 8.12 (m, 1H, Ph-H), 8.37 (m, 1H, Ar—H), 8.48 (d, 1H, J=5.6 Hz, Pyrimidin-H), 8.64 (s, 1H, Ar—H), 8.92 (d, 1H, J=8.0 Hz, Ar—H), 9.00 (s, 1H, NH). MS (ESI⁺) m/z 375.1519 (M+H)⁺.

Example 10

3-(4-(1-Ethyl-1H-pyrrolo[2,3-b]pyridin-3-yl)pyrimidin-2-ylamino)benzenesulfonamide (Compound 18)

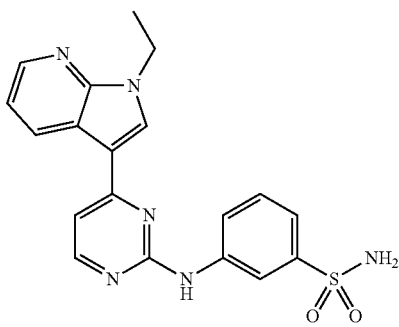

Prepared by treatment of (E)-3-(dimethylamino)-1-(1-ethyl-1H-pyrrolo[2,3-b]pyridin-3-yl)prop-2-en-1-one and 3-guanidinobenzenesulfonamide hydrochloride. ¹H-NMR (DMSO-d₆) δ: 1.48 (t, 3H, J=7.2 Hz, CH₃), 4.39 (q, 2H, J=7.2 Hz, CH₂), 7.27 (m, 1H, Ar—H), 7.33 (m, 3H, Pyrimidin-H and NH₂), 7.42 (m, 1H, Ph-H), 7.50 (t, 1H, J=7.6 Hz, Ph-H), 7.92 (d, 1H, J=8.0 Hz, Ph-H), 8.36 (m, 1H, Ar—H), 8.45 (d, 1H, J=5.6 Hz, Pyrimidin-H), 8.57 (s, 1H, Ar—H), 8.65 (s, 1H, Ar—H), 8.90 (d, 1H, J=8.0 Hz, Ph-H), 9.82 (s, 1H, Ar—H), 9.33 (s, 1H, NH). MS (ESI⁺) m/z 332.1355 (M+H)⁺.

Example 11

3-(4-(1-Ethyl-1H-pyrrolo[2,3-b]pyridin-3-yl)pyrimidin-2-ylamino)benzamide (Compound 19)

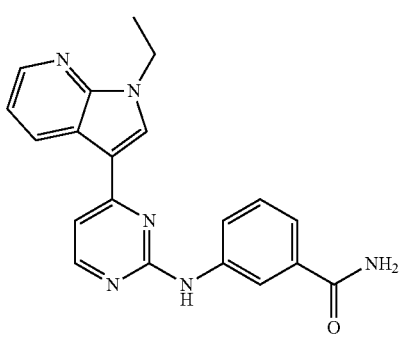

Prepared by treatment of (E)-3-(dimethylamino)-1-(1-ethyl-1H-pyrrolo[2,3-b]pyridin-3-yl)prop-2-en-1-one and 3-guanidinobenzamide hydrochloride. ¹H-NMR (DMSO-d₆) δ: 1.48 (t, 3H, J=7.2 Hz, CH₃), 4.38 (q, 2H, J=7.2 Hz, CH₂), 7.23 (m, 1H, Ar—H), 7.25 (m, 1H, Pyrimidin-H), 7.30 (m, 2H, Ph-H and Ar—H), 7.46 (m, 2H, Ph-H and Ar—H), 8.35 (d, 1H, J=5.6 Hz, Pyrimidin-H), 8.42 (m, 3H, Ph-H and NH₂), 8.65 (s, 1H, Ar—H), 8.91 (d, 1H, J=8.0 Hz, Ph-H), 9.59 (s, 1H, NH). MS (ESI⁺) m/z 359.1619 (M+H)⁺.

Example 12

3-(4-(1-Ethyl-1H-pyrrolo[2,3-b]pyridin-3-yl)pyrimidin-2-ylamino)benzonitrile (Compound 20)

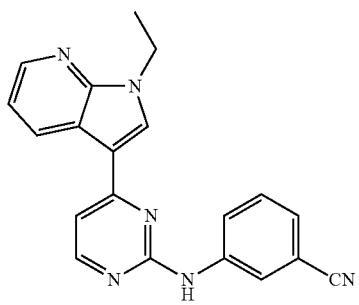

Prepared by treatment of (E)-3-(dimethylamino)-1-(1-ethyl-1H-pyrrolo[2,3-b]pyridin-3-yl)prop-2-en-1-one and 1-(3-cyanophenyl)guanidine hydrochloride. ¹H-NMR (DMSO-d₆) δ: 1.48 (t, 3H, J=7.2 Hz, CH₃), 4.39 (q, 2H, J=7.2 Hz, CH₂), 7.27 (m, 1H, Ar—H), 7.36 (d, 1H, J=4.4 Hz, Pyrimidin-H), 7.42 (m, 1H, Ph-H or Ar—H), 7.51 (m, 1H, Ph-H or Ar—H), 7.98 (m, 1H, Ar—H), 8.38 (m, 1H, Ph-H or Ar—H), 8.46 (m, 2H, Pyrimidin-H or Ar—H), 8.63 (s, 1H, Ar—H), 8.94 (m, 1H, Ph-H or Ar—H), 9.85 (s, 1H, NH). MS (ESI⁺) m/z 341.1489 (M+H)⁺.

Example 13

3-(4-(1-Propyl-1H-pyrrolo[2,3-b]pyridin-3-yl)pyrimidin-2-ylamino)benzenesulfonamide (Compound 22)

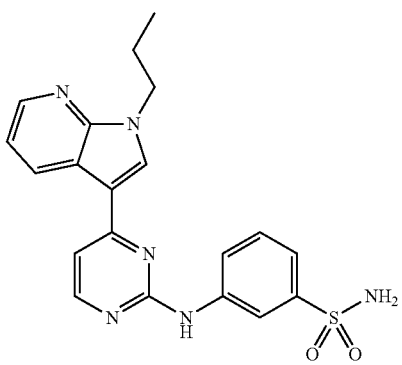

Prepared by treatment of (E)-3-(dimethylamino)-1-(1-ethyl-1H-pyrrolo[2,3-b]pyridin-3-yl)prop-2-en-1-one and 3-guanidinobenzenesulfonamide hydrochloride as described above. ¹H-NMR (DMSO-d₆) δ: 0.88 (t, 3H, J=7.2 Hz, CH₃), 1.91 (m, 2H, CH₂), 4.32 (t, 2H, J=7.2 Hz, CH₂), 7.27 (m, 1H, Ar—H), 7.32 (s, 2H, NH₂), 7.36 (m, 1H, J=5.2 Hz, Pyrimidin-H), 7.43 (m, 1H, Ph-H), 7.51 (m, 1H, Ph-H), 7.92 (d, 1H, J=8.0 Hz, Ph-H), 8.36 (m, 1H, Ar—H), 8.44 (d, 1H, J=5.2 Hz, Pyrimidin-H), 8.56 (s, 1H, Ar—H), 8.63 (s, 1H, Ph-H), 8.91 (d, 1H, J=6.8 Hz, Ar—H), 9.82 (s, 1H, NH). MS (ESI⁺) m/z 409.8665 (M+H)⁺.

Example 14

4-(4-(1-Propyl-1H-pyrrolo[2,3-b]pyridin-3-yl)pyrimidin-2-ylamino)benzenesulfonamide (Compound 23)

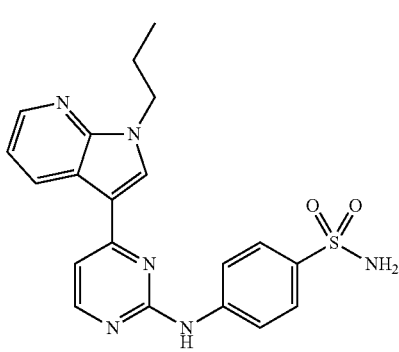

Prepared by treatment of (E)-3-(dimethylamino)-1-(1-ethyl-1H-pyrrolo[2,3-b]pyridin-3-yl)prop-2-en-1-one and 4-guanidinobenzenesulfonamide hydrochloride as described above. ¹H-NMR (DMSO-d₆) δ: 0.90 (t, 3H, J=7.2 Hz, CH₃), 1.91 (m, 2H, CH₂), 4.33 (t, 2H, J=7.2 Hz, CH₂), 7.19 (s, 2H, NH₂), 7.29 (m, 1H, Ar—H), 7.36 (m, 1H, J=5.6 Hz, Pyrimidin-H), 7.77 (d, 2H, J=7.2 Hz, Ph-H), 8.00 (d, 2H, J=7.2 Hz, Ph-H), 8.38 (m, 1H, Ar—H), 8.45 (d, 1H, J=5.6 Hz, Pyrimidin-H), 8.62 (s, 1H, Ar—H), 8.97 (m, 1H, Ar—H), 9.88 (s, 1H, NH). MS (ESI⁺) m/z 409.8708 (M+H)⁺.

Example 15

N-(4-Methyl-3-(morpholinosulfonyl)phenyl)-4-(1-propyl-1H-pyrrolo[2,3-b]pyridin-3-yl)pyrimidin-2-amine (Compound 24)

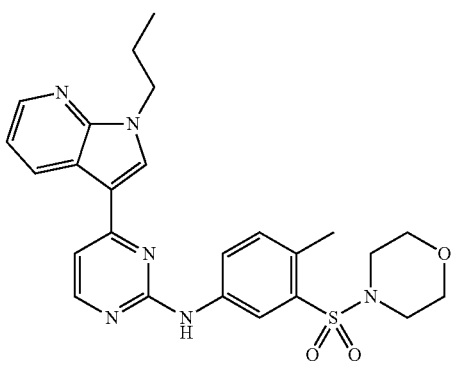

Prepared by treatment of (E)-3-(dimethylamino)-1-(1-ethyl-1H-pyrrolo[2,3-b]pyridin-3-yl)prop-2-en-1-one and 1-(4-methyl-3-(morpholinosulfonyl)phenyl)guanidine hydrochloride as described above. ¹H-NMR (DMSO-d₆) δ: 0.89 (t, 3H, J=7.2 Hz, CH₃), 1.92 (m, 2H, CH₂), 1.99 (s, 3H, CH₃), 3.07 (m, 4H, CH₂×2), 3.64 (m, 4H, CH₂×2), 4.32 (t, 2H, J=7.2 Hz, CH₂), 7.27 (m, 1H, Ar—H), 7.33 (m, 1H, J=5.6

Hz, Pyrimidin-H), 7.40 (d, 1H, J=8.4 Hz, Ph-H), 7.98 (m, 1H, Ph-H), 8.36 (m, 1H, Ar—H), 8.43 (d, 1H, J=5.6 Hz, Pyrimidin-H), 8.49 (m, 1H, Ph-H), 8.64 (s, 1H, Ar—H), 8.92 (m, 1H, Ar—H), 9.79 (s, 1H, NH). MS (ESI$^+$) m/z 493.7652 (M+H)$^+$.

Example 16

(4-Methylpiperazin-1-yl)(3-(4-(1-propyl-1H-pyrrolo [2,3-b]pyridin-3-yl)pyrimidin-2-ylamino)phenyl) methanone (Compound 34)

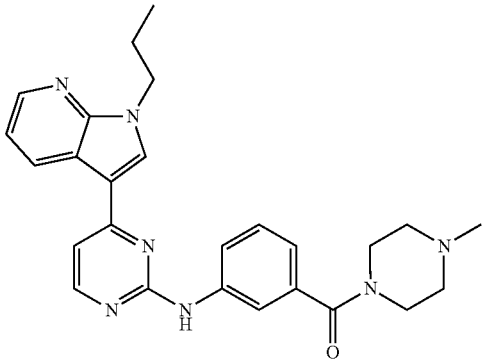

Prepared by treatment of (E)-3-(dimethylamino)-1-(1-ethyl-1H-pyrrolo[2,3-b]pyridin-3-yl)prop-2-en-1-one and 1-(3-(4-methylpiperazine-1-carbonyl)phenyl)guanidine hydrochloride as described above. $^1$H-NMR (DMSO-d$_6$) δ: 0.90 (t, 3H, J=7.2 Hz, CH$_3$), 1.90 (m, 2H, CH$_2$), 2.19 (s, 3H, CH$_3$), 3.07 (m, 4H, CH$_2$×2), 3.61 (m, 4H, CH$_2$×2), 4.31 (t, 2H, J=7.2 Hz, CH$_2$), 7.26 (m, 1H, Ar—H), 7.34 (m, 1H, J=5.6 Hz, Pyrimidin-H), 7.44 (m, 1H, Ph-H), 7.98 (m, 1H, Ph-H), 8.34 (m, 1H, Ar—H), 8.45 (d, 1H, J=5.6 Hz, Pyrimidin-H), 8.49 (m, 1H, Ph-H), 8.64 (s, 1H, Ar—H), 8.92 (m, 1H, Ar—H), 9.79 (s, 1H, NH). MS (ESI$^+$) m/z 456.8986 (M+H)$^+$.

Example 17

3-(4-(5-Chloro-7-methyl-1-propyl-1H-pyrrolo[3,2-b] pyridin-3-yl)pyrimidin-2-ylamino)benzenesulfonamide (Compound 42)

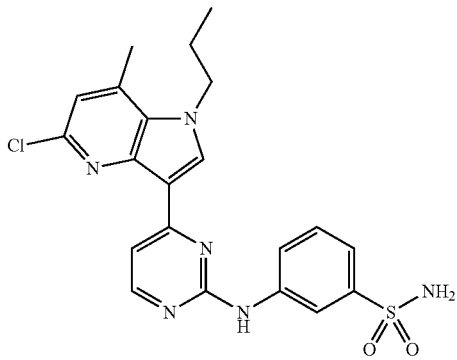

A solution of 2-chloro-4-methyl-5-nitro-pyridine (31.5 mmol) in dry THF cooling at −78° C. was added 100 mL vinylmagnisium bromide (1.0 M in THF). After stirring at −78° C. for 1 hr, the mixture was warmed to −20° C. and stirred for further 8 hrs. NH$_4$Cl (20% in H$_2$O, 150 mL) was added cautiously and the mixture was extracted with EtOAc (3×150 mL). The organic layers were combined, washed with brine, dried on MgSO$_4$ and filtered. The filtrate was evaporated in vacuo. The residue was purified by column chromatography using EtOAcv/PE (1:4, v/v) to elute 2.4 g 5-chloro-7-methyl-1H-pyrrolo[3,2-b]pyridine as white solid. $^1$H-NMR (DMSO-d$_6$) δ: 6.51 (m, 1H, Ar—H), 6.99 (s, 1H, Ar—H), 7.68 (t, 1H, J=2.8 Hz, Ar—H). MS (ESI$^+$) m/z 167.0419 (M+H)$^+$.

A solution of 5-chloro-7-methyl-1H-pyrrolo[3,2-b]pyridine (5 mmol) in dry DMF (10 mL) cooling on an ice bath was treated with NaH (60 mmol) under N$_2$. After stirring at room temperature for 45 minutes iodopropane (10 mmol) was added. The mixture was allowed to react for further 3 hrs. Upon cooling on an ice bath it was treated with H$_2$O (3 mL). The mixture was then extracted with diethyl ether (4×50 mL). The ether layers were combined, washed with brine, dried on MgSO$_4$ and filtered. The solvent was evaporated to give 5-chloro-7-methyl-1-propyl-1H-pyrrolo[3,2-b]pyridine as orange oil. $^1$H-NMR (DMSO-d$_6$) δ: 0.85 (t, 3H, J=7.6 Hz, CH$_3$), 1.75 (m, 2H, CH$_2$), 4.28 (t, 2H, J=7.6 Hz, CH$_2$), 6.48 (d, 1H, J=3.2 Hz, Ar—H), 6.97 (s, 1H, Ar—H), 7.66 (d, 1H, J=3.6 Hz, Ar—H). MS (ESI$^+$) m/z 209.0648 (M+H)$^+$.

A mixture of 5-chloro-7-methyl-1-propyl-1H-pyrrolo[3,2-b]pyridine (4 mmol) and AlCl$_3$ (120 mmol) in dry CH$_2$Cl$_2$ was stirred at room temperature for 1 hr under N$_2$. Upon cooling on an ice bath the mixture was added acetyl chloride (30 mmol) and stirred at room temperature for further 2 hrs. MeOH (50 mL) was added dropwise. The mixture was concentrated in vacuo and purified by column chromatography using EtOAc/MeOH (10:1, v/v) to elute 1-(5-chloro-7-methyl-1-propyl-1H-pyrrolo[3,2-b]pyridin-3-yl)ethanone as light yellow solid. $^1$H-NMR (DMSO-d$_6$) δ: 0.85 (t, 3H, J=7.6 Hz, CH$_3$), 1.79 (m, 2H, CH$_2$), 2.51 (s, 3H, CH$_3$), 4.37 (t, 2H, J=7.3 Hz, CH$_2$), 7.17 (s, 1H, Ar—H), 8.38 (s, 1H, Ar—H). MS (ESI$^+$) m/z 251.0894 (M+H)$^+$.

1-(5-Chloro-7-methyl-1-propyl-1H-pyrrolo[3,2-b]pyridin-3-yl)ethanone (0.8 mmol) was treated with N,N-dimethylformamide dimethyal acetal (3 mL). The mixture was microwaved at 160° C. for 60 minutes. The precipitates were collected by filtration followed by recrystallisation from EtOAc to give (E)-1-(5-chloro-7-methyl-1-propyl-1H-pyrrolo[3,2-b]pyridin-3-yl)-3-(dimethylamino)prop-2-en-1-one as yellow crystals. $^1$H-NMR (DMSO-d$_6$) δ: 0.86 (t, 3H, J=7.2 Hz, CH$_3$), 1.77 (m, 2H, CH$_2$), 4.34 (t, 2H, J=7.2 Hz, CH$_2$), 6.65 (d, 1H, J=12.4 Hz, CH), 7.09 (s, 1H, Ar—H), 7.67 (d, 1H, J=12.4 Hz, CH), 8.17 (s, 1H, Ar—H). MS (ESI$^+$) m/z 306.1259 (M+H)$^+$.

A mixture of (E)-1-(5-chloro-7-methyl-1-propyl-1H-pyrrolo[3,2-b]pyridin-3-yl)-3-(dimethylamino)prop-2-en-1-one (0.2 mmol), 3-guanidinobenzenesulfonamide hydrochloride (0.5 mmol) and NaOH (0.8 mmol) in 3 mL of 2-methoxyethanol was heated in a Microwave at 150° C. for 30 minutes. The reaction mixture was purified by column chromatography using EtOAc/PE (1:1, v/v) to elute 3-(4-(5-chloro-7-methyl-1-propyl-1H-pyrrolo[3,2-b]pyridin-3-yl)pyrimidin-2-ylamino)benzenesulfonamide which was re-crystallised from EtOAc to give white solid. $^1$H-NMR (DMSO-d$_6$) δ: 0.92 (t, 3H, J=7.2 Hz, CH$_3$), 1.87 (m, 2H, CH$_2$), 4.42 (t, 2H, J=7.2 Hz, CH$_2$), 7.19 (s, 1H, Ar—H or Ph-H), 7.34 (s, 2H, NH$_2$), 7.43 (m, 1H, Ar—H or Ph-H), 7.49 (t, 1H, J=7.6 Hz, Ph-H), 7.62 (m, 1H, Ph-H), 8.02 (d, 1H, J=4.8 Hz, Pyrimidin-H), 8.55 (d, 1H J=5.2 Hz, Pyrimidin-H), 8.63 (s, 1H, Ar—H), 9.92 (s, 1H, NH). MS (ESI⁺) m/z 457.1245 (M+H)⁺.

Example 18

4-(4-(5-Chloro-7-methyl-1-propyl-1H-pyrrolo[3,2-b]pyridin-3-yl)pyrimidin-2-ylamino)benzenesulfonamide (Compound 39)

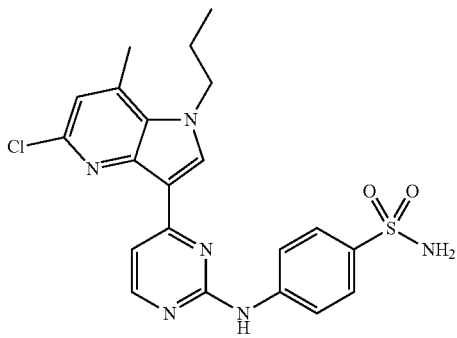

Prepared by treatment of (E)-1-(5-chloro-7-methyl-1-propyl-1H-pyrrolo[3,2-b]pyridin-3-yl)-3-(dimethylamino)prop-2-en-1-one and 3-guanidinobenzenesulfonamide hydrochloride. ¹H-NMR (DMSO-d₆) δ: 0.93 (t, 3H, J=7.2 Hz, CH₃), 1.84 (m, 2H, CH₂), 4.47 (t, 2H, J=7.2 Hz, CH₂), 7.18 (m, 3H, Ar—H and NH₂), 7.79 (d, 2H, J=8.8 Hz, Ph-H), 8.03 (d, 1H, J=5.2 Hz, Pyrimidin-H), 8.07 (d, 2H, J=8.8 Hz, Ph-H), 8.48 (s, 1H, Ar—H), 8.56 (d, 1H, J=5.2 Hz, Pyrimidin-H), 9.90 (s, 1H, NH). MS (ESI⁺) m/z 456.7704.

Example 19

4-(4-(7-Chloro-1-ethyl-1H-pyrrolo[2,3-c]pyridin-3-yl)pyrimidin-2-ylamino)phenol (Compound 70)

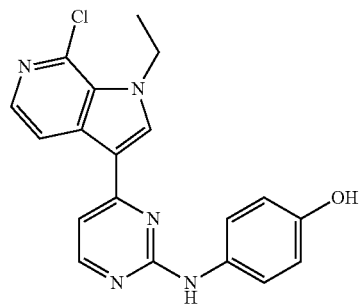

A solution of 2-chloro-3-nitropyridine (31.5 mmol) in dry THF (200 mL) was cooled to −78° C. Vinylmagnisium bromide (1.0 M in THF, 100 mL) was added dropwise under N₂. The mixture was stirred at −78° C. for 1 hr, followed by −20° C. for further 8 hrs. The mixture was quenched with 150 mL NH₄Cl (20% in H₂O) and extracted with EtOAc (3×150 mL). The organic layers were combined, washed with brine, dried on MgSO₄ and filtered. The solvent was evaporated and the residue was purified by column chromatography using EtOAc/PE (1:3, v/v) to elute 7-chloro-1H-pyrrolo[2,3-c]pyridine as white solid (1.77 g, yield 37%). ¹H-NMR (DMSO-d₆) δ: 6.63 (d, 1H, J=3.2 Hz, Ar—H), 7.58 (d, 1H, J=5.6 Hz, Ar—H), 7.66 (d, 1H, J=2.8 Hz, Ar—H), 7.90 (d, 1H, J=5.2 Hz, Ar—H). MS (ESI⁺) m/z 153.0260 (M+H)⁺.

A mixture of 7-chloro-1H-pyrrolo[2,3-c]pyridine (11 mmol) in dry DMF (20 mL) was cooled on an ice bath, NaH (143 mmol) was added portion wise under N₂. The mixture was allowed to stir at room temperature for 1 hr. Upon cooling to 0° C., iodoethane (26 mmol) was added and the mixture was reacted for further 3 his. After quenching with H₂O (20 mL), the mixture was diluted with diethyl ether and extracted with ether (4×50 mL). The organic layers were combined, washed with brine, dried with MgSO₄ and filtered. The solvent was evaporated to give 7-chloro-1-ethyl-1H-pyrrolo[2,3-c]pyridine as orange oil. MS (ESI⁺) m/z 181.0533 (M+H)⁺.

To a suspension of AlCl₃ (55 mmol) in dry CH₂Cl₂ (300 mL) 7-chloro-1-ethyl-1H-pyrrolo[2,3-c]pyridine (11 mmol) was added. After stirred at room temperature for 1 hr, acetyl chloride (55 mmol) was added. The reaction mixture was allowed to react for further 2 hrs. Upon cooling on an ice bath MeOH (80 mL) was added. The mixture was concentrated followed by column chromatography using EtOAc/MeOH (10:1, v/v) to elute 1-(7-chloro-1-ethyl-1H-pyrrolo[2,3-c]pyridin-3-yl)ethanone as off-white solid. ¹H-NMR (DMSO-d₆) δ: 1.47 (t, 3H, J=7.2 Hz, CH₃), 4.62 (t, 2H, J=7.2 Hz, CH₂), 8.11 (m, 2H, Ar—H), 8.68 (s, 1H, Ar—H). MS (ESI⁺) m/z 223.0384 (M+H)⁺.

A mixture of 1-(7-chloro-1-ethyl-1H-pyrrolo[2,3-c]pyridin-3-yl)ethanone (3 mmol) treated with 3.5 mL N,N-dimethylformamide dimethyl acetal was microwaved at 150° C. for 35 minutes. The mixture was evaporated to dryness and purified by column chromatography using EtOAc/MeOH (10:1) to elute (E)-1-(7-chloro-1-ethyl-1H-pyrrolo[2,3-c]pyridin-3-yl)-3-(dimethylamino)prop-2-en-1-one as yellow solid. ¹H-NMR (DMSO-d₆) δ: 1.43 (t, 3H, J=7.2 Hz, CH₃), 4.43 (t, 2H, J=7.2 Hz, CH₂), 5.72 (d, 1H, J=12.4 Hz, CH), 7.58 (d, 1H, J=12.4 Hz, CH), 7.71 (d, 1H, J=5.6 Hz, Ar—H), 7.79 (d, 1H, J=5.6 Hz, Ar—H), 8.25 (s, 1H, Ar—H). MS (ESI⁺) m/z 278.1045 (M+H)⁺.

A mixture of (E)-1-(7-chloro-1-ethyl-1H-pyrrolo[2,3-c]pyridin-3-yl)-3-(dimethylamino)prop-2-en-1-one (0.5 mmol), 1-(4-hydroxyphenyl)guanidine hydrochloride (0.5 mmol) and NaOH (2 mmol) in a mixture of EtOH-MeCN (1:2, v/v, 3 mL) was heated in a microwave at 150° C. for 25 minutes. The residue was purified by column chromatography using EtOAc/PE (1:3, v/v) to yield 4-(4-(7-chloro-1-ethyl-1H-pyrrolo[2,3-c]pyridin-3-yl)pyrimidin-2-ylamino)phenol as white solid. ¹H-NMR (DMSO-d₆) δ: 1.43 (m, 3H, CH₃), 4.49 (m, 2H, CH₂), 6.74 (m, 2H, Ph-H), 7.11 (d, 1T-F=5.6 Hz, Pyrimidin-H), 7.52 (m, 2H, Ph-H), 7.74 (d, 1H, J=5.6 Hz, Ar—H), 8.10 (d, 1H, J=5.2 Hz, Ar—H), 8.29 (d, 1H J=5.6 Hz, Pyrimidin-H), 8.37 (s, 1H, Ar—H), 9.04 (s, 1H, OH), 9.09 (s, 1H, NH). MS (ESI⁺) m/z 362.1609 (M+H)⁺.

The following compounds were synthesised by an analogous route.

Example 20

3-(4-(7-Chloro-1-ethyl-1H-pyrrolo[2,3-c]pyridin-3-yl)pyrimidin-2-ylamino)phenol (Compound 72)

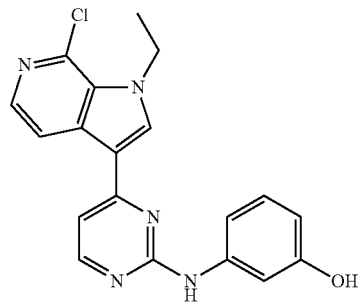

Prepared by treatment of (E)-1-(7-chloro-1-ethyl-1H-pyrrolo[2,3-c]pyridin-3-yl)-3-(dimethylamino)prop-2-en-1-one with 1-(3-hydroxyphenyl)guanidine hydrochloride. $^1$H-NMR (DMSO-d$_6$) δ: 1.46 (m, 3H, CH$_3$), 4.49 (m, 2H, CH$_2$), 6.39 (m, 1H, Ph-H), 7.07 (m, 1H, Ph-H), 7.20 (m, 2H, Ph-H and Ar—H), 7.77 (d, 1H, J=5.6 Hz, Pyrimidin-H), 8.18 (d, 1H, J=5.6 Hz, Ar—H), 8.37 (d, 1H, J=5.6 Hz, Pyrimidin-H), 8.41 (s, 1H, Ar—H), 9.23 (s, 1H, OH), 9.32 (s, 1H, NH). MS (ESI$^+$) m/z 362.1670 (M+H)$^+$

Example 21

3-(4-(7-Chloro-1-ethyl-1H-pyrrolo[2,3-c]pyridin-3-yl)pyrimidin-2-ylamino)benzenesulfonamide (Compound 73)

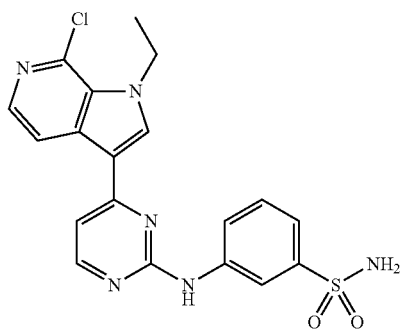

Prepared by treatment of (E)-1-(7-chloro-1-ethyl-1H-pyrrolo[2,3-c]pyridin-3-yl)-3-(dimethylamino)prop-2-en-1-one and 3-guanidinobenzenesulfonamide hydrochloride. $^1$H-NMR (DMSO-d$_6$) δ: 1.45 (t, 3H, J=7.2 Hz, CH$_3$), 4.48 (t, 2H, J=7.2 Hz, CH$_2$), 7.30 (m, 3H, Pyrimidin-H and NH$_2$), 7.43 (m, 1H, Ar—H or Ph-H), 7.50 (t, 1H, J=7.6 Hz, Ph-H), 7.82 (d, 1H, J=5.6 Hz, Ar—H), 7.89 (m, 1H, Ar—H or Ph-H), 8.07 (m, 1H, Ar—H or Ph-H), 8.45 (d, 1H, J=5.6 Hz, Pyrimidin-H), 8.48 (s, 1H, Ar—H), 8.61 (s, 1H, NH). MS (ESI$^+$) m/z 426.1490 (M+H)$^+$.

Example 22

3-(4-(7-chloro-1-propyl-1H-pyrrolo[2,3-c]pyridin-3-yl)pyrimidin-2-ylamino)benzenesulfonamide (Compound 96)

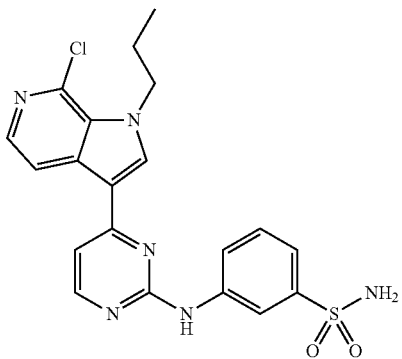

Prepared by treatment of (E)-1-(7-chloro-1-ethyl-1H-pyrrolo[2,3-c]pyridin-3-yl)-3-(dimethylamino)prop-2-en-1-one and 3-guanidinobenzenesulfonamide hydrochloride. $^1$H-NMR (DMSO-d$_6$) δ: 0.79 (t, 3H, J=7.2 Hz, CH$_3$), 1.18 (m, 2H, J=7.2 Hz, CH$_2$), 4.46 (m, 2H, CH$_2$), 7.34 (m, 3H, Ar—H and NH$_2$), 7.46 (m, 1H, Ar—H or Ph-H), 7.54 (m, 1H, Ph-H or Ar—H), 7.91 (m, 1H, Ar—H), 8.11 (d, 1H, J=5.6 Hz, Pyrimidin-H), 8.49 (d, 1H, J=5.6 Hz, Pyrimidin-H), 8.54 (s, 1H, Ar—H or Ph-H), 8.56 (m, 1H, Ar—H), 8.71 (s, 1H, Ar—H), 9.90 (s, 1H, NH). MS (ESI$^+$) m/z 444.7773 (M+H)$^+$.

Example 23

4-(4-(7-Chloro-1-propyl-1H-pyrrolo[2,3-c]pyridin-3-yl)pyrimidin-2-ylamino)benzenesulfonamide (Compound 97)

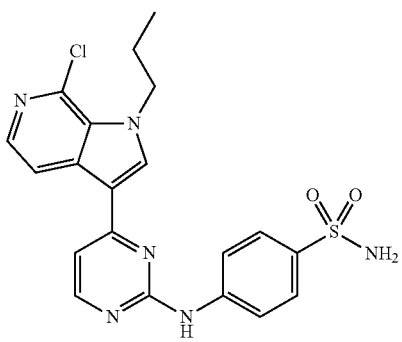

Prepared by treatment of (E)-1-(7-chloro-1-ethyl-1H-pyrrolo[2,3-c]pyridin-3-yl)-3-(dimethylamino)prop-2-en-1-one and 4-guanidinobenzenesulfonamide hydrochloride. $^1$H-NMR (DMSO-d$_6$) δ: 0.79 (t, 3H, J=7.2 Hz, CH$_3$), 1.18 (m, 2H, J=7.2 Hz, CH$_2$), 4.46 (m, 2H, CH$_2$), 5.79 (s, 2H, NH$_2$), 6.58 (m, 3H, Ph-H and Ar—H), 6.88 (m, 2H, Ar—H), 7.21

(m, 2H, Ph-H), 7.61 (d, 1H, J=6.0 Hz, Pyrimidin-H), 7.73 (d, 1H, J=6.0 Hz, Pyrimidin-H), 10.14 (s, 1H, NH). MS (ESI$^+$) m/z 442.0773.

Example 24

4-(7-Chloro-1-propyl-1H-pyrrolo[2,3-c]pyridin-3-yl)-N-(4-methyl-3-(morpholinosulfonyl)phenyl)pyrimidin-2-amine (Compound 101)

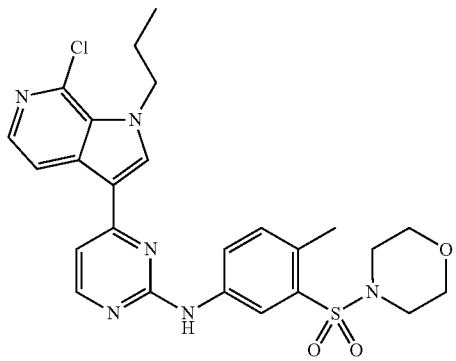

Prepared by treatment of (E)-1-(7-chloro-1-ethyl-1H-pyrrolo[2,3-c]pyridin-3-yl)-3-(dimethylamino)prop-2-en-1-one and 1-(3-(morpholinosulfonyl)phenyl)guanidine hydrochloride. $^1$H-NMR (DMSO-d$_6$) δ: 0.86 (t, 3H, J=7.2 Hz, CH$_3$), 1.86 (m, 2H, CH$_2$), 2.53 (m, 4H, CH$_2$×2), 3.25 (m, 4H, CH$_2$×2), 4.06 (s, 3H, CH$_3$), 4.35 (t, 2H, J=7.2 Hz, CH$_2$), 7.28 (d, 1H, J=5.6 Hz, Pyrimidin-H), 7.40 (d, 1H, J=8.8 Hz, Ar—H or Ph-H), 7.81 (d, 1H, J=5.6 Hz, Ar—H), 7.95 (m, 1H Ar—H or Ph-H), 8.18 (m, 1H, Ar—H or Ph-H), 8.43 (d, 1H, J=5.6 Hz, Pyrimidin-H), 8.48 (s, 1H, Ar—H or Ph-H), 8.54 (m, 1H, Ar—H), 9.79 (s, 1H, NH). MS (ESI$^+$) m/z 526.6872.

Example 25

N-(4-Methyl-3-(morpholinosulfonyl)phenyl)-4-(1-propyl-1H-pyrrolo[2,3-c]pyridin-3-yl)pyrimidin-2-amine (Compound 102)

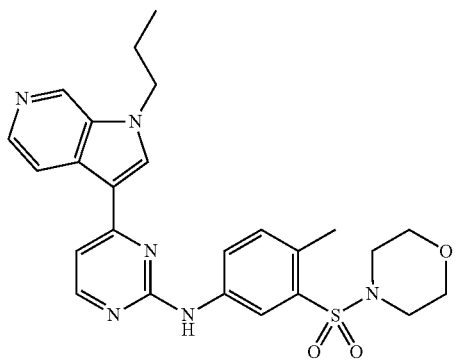

Hydrogenation of 7-chloro-1H-pyrrolo[2,3-c]pyridine (10 mmol) was carried out in the presence of Pd—C (10%) in EtOH (50 mL). After stirred at room temperature for 20 hrs, the mixture was filtered through a pad of celite 521. The residue was washed with EtOH several times. The filtrate was evaporated to yield 1H-pyrrolo[2,3-c]pyridine as brown oil. MS (ESI$^+$) m/z 119.0657 (M+H)$^+$.

A solution of 1H-pyrrolo[2,3-c]pyridine (10 mmol) in DMF cooling on an ice bath was treated with NaH (143 mmol). After stirred at room temperature for 1hr iodopropane (26 mmol) was added dropwise. The mixture was allowed to react at room temperature for further 3 hrs. Upon cooling on an ice bath the mixture was quenched with 20 mL H$_2$O, followed by extraction with diethyl ether (5×50 mL). The organic layers were combined, washed with brine, dried on MgSO$_4$ and filtered. The solvent was evaporated and dried on a high vacuum to give 1-propyl-1H-pyrrolo[2,3-c]pyridine as orange oil. MS (ESI$^+$) m/z 161.1063 (M+H)$^+$.

A mixture of 1-propyl-1H-pyrrolo[2,3-c]pyridine (10 mmol) and AlCl$_3$ (50 mmol) in dry CH$_2$Cl$_2$ (200 mL) was stirred at room temperature for 1 hr before being treated with acetyl chloride (50 mL). After stirred for further 2 hrs, the mixture was quenched with MeOH (55 mL) cautiously. The solvent was evaporated and the residue was purified by column chromatography using EtOAc/MeOH (10:1, v/v) to elute 1-(1-propyl-1H-pyrrolo[2,3-c]pyridin-3-yl)ethanone as off-white solid. $^1$H-NMR (DMSO-d$_6$) δ: 0.89 (t, 3H, J=7.2 Hz, CH$_3$), 1.89 (m, 2H, CH$_2$), 2.47 (s, 3H, CH$_3$), 4.32 (t, 2H, J=7.2 Hz, CH$_2$), 8.05 (d, 1H, J=5.2 Hz, Ar—H), 8.31 (d, 1H, J=5.2 Hz, Ar—H), 8.56 (s, 1H, Ar—H), 9.00 (s, 1H, Ar—H). MS (ESI$^+$) m/z 223.0384 (M+H)$^+$.

A mixture of 1-(1-propyl-1H-pyrrolo[2,3-c]pyridin-3-yl) ethanone (4 mmol) and N,N-dimethylformamide dimethylacetal (25 mmol) was heated in microwave at 150° C. for 15 minutes. The mixture was evaporated to dryness and purified by column chromatography using EtOAc/MeOH (10:1, v/v) to elute (E)-3-(dimethylamino)-1-(1-propyl-1H-pyrrolo[2,3-c]pyridin-3-yl)prop-2-en-1-one as orange solid. $^1$H-NMR (DMSO-d$_6$) δ: 0.86 (t, 3H, J=7.2 Hz, CH$_3$), 1.87 4.29 (t, 2H, J=7.2 Hz, CH$_2$), 5.74 (d, 1H, J=12.4 Hz, CH), 7.58 (d, 1H, J=12.4 Hz, CH), 8.12 (d, 1H, J=5.2 Hz, Ar—H), 8.21 (d, 1H, J=5.2 Hz, Ar—H), 8.40 (s, 1H, Ar—H), 8.92 (s, 1H, Ar—H). MS (ESI$^+$) m/z 258.1546 (M+H)$^+$.

A mixture of (E)-3-(dimethylamino)-1-(1-propyl-1H-pyrrolo[2,3-c]pyridin-3-yl)prop-2-en-1-one (0.5 mmol), 1-(4-methyl-3-(morpholinosulfonyl)phenyl)guanidine hydrochloride (0.5 mmol) and NaOH (1.0 mmol) was microwaved at 150° C. for 15 minutes. The residue was purified by column chromatography using EtOAc to yield N-(4-methyl-3-(morpholinosulfonyl)phenyl)-4-(1-propyl-1H-pyrrolo[2,3-d]pyridin-3-yl)pyrimidin-2-amine as light yellow solid. $^1$H-NMR (DMSO-$d_6$) δ: 0.89 (t, 3H, J=7.2 Hz, $CH_3$), 1.91 (m, 2H, $CH_2$), 3.07 (m, 4H, $CH_2$×2), 3.42 (s, 3H, $CH_3$), 3.64 (m, 4H,$CH_2$×2), 4.35 (t, 2H, J=7.2 Hz, $CH_2$), 7.33 (d, 1H, J=5.6 Hz, Pyrimidin-H), 7.41 (m, 1H, Ar—H or Ph-H), 7.98 (m, 1H, Ar—H or Ph-H), 8.33 (d, 1H J=5.2 Hz, Ar—H), 8.45 (d, 1H, J=5.6 Hz, Pyrimidin-H), 8.52 (s, 1H, Ar—H or Ph-H), 8.65 (s, 1H, Ph-H or Ar—H), 9.02 (s, 1H, Ar—H or Ph-H), 9.92 (s, 1H, Ar—H or Ph-H). MS ($ESI^+$) m/z 493.2182 $(M+H)^+$.

Example 26

3-(4-(1-Propyl-1H-pyrrolo[2,3-c]pyridin-3-yl)pyrimidin-2-ylamino)benzenesulfonamide (Compound 111)

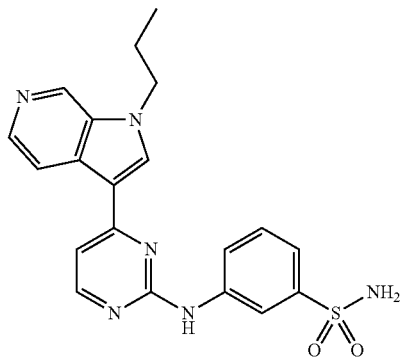

Prepared by treatment of (E)-3-(dimethylamino)-1-(1-propyl-1H-pyrrolo[2,3-c]pyridin-3-yl)prop-2-en-1-one and 3-guanidinobenzenesulfonamide hydrochloride as described above. $^1$H-NMR (DMSO-$d_6$) δ: 0.89 (t, 3H, J=7.2 Hz, $CH_3$), 1.91 (m, 2H, $CH_2$), 4.36 (t, 2H, J=7.2 Hz, $CH_2$), 6.56 (s, 2H, $NH_2$), 7.34 (m, 2H, Pyrimidin-H and Ph-H), 7.44 (m, 1H, Ar—H or Ph-H), 7.91 (m, 1H, Ar—H or Ph-H), 8.33 (d, 1H J=5.2 Hz, Ar—H), 8.45 (d, 1H, J=5.6 Hz, Pyrimidin-H), 8.52 (m, 2H, Ar—H or Ph-H), 9.02 (s, 1H, Ar—H or Ph-H), 9.84 (s, 1H, Ar—H or Ph-H). MS ($ESI^+$) m/z 409.1514 $(M+H)^+$.

Example 27

4-(4-(1-Propyl-1H-pyrrolo[2,3-c]pyridin-3-yl)pyrimidin-2-ylamino)benzenesulfonamide (Compound 112)

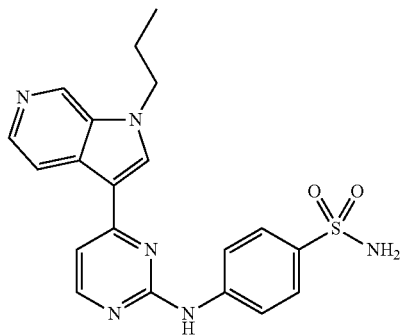

Prepared by treatment of (E)-1-(7-chloro-1-ethyl-1H-pyrrolo[2,3-c]pyridin-3-yl)-3-(dimethylamino)prop-2-en-1-one and 4-guanidinobenzenesulfonamide hydrochloride as described above. $^1$H-NMR (DMSO-$d_6$) δ: 0.92 (t, 3H, J=7.2 Hz, $CH_3$), 1.91 (m, 2H, $CH_2$), 4.36 (t, 2H, J=7.2 Hz, $CH_2$), 7.21 (m, 2H, $NH_2$), 7.36 (d, 1H, J=5.6 Hz, Pyrimidin-H), 7.76 (m, 2H, Ph-H), 8.01 (m, 2H, Ph-H), 8.32 (d, 1H J=5.2 Hz, Ar—H), 8.46 (d, 1H, J=5.6 Hz, Pyrimidin-H), 8.52 (m, 1H, Ar—H), 8.61 (s, 1H, Ar—H), 9.02 (s, 1H, Ar—H), 9.90 (s, 1H, NH). MS ($ESI^+$) m/z 409.8821 $(M+H)^+$.

Example 28

Kinase Inhibitory Activity

Kinase assays. The compounds from the example above were tested for their ability to inhibit kinases. Recombinant human CDK2/cyclinA (PV3267), CDK1/cyclinB (PV3292), CDK5/p35 (PV3000) and Aurora A (PV3612) were purchased from Invitrogen (Carlsbad, Calif., USA). Kinase dosage and Z'-LYTE™ substrate for each kinase assay is as follows: CDK2/cyclinA-8 ng/reaction, Ser/Thr 12 Peptide; CDK1/cyclinB-0.8 ng/reaction, Ser/Thr 12 Peptide, CDK5/p35-0.8 ng/reaction, Ser/Thr 12 Peptide, and Aurora A-16 ng/reaction, Ser/Thr 1 Peptide. All enzymatic assays were performed using Z'-LYTE™ Kinase Assay Kits and were carried out following protocols provided by Invitrogen. To prepare stock solutions, compounds were dissolved at 10 mM in 100% DMSO and stored at 4° C. in amber glass vials. Enzyme reactions were initiated by adding recombinant enzyme and Z'-LYTE™ Ser/Thr peptide substrate and ATP mixture to 384-well plates containing diluted test compounds. Kinase and corresponding peptide substrate were incubated for 1 hr at room temperature in the presence of varying amounts of test compound with reaction buffer (20 µM ATP, 25 in M HEPES [pH 7.5], 5 mM $MgCl_2$, 0.5 mM EGTA, 0.005% Brij-35). Development buffer was added and incubated for another one hour at room temperature. Reactions were terminated by addition of stop buffer, and fluorescence emission intensity ratio 445 nm/520 nm (excited at 400 nm) was quantified by VICTOR-3 Multilabel Reader (Perkin-Elmer, Waltham, Mass., USA). Phosphorylation was calculated from the emission ratio. $IC_{50}$ was determined using Sigmoid curve-fitting software Origin 6.0 (MicroCal, LLC, Northampton, Mass., USA). Kinase activity of representative compounds is presented in Table I.

TABLE I

Kinase inhibitory activity

| Compound No | Kinase inhibition, IC$_{50}$ µM | | | | | |
|---|---|---|---|---|---|---|
| | CDK1B | CDK2A | CDK5/p35 | CDK9T1 | Aurora A | Aurora B |
| 1 | 2.500 | 0.543 | 2.610 | ND | 0.28 | 0.34 |
| 2 | 0.742 | 0.305 | 0.950 | 0.043 | 0.15 | 0.2 |
| 3 | >10 | 7.530 | >10 | >10 | >10 | >10 |
| 4 | >10 | 1.770 | >10 | ND | >10 | >10 |
| 5 | >10 | 100 | >10 | ND | >10 | >10 |
| 6 | 1.210 | 0.003 | 0.522 | 0.026 | 1.05 | 0.47 |
| 7 | 1.340 | 0.002 | 0.375 | 0.029 | 5.84 | 1.01 |
| 8 | 8.950 | 0.411 | >10 | >10 | >10 | >10 |
| 9 | >10 | >100 | >10 | >10 | >10 | >10 |
| 10 | 2.360 | 1.170 | 4.370 | 0.67 | 4.22 | ND |
| 11 | 4.820 | 4.050 | >10 | 1.17 | 4.67 | >10 |
| 12 | 4.110 | 0.172 | 5.540 | >10 | 0.27 | 0.75 |
| 13 | 1.180 | 0.061 | 1.960 | 0.45 | 0.71 | 2.05 |
| 14 | >10 | 1.070 | >10 | 0.79 | 1.34 | >10 |
| 15 | 1.670 | 0.028 | 2.240 | 1.4 | 0.21 | 0.67 |
| 16 | 1.360 | 0.006 | 2.320 | 0.14 | >10 | 1.25 |
| 17 | 7.640 | 0.463 | >10 | 0.16 | 1.16 | >10 |
| 18 | 0.624 | 0.003 | 0.271 | 0.014 | 0.03 | 0.7 |
| 19 | 1.340 | 0.272 | 3.180 | 0.11 | 0.29 | 1.44 |
| 20 | 7.01 | 3.48 | 4.61 | 0.15 | 6.99 | >10 |
| 22 | 0.45 | 0.19 | 0.40 | 0.097 | 0.008 | 3.60 |
| 23 | 0.03 | 0.01 | 0.10 | 0.052 | 4.90 | 5.80 |
| 24 | 5.19 | 4.58 | 8.90 | 1.01 | 9.44 | 10 |
| 34 | 1.57 | 1.34 | 0.62 | 0.35 | >10 | >10 |
| 39 | >10 | 1.67 | >10 | 0.057 | 0.62 | 0.32 |
| 42 | 6.84 | >10 | >10 | 0.041 | 0.098 | 0.19 |
| 70 | 0.19 | 0.016 | 0.35 | 0.095 | 2.46 | >10 |
| 72 | 0.09 | 0.0043 | 0.10 | 0.079 | 0.80 | 0.93 |
| 73 | 0.18 | 0.0038 | 0.19 | 0.024 | 1.28 | >10 |
| 96 | <0.0001 | <0.0001 | 0.02 | 0.0086 | 0.80 | >10 |
| 102 | 0.07 | 0.03 | 0.025 | 0.0004 | 1.65 | 3.42 |
| 111 | 0.0004 | 0.0005 | 0.0005 | 0.0006 | 0.05 | 0.059 |
| 112 | 0.0004 | 0.01 | 0.0013 | 0.0007 | 0.82 | 0.0016 |

ND-Not Determined

Example 29

Cytotoxicity

MIT cytotoxicity assay. The compounds of the invention were subjected to a standard cellular proliferation assay using human cell lines. HeLa cells (Human cervix adenocarcinoma cell line, ATCC NO, CCL-2); A549 cells (Human lung carcinoma cells line, ATCC NO, CCL-185); U2OS cells (Human osteosarcoma cell line, ATCC NO, HTB-96); Eca-109 cells (Human esophageal carcinoma cell line); HepG2 (Human hepatocellular liver carcinoma cell line, ATCC NO, HB-8065); K562 cells (Human chronic myelogenous leukemia cell line, ATCC NO, CCL-243); SK-MEL-28 (Human malignant melanoma cell line, ATCC NO, HTB-72); Molt-4 (Human acute lymphoblastic leukemia cell line, ATCC NO, CRL-1582); H460 (Human large cell lung cancer cell line, ATCC NO, HTB-177); MDA-MB-231 (Human breast adenocarcinoma cell line, ATCC NO, HTB-26); MCF7 (Human breast adenocarcinoma cell line, ATCC NO, HTB-22); ACHN (Human renal cell adenocarcinoma cell line, ATCC NO, CRL-1611); PC-3M (Human prostate adenocarcinoma cell line, ATCC NO CRL-1435); HL60 (Human acute promyelocytic leukemia cell line, ATCC NO, CCL-240); THP-1 (Human acute monocytic leukemia, ATCC NO, TIB-202); Jurkat (Human acute T cell leukemia cell line, ATCC NO, CRL-2063); HCT-116 (Human colorectal carcinoma cell line, ATCC NO, CCL-247); HT-29 (Human colorectal adenocarcinoma cell line, ATCC NO, HTB-38™); WI-38 (Human normal lung cell line, ATCC NO, CCL-75); MRC-5 (Human normal lung cell line, ATCC NO, CCL-171).

HepG2, MDA-MB-231, WI-38 and MRC-5 cells were obtained from Shanghai Institute of Cell Biology, Chinese Academy of Sciences (Shanghai 200031, China). A549, HeLa, K562, MCF7, ACHN, H460, U2OS, Eca-109, MCF7, HL60, THP-1, Jurkat, HCT-116, HT-29, PC-3M, SK-MEL-28, Molt-4, H460 and ACTIN cells were purchased from ATCC (American Type Culture Collection, USA).

Standard 72 h MTT (thiazolye blue; 3-[4,5-dimethylthiazol-2-yl]-2,5-diphenyltetrazolium bromide) assays were performed. Briefly, the cell lines used in this study were recovered and cultured according to the conditions recommended. 4000 cells per well were seeded into 96-well plates according to doubling time and incubated overnight at 37° C. Compounds were prepared in DMSO and a ½ dilution series in 100 µl cell culture media, added to cells (in duplicates) with the final DMSO concentration of 0.025%, and incubated for 72 hrs at 37° C. MTT solution (5 mg/ml) was added at 10 µl per well and incubated in the dark at 37° C. for 4 hr. Culture medium and MTT solution was removed. MTT dye was solubilised with 100 µl per well of DMSO with agitation. Absorbance was read at 562 nm and data analyzed using Sigmoid curve-fitting software Origin 6.0 (MicroCal, LLC, USA) to determine IC$_{50}$ value. Anti-proliferative activity of representative compounds disclosed herein is presented in Table II.

TABLE II

| | Anti-proliferative activity | | | | | | | | | |
|---|---|---|---|---|---|---|---|---|---|---|
| | Cytotoxicity, MTT 72 hrs, $IC_{50}$ μM | | | | | | | | | |
| Comp. No. | HeLa | A549 | U2OS | Eca-109 | HepG2 | K562 | MCF7 | SK-MEL-28-luc | Molt-4-luc | H460-luc |
| 1 | 4.70 | 6.03 | 5.99 | 14.25 | 4.55 | 4.78 | 10.13 | 6.47 | 6.40 | 6.19 |
| 2 | 4.93 | 8.29 | 7.33 | 14.50 | 5.97 | 6.17 | 9.56 | 6.37 | 6.30 | 6.39 |
| 15 | 10.37 | 4.98 | 7.44 | 20.00 | 1.16 | 9.81 | 0.12 | 9.43 | 2.46 | 4.98 |
| 16 | 14.25 | 3.33 | 7.42 | 12.87 | 1.6 | 7.68 | 2.17 | 8.51 | 3.82 | 4.06 |
| 17 | 4.22 | 2.19 | 4.91 | 6.06 | 1.19 | 2.31 | 4.93 | 5.48 | 6.29 | 2.49 |
| 18 | 1.7 | 1.21 | 3.07 | 11.67 | 0.68 | 6.69 | 0.71 | 8.59 | 1.05 | 1.27 |
| 19 | 4.33 | 3.43 | 9.54 | >10 | 1.41 | 15.43 | 3.96 | >10 | 6.66 | 3.63 |
| 20 | 5.55 | 3.07 | >10 | >10 | 1.81 | 6.11 | >10 | 7.79 | 3.43 | >10 |
| 22 | 1.67 | 2.82 | 2.13 | 3.40 | 0.70 | 1.42 | 1.13 | 2.72 | 2.45 | 1.11 |
| 24 | 1.6 | 3.69 | 3.30 | 5.30 | 1.32 | 3.68 | 3.48 | 3.05 | 4.51 | 1.41 |
| 39 | 3.3 | 0.42 | 1.26 | 3.70 | 0.10 | 4.72 | >10 | 3.41 | 5.25 | 1.03 |
| 42 | 9.93 | 1.73 | 1.86 | 10.52 | 0.55 | >10 | >10 | 9.45 | 4.79 | 2.00 |
| 73 | 0.23 | 0.37 | 0.41 | >10 | 0.18 | 0.61 | 0.45 | 0.49 | 0.43 | 0.315 |
| 96 | 0.15 | 0.12 | 0.23 | >10 | 0.25 | 0.22 | 0.25 | 0.26 | 0.22 | 0.26 |
| 102 | 0.49 | 0.57 | 0.57 | 3.52 | 0.50 | 1.44 | 1.3 | 0.99 | 0.23 | 0.22 |
| 111 | 0.01 | 0.01 | 0.03 | 0.05 | 0.58 | 0.03 | 0.08 | 0.01 | 0.01 | 0.006 |
| 112 | 0.0004 | 0.03 | 0.01 | 0.01 | 0.47 | 0.0011 | 0.0014 | 0.0038 | 0.02 | 0.02 |

| | Cell Viability IC50: μM | | | | | | | | | |
|---|---|---|---|---|---|---|---|---|---|---|
| Comp. No. | MDA-MB-231-luc | ACHN-luc | PC-3M-luc | HL-60 | THP-1 | Jurkat | HCT 116 | HT-29 | WI-38 | MRC-5 |
| 1 | 6.33 | 9.82 | ND | ND | ND | ND | ND | ND | >10 | ND |
| 2 | 6.16 | 23.44 | ND | ND | ND | ND | ND | ND | >10 | ND |
| 15 | 5.94 | 7.81 | 10.5 | ND | ND | ND | ND | ND | >10 | ND |
| 16 | 5.27 | 7.38 | 5.11 | ND | ND | ND | ND | ND | >10 | ND |
| 17 | 2.63 | 2.45 | ND | ND | ND | ND | ND | ND | >10 | ND |
| 18 | 3.30 | 2.98 | 3.55 | 1.85 | 5.37 | 1.31 | 2.1 | 0.81 | 11.10 | 13.33 |
| 19 | 8.51 | 3.46 | ND | ND | ND | ND | ND | ND | >10 | ND |
| 20 | 4.68 | >10 | >10 | 3.41 | 2.08 | 3.42 | >10 | 2.93 | ND | 15.13 |
| 22 | ND | 3.74 | 3.19 | 2.09 | 3.26 | 1.47 | 1.89 | 1.46 | ND | 5.17 |
| 24 | ND | 5.58 | 5.02 | 3.49 | 5.25 | 1.79 | 3.43 | 1.35 | >10 | 3.88 |
| 39 | 2.03 | 13.69 | >10 | 1.27 | 2.95 | 1.12 | 3.46 | 0.15 | ND | 3.97 |
| 42 | 1.28 | >10 | 4.06 | 1.14 | 1.04 | 0.36 | 3.36 | 0.20 | ND | 14.57 |
| 73 | 0.44 | 0.51 | 0.89 | 0.43 | 2.74 | 0.40 | 0.28 | 1.16 | >10 | 3.36 |
| 96 | ND | 0.34 | 0.48 | 0.37 | 0.36 | 0.22 | 0.32 | 0.48 | >10 | 0.89 |
| 102 | 0.75 | 0.62 | 1.13 | 0.23 | 0.41 | 0.69 | 0.28 | 0.45 | ND | 1.63 |
| 111 | 0.03 | 0.06 | 0.006 | 0.01 | 0.01 | 0.0054 | 0.004 | 0.02 | ND | 0.06 |
| 112 | ND | 0.037 | 0.027 | 0.008 | 0.004 | 0.0025 | 0.005 | 0.05 | >10 | >10 |

ND-NotDetermined

Example 30

Xenograft Studies

Female BALB/c nude mice from SHANGHAI SLAC LABORATORY ANIMAL CO with age of 5 to 6 weeks and body weight of 19 to 20 g were used in the study. Autoclaved water and irradiated food were provided ad libitum, and animals were maintained on a 12-hour light and 12-hour dark cycle. Cages, bedding, and water bottles were autoclaved before use and changed weekly. The health of all animals was determined by daily gross observation of experimental animals, and analyses of blood samples of sentinel animals housed on shared shelf racks. All animals were allowed to acclimate and recover from any shipping-related stress for a minimum of 72 hours before experimental use. All animal experiments were conducted according to the guidelines of Chinese.

Xenograft tumor models were established with human tumor cell lines. HT-29 (Human colon cancer cell), H460 (Human large cell lung cancer cell line), Molt-4 (Human acute lymphoblastic leukemia cell line), PC-3M (Human prostate adenocarcinoma cell line) and HL60 (Human acute promyelocytic leukemia cell line), purchased from ATCC were used in this study. Briefly, mice were anesthetized by gas anesthesia (3% isoflurane), then tumor cells diluted in 100 μl DPBS mixed with Matrigel 1:1 were injected subcutaneously into the dorsal region near the thigh of the mouse. Tumor growth was monitored twice per week until the tumor reached to a volume of 100 mm³. The day before the first administration of a compound, tumor bearing animals were stratified into several groups according to tumor volume. Only animals with appropriate tumor volumes were selected and randomly distributed to treatment and control groups. Each group consisted of 8 mice.

The test compounds were dissolved in a buffer containing 5% NMP, 15% PEG400 and 80% 0.1M tartrate buffer (pH=4.0). Solutions were prepared fresh daily. The test compounds were given by i.p, qd. The test compounds were administrated at dosage of 12.5 mg/kg, 25 mg/kg/day, 50 mg/kg/day and 100 mg/kg/day over 21 days. Control mice received vehicle using the same administration schedule as that of the test compound.

Mortality checks were conducted daily. Body weight of the mice was determined twice a week. All animals were individually followed throughout the experiment. Weight loss was calculated as percentage change in mean group body weight using the following formula: $[(W-W0)/W0] \times 100$, where 'W' represents mean body weight of the treated group at a particular day and 'W0' represents mean body weight of the same treated group at initiation of treatment. Tumor volumes (in mm3) were calculated after 21 days drug administration. The calculation was used as the following ellipsoid formula: [D×(d2)]/2, where 'D' represents the large diameter of the tumor and 'd' represents the small diameter. Statistical analysis is done using the rank sum test and one-way ANOVA and a post hoc Bonferroni t test (SigmaStat version 2.0, Jandel Scientific, San Francisco, Calif.). Differences between groups are considered significant when P<0.05.

Administrations of compound 18 and compound 102 in xenograft mice showed anti-tumor activities at the dosage from 12.5 mg/kg to 100 mg/kg. The effects were significant with p<0.05 (T-test).

The synergistic action or enhancement of conventional chemotherapeutic agent by a test compound can also be determined with this model by comparing animals treated with the standard therapy alone to animals treated with test compound plus the same standard therapy. An additive effect on the delay of tumor growth will be observed if synergistic action due to test compound is occurring.

Example 31

Pharmacokinetic Determination

Male Sprague-Dawley rats were maintained on food and water ad libitum. They were housed in an individual ventilated caging system. The test compound at a dose of 5 mg/kg and 20 mg/kg was given i.v. and orally to SD rats respectively (3 animals per group). The appropriate quantity compound with free base (Wt.: 346.1) was accurately weighted into a tube and dissolved in NMP, vortexed to get a clear solution. 0.015N HCl in Saline was added and the solution was vortexed to yield a clear and colorless solution at 1 mg/mL for both intravenous and oral administration. The concentration of the test compound in the dosing solution was reconfirmed by HPLC method. Then the test compound (10, 100 mg/kg) was given orally in a volume of 0.1 mL/10 g body weight to SD rats. Plasma samples were collected from retro-orbital puncture at pre-dose and 0.083, 0.25, 0.5, 1, 2, 4, 6, 8, and 24 hours post-dose. All samples and the dose formulation were stored at −20° C. until bioanalysis. The concentrations of the test compound in plasma were determined using a high performance liquid chromatography/mass spectrometry (HPLC/MS/MS) method.

Example 32

Pancreatic Cancer Clinical Trial

Length of Study
  8 months [length of time from FPV to LPV]
Objectives
  The primary objective of this study is to determine the objective response rate (ORR) for compound of Formula (I) when administered every 2 weeks to patients with adenocarcinoma of the pancreas. The secondary objectives of this study is to measure time-to-event variables including: time to objective tumor response for responding patients (TtOR), duration of response for responding patients, time to treatment failure (TtTF), time to progressive disease (TtPD), progression-free survival (PFS), overall survival (OS); the toxicities of therapy.

Study Design
  The study is a multi-center, double-blind, randomized, placebo-controlled Phase 2 study. Tumor assessments will be repeated every 4 cycles (approximately 8 weeks). Patients will receive study therapy for 12 treatments, or until tumor progression is documented, unacceptable toxicity is experienced, the patient withdrew consent, or the patient is unable to fulfill the responsibilities of study participation as determined by the treating physician or the qualified investigator. After study discontinuation, patients who have not progressed will have tumor assessments performed approximately every 8 weeks until disease progression. Once patients have disease progression, patients will enter a post-study follow-up period, and will be followed every 12 weeks for 24 months for overall survival. Patients will also be followed for ongoing or any new toxicities.
Diagnosis and Main Criteria for Inclusion
  Male and females ≧18 years of age will be eligible for this study if they are diagnosed with adenocarcinoma of the pancrease. Patients must have had as their initial presentation pancreatic metastasis without evidence of pulmonary metastasis.
  Main inclusion criteria will include: histologically proven adenocarcinoma; performance Status of 0 or 1 on the Eastern Cooperative Oncology Group (ECOG) scale; a complete history and physical, chest x-ray, CT scan of abdomen and pelvis; barium enema, or colonoscopy. Patients with pain will be requires to have had their pain stabilized for 1 week prior to commencing therapy. Patients requiring opioids for pain control will be required to have been on a fixed analgesic regimen aimed to provide adequate pain control with no more than three breakthrough (supplemental) doses of analgesics per day to control pain. Patients will be requires to demonstrate adequate bone marrow reserve (i.e. Neutrophil count≧1.5×$10^9$ cells/L; Platelets≧100×$10^9$ cells/L). Patients will be required to have negative tumor markers for alpha-fetoprotein (AFP) and monoclonal antichorionic gonadotropin (β-subunit) (βHCG). Patients will be required to demonstrate at least one unidimensionally measurable lesion, meeting Response Evaluation Criteria in Solid Tumors (RECIST). Patient will also be required to have an estimated life expectancy of at least 12 weeks.
  Main exclusion criteria will include: prior chemotherapy; pregnancy or breastfeeding; inability or unwillingness to take folic acid, vitamin B12 supplementation, or dexamethasone.
Study Drug, Dose, and Mode of Administration
  Compound of Formula (I) dosage will be 500 mg/$m^2$ and will be given as a 10-minute infusion on Day 1 of each 14-day cycle. Folic acid and vitamin B12 supplementation, and dexamethasone (or equivalent corticosteroid) prophylaxis will also be administered.
Variables
  Efficacy: Tumor response rate will be defined as the number of patients with documented partial response (PR) or complete response (CR) divided by the number of patients qualified for tumor response analysis. Time-to-event analyses will be performed on the observed distributions of time to objective progressive disease, progression-free survival (PFS), time to treatment failure (TtTF), and overall survival (OS) using the Kaplan-Meier (K-M) method. All patients with best overall response of CR or PR will be analyzed for response duration by using the K-M method.
  Safety: Safety analyses will include adverse event (AE) rates, serious AEs, vital signs, laboratory data, blood transfusions required, and deaths. Toxicities using laboratory and non-laboratory adverse events will be evaluated using the common terminology criteria for adverse events (CTCAE, version 3.0).

Evaluation Methods

Statistical: The primary analysis will be to estimate the objective best overall response rate and its 95% confidence interval (CI). Medians for each of the time-to-event endpoints, and time-to-event variables will be estimated using the K-M method. All estimates of treatment effects will be conducted at a two-sided alpha level of 0.05, and CI for all parameters will be estimated were to be constructed using a 95% level.

Example 33

Clinical Trial Protocol of Compound of Formula (I) in Patients with Previously Untreated Advanced Soft Tissue Sarcoma Patient Eligibility Patients with documented metastatic or locally advanced soft tissue sarcoma, not curable by other means, are eligible for this trial. Eligibility criteria were as follows: histologically documented soft tissue sarcoma; presence of at least one site of unidimensionally measurable clinically and/or radiologically documented disease; age $\geq 18$ years, life expectancy of at least 12 weeks; Eastern Cooperative Oncology Group performance status $\leq 2$; and no prior systemic therapy for metastatic disease. Prior adjuvant chemotherapy is permitted as long as treatment had been completed $\geq 6$ months since the last dose of therapy. Patients could not have received radiotherapy to the sole site of measurable disease unless it was a current site of progressive disease, and no more than 25% of functioning bone marrow could have been irradiated. Previous surgery is allowed if $\geq 4$ weeks prior to initiating treatment. Laboratory requirements include the following: absolute granulocyte count $\geq 1.5 \times 10^9$/L; platelet count $\geq 100 \times 10^9$/L; AST$\leq 2.5 \times$ upper normal limit (UNL); serum creatinine$\leq$UNL; bilirubin$\leq$UNL. All patients must give informed consent according to the requirements of their local Institutional and/or University Human Experimentation Committee.

Treatment

Compound of Formula (I) is prepared as a sterile 10 mg/ml solution. The individually calculated dose is diluted prior to infusion with 0.9% sodium chloride injection USP or 5% dextrose injection USP to final concentrations ranging from 0.09 to 0.5 mg/ml of compound of Formula (I).

Compound of Formula (I) is administered in the outpatient setting as a 1 hour infusion at a dose of 50 mg/m$^2$ daily×3 days every 21 days. Vital signs are monitored every 30 minutes×5 beginning at the start of infusion until 1 hour post infusion. Antidiarrheal prophylaxis and antiemetic prophylaxis are prescribed as follows: 4 chewable Pepto Bismol tablets 1 hour before first dose of compound of Formula (I), then 2 tablets every 6 hours until 12 hours after the last dose of compound of Formula (I) (day 3), ondansetron 8 mg orally every 12 hours beginning 12 hours before treatment and continuing until 12 hours after the last dose of compound of Formula (I) (day 3). Loperamide is started if diarrhea occurred, using a dose regimen of 2 mg orally q.2 h while awake and q.4 h during sleep until 12 h diarrhea-free. Dose reductions are allowed (dose level: 1=37.5 mg/m$^2$/d, dose level: 2=28 mg/m$^2$/d), if the following toxicities are seen: diarrhea$\geq$grade 3 associated with mucus or dehydration; nausea and vomiting$\geq$grade 3 despite antiemetics; granulocyte nadir <0.5×10$^9$/L and/or neutropenia with fever or infection; platelet nadir <25×10$^9$/L and/or thrombocytopenic bleeding; or any nonhematologic toxicity (except alopecia) $\geq$grade 3. Patients requiring more than two dose reductions are removed from protocol treatment.

Treatment continues until progression, or for 2 cycles after complete or stable partial response. Nonresponding stable patients continue on treatment until progression, or alternatively are removed from therapy after 6 cycles at the investigator's discretion. After termination from protocol treatment, all patients are seen at 4 weeks, then every 3 months until progression or death.

Response and Toxicity Assessment

Patients are considered evaluable for response if they have received at least 1 cycle of therapy and have their disease reevaluated. Patients are evaluated for response every 6 weeks (every 2 cycles) using the same investigations that demonstrated measurable disease at baseline. Response and progression are evaluated using the RECIST criteria (response evaluation criteria in solid tumors) (Therasse P, Arbuck S G, Eisenhauer E A, et al. New guidelines to evaluate the response to treatment in solid tumors (RECIST guidelines). Journal of the National Cancer Institute. 2000; 92(4205-216).

Patients are considered evaluable for toxicity after their first infusion of compound of Formula (I). A history and physical examination is performed on day 1 of each cycle with an assessment of toxicity during the previous treatment interval. CBC, platelets, differential, bilirubin and AST are performed on days 1, 8, and 15, and BUN, creatinine, electrolytes, LDH, fasting glucose, and alkaline phosphatase are performed on day 1 of each cycle. Toxicities are graded according to the NCI Common Toxicity Criteria Version 2.0.

Statistical Analysis

The primary endpoint of this phase II study is objective response rate, with secondary endpoints of toxicity, time to progression, early progression rate, and response duration. In order to minimize the expected number of patients treated in the event that the regimen proves to be very disappointing or very successful, a two-stage design is used for patient accrual. This design tests the null hypothesis ($H_0$) that the true response rate is <5% versus the alternative hypothesis ($H_A$) that the true response rate is >20%. The significance level (i.e., the probability of rejecting $H_0$ when it is true) is 0.058. The power is 0.865 when the true response probability is 20%. If there were no responses after the first 15 patients, the response rate is concluded to be <5% and accrual was to be stopped. If there were one or more responses, accrual is continued to 30 evaluable patients.

Example 34

Metastatic Adenocarcinoma of the Prostate Clinical Trial

Eligibility

All patients are required to have histologically confirmed metastatic adenocarcinoma of the prostate that was progressive despite an adequate trial of hormonal therapy. Patients are ambulatory with an Eastern Cooperative Group performance status of 0-2 and have an estimated life expectancy of at least 3 months. One prior secondary hormonal agent is allowed, but it must have been discontinued at least 4 weeks before to exclude an antiandrogen withdrawal response. No prior chemotherapy, experimental therapy, strontium, or suramin therapy is allowed. Prior radiation therapy is permitted provided that at least 4 weeks had elapsed from the day of the last treatment. Patients who did not have an orchiectomy are continued on their luteinizing hormone-releasing hormone injections, but no other hormonal agent is allowed while on study. Other requirements include: adequate bone marrow function with absolute neutrophil count≧1200/µl, hemoglobin≧8 g/day, and platelets≧100,000/µl; stable renal function with creatinine ≦1.5 upper limits of normal; and adequate hepatic reserve with bilirubin ≦1.5 and aspartase aminotransferase ≦2.5 times the upper limit of normal. A prostate-specific antigen (PSA) ≧10 ng/ml is required if the patient has bone only metastases. No serious concurrent illnesses, previous or concurrent malignancy (except nonmelanoma skin cancer treated with curative intent; other cancers allowed only if the patient has been disease free for 5 years), or history of central nervous system metastasis is allowed. A written informed consent is obtained from all patients before registration.

Treatment.

On the basis of Phase I trial, compound of Formula (I) is initially administered via a battery-powered ambulatory infusion pump connected to a central venous catheter as a 72-h continuous infusion at the starting dose of 40 mg/m2/day. The compound of Formula (I) cassette is changed daily with courses repeated every 14 days until disease progression or overt toxicity. For patients completing two courses at 40 mg/m2/day without ≧grade 3 toxicity (except alopecia), their dose could be escalated to 50 mg/m2/day at the discretion of the investigator. If the subsequent two courses are again tolerated, another dose escalation to 60 mg/m2/day could be performed. All patients who are undergoing dose escalation are required to use antidiarrheal prophylaxis with loperamide with/without questran. For all patients experiencing a grade ≧2 increase in creatinine, grade ≧4 hematological toxicity, or other grade ≧3 toxicity, the infusion is held until resolution of the toxicity to grade ≦1, at which time, the drug is resumed at the next lowest dose level (the lowest level allowed was 30 mg/m2/day). If the toxicity does not resolve by day 14, the patient is removed from the study. For nausea/vomiting and diarrhea, no dose reduction is performed unless the toxicities persisted despite maximal antiemetic and antidiarrheal prophylaxis. No dose re-escalation is allowed.

End Points

The primary end points of this study are response rate and toxicity. After the baseline assessments, the complete blood counts and serum chemistries are repeated weekly for the first month, then at the beginning of each new course (every 2 weeks) of therapy. Vitals signs, performance status, and toxicity are also assessed weekly for the first month and then at the beginning of each additional course of therapy as well. PSA is obtained every 4 weeks, and computed tomography scans and/or bone scans were repeated every 12 weeks while on study. All patients receiving compound of Formula (I) are considered evaluable for toxicity (using National Cancer Institute Common Toxicity Criteria, version 1.0), but only those patients completing at least four courses of therapy (8 weeks) are considered evaluable for response. Any patients receiving less than four cycles of therapy (unevaluable for response) are replaced because it is felt that <8 weeks of drug is inadequate to evaluate for any potential objective response using a cytostatic agent. A CR is defined as disappearance of all measurable disease and normalization of the bone scan for 4 weeks. A PR is defined as ≧50% decrease from baseline in the sum of the products of the maximum perpendicular diameters for indicator lesions with no progressive disease observed for at least 4 weeks. For patients with bone scan only abnormalities, a PR requires ≧50% decrease in the number of lesions. Stable disease (SD) is defined as the absence of a CR, PR, or disease progression. Progressive disease (PD) is defined as unequivocal increase of at least 25% in the size of any measurable lesion or the appearance of any new lesion. Serum PSA levels are not used in the response assessment.

Statistical Methods

Progression-free survival (PFS) is used as the primary end point. Survival probabilities were calculated by the method of Kaplan and Meier (Kaplan E., Meier R. Nonparametric estimation from incomplete observations. J. Am. Stat. Assoc., 53: 457-481, 1958).

Example 35

Pharmaceutical Compositions

Example 35a

Parenteral Composition

To prepare a parenteral pharmaceutical composition suitable for administration by injection, 100 mg of a water-soluble salt of a compound of Formula (I) is dissolved in DMSO and then mixed with 10 mL of 0.9% sterile saline. The mixture is incorporated into a dosage unit form suitable for administration by injection.

Example 35b

Oral Composition

To prepare a pharmaceutical composition for oral delivery, 100 mg of a compound of Formula (I) is mixed with 750 mg of starch. The mixture is incorporated into an oral dosage unit for, such as a hard gelatin capsule, which is suitable for oral administration.

Example 35c

Sublingual (Hard Lozenge) Composition

To prepare a pharmaceutical composition for buccal delivery, such as a hard lozenge, mix 100 mg of a compound of Formula (I) with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 35d

Fast-Disintegrating Sublingual Tablet

A fast-disintegrating sublingual tablet is prepared by mixing 48.5% by weigh of a compound of Formula (I), 44.5% by weight of microcrystalline cellulose (KG-802), 5% by weight of low-substituted hydroxypropyl cellulose (50 µm), and 2% by weight of magnesium stearate. Tablets are prepared by direct compression (*AAPS PharmSciTech.* 2006; 7(2):E41). The total weight of the compressed tablets is maintained at 150 mg. The formulation is prepared by mixing the amount of compound of Formula (I) with the total quantity of microcrystalline cellulose (MCC) and two-thirds of the quantity of low-substituted hydroxypropyl cellulose (L-HPC) by using a three dimensional manual mixer (Inversina®, Bioengineering AG, Switzerland) for 4.5 minutes. All of the magnesium stearate (MS) and the remaining one-third of the quantity of L-HPC are added 30 seconds before the end of mixing.

Example 35e

Inhalation Composition

To prepare a pharmaceutical composition for inhalation delivery, 20 mg of a compound of Formula (I) is mixed with 50 mg of anhydrous citric acid and 100 mL of 0.9% sodium chloride solution. The mixture is incorporated into an inhalation delivery unit, such as a nebulizer, which is suitable for inhalation administration.

Example 35f

Rectal Gel Composition

To prepare a pharmaceutical composition for rectal delivery, 100 mg of a compound of Formula (I) is mixed with 2.5 g of methylcelluose (1500 mPa), 100 mg of methylparapen, 5 g of glycerin and 100 mL of purified water. The resulting gel mixture is then incorporated into rectal delivery units, such as syringes, which are suitable for rectal administration.

Example 35g

Topical Gel Composition

To prepare a pharmaceutical topical gel composition, 100 mg of a compound of Formula (I) is mixed with 1.75 g of hydroxypropyl cellulose, 10 mL of propylene glycol, 10 mL of isopropyl myristate and 100 mL of purified alcohol USP. The resulting gel mixture is then incorporated into containers, such as tubes, which are suitable for topical administration.

Example 35h

Ophthalmic Solution Composition

To prepare a pharmaceutical opthalmic solution composition, 100 mg of a compound of Formula (I) is mixed with 0.9 g of NaCl in 100 mL of purified water and filtered using a 0.2 micron filter. The resulting isotonic solution is then incorporated into ophthalmic delivery units, such as eye drop containers, which are suitable for ophthalmic administration.

Example 35i

Nasal Spray Solution

To prepare a pharmaceutical nasal spray solution, 10 g of a compound of Formula (I) is mixed with 30 mL of a 0.05M phosphate buffer solution (pH 4.4). The solution is placed in a nasal administrator designed to deliver 100 of spray for each application.

Example 36

CDK9 Inhibitory Activity

Kinase assays. The compounds were tested for their ability to inhibit kinases. Kinase activity of representative compounds is presented in Table III.

TABLE III

| Compound | | F200 | SG48 | SG49 | SG50 | SG51 | SG52 | SG53 | SG54 |
|---|---|---|---|---|---|---|---|---|---|
| Target bio-chemical activity IC50 (nM) | CDK1 | 624 | 90 | 190 | 180 | 0.4 | 70 | 6840 | >10000 |
| | CDK2 | 3 | 4 | 16 | 4 | 0.5 | 30 | >10000 | 1670 |
| | CDK5 | 271 | 100 | 350 | 190 | 0.5 | 25 | >10000 | >10000 |
| | CDK7 | 146 | 3280 | >10000 | >10000 | 43 | 1950 | >10000 | >10000 |
| | CDK9 | 13 | 79 | 95 | 24 | 0.6 | 0.4 | 41 | 57 |
| | Aurora A | 30 | 800 | 2460 | 1280 | 50 | 1650 | 98 | 620 |
| | Aurora B | 700 | 930 | >10000 | >10000 | 59 | 1000 | 190 | 320 |
| | SRC | 1050 | >10000 | 4560 | >10000 | 200 | 3930 | >10000 | >10000 |
| | TSSK1 | >10000 | 140 | 1490 | 520 | 1.6 | >10000 | >10000 | >10000 |
| Cellular effect in mammalian cells IC50 (mM)) | HeLa | 1.7 | 3.31 | 2.69 | 0.23 | <0.1 | 0.49 | 9.93 | 3.3 |
| | MCF-7 | 0.71 | 9.4 | >10 | 0.45 | <0.1 | 1.3 | >10 | >10 |
| | H460 | 1.27 | 4.66 | 2.95 | 0.315 | <0.1 | 0.22 | 2.00 | 1.03 |
| | Jurkat | 1.31 | 1.92 | 0.61 | 0.4 | 0.005 | 0.69 | 0.36 | 1.12 |
| | THP-1 | 5.3 | >10 | 3.68 | >10 | ND | 0.41 | 1.04 | 2.95 |
| | K562 | 6.69 | 4.75 | 3.52 | 0.61 | 0.03 | 1.44 | >10 | 4.72 |
| | Molt-4 | 1.05 | ND | ND | ND | ND | ND | ND | ND |
| | HCT116 | 2.1 | 4.67 | 4.28 | 0.28 | 0.004 | 0.28 | 3.56 | 3.46 |
| | HepG2 | 0.68 | 6.1 | 5.55 | 0.41 | 0.03 | 0.57 | 1.86 | 1.26 |
| | HT29 | 0.59 | 8.31 | 8.59 | 1.16 | 0.02 | 0.45 | 0.25 | 0.15 |
| | MRC-5 | ND | >10 | 5.82 | 3.36 | <0.1 | 1.63 | >10 | 3.97 |
| | L02 | 4.3 | 8.1 | 7.34 | >10 | 0.02 | 1.40 | >10 | 8.37 |

Kinase inhibitory activities :
F200 = SG45 = Compound 18 in Table 3;
SG48 = Compound 72 in Table 4;
SG49 = Compound 70 in Table 4;
SG50 = Compound 73 in Table 4;
SG51 = Compound 111 in Table 4;
SG52 = Compound 102 in Table 4;
SG53 = Compound 42 in Table 3;
SG 54 = Compound 39 in Table 3;
ND-Not Determined

Example 37

Compound 18 (F200 or SG45) Induces Cell Apoptosis Assay

Figure 2:
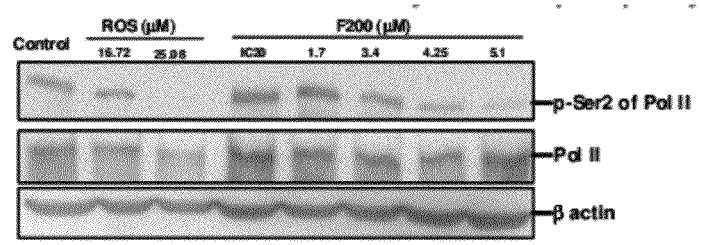
FIG. 2 showed that compound 18 inhibited CDK9's activity on Pol IIphosphorylation.

MCF-7 cells were treated with compound 18 (F200) and Roscovitine for 48 hours. Then the cells were analyzed by TUNEL assay and Western blot to detect apoptosis.
For TUNEL assay, cells were fixed and blocking in 6-well plate. DNA strand breaks were labeled by terminal deoxynucleotidyl transferase (TdT), which catalyzed polymerization of labeled nucleotides to free 3'-OH DNA ends in template-independent manner Fluorescein could be detected by anti-fluorescein antibody, conjugated with horse-radish-peroxidase (POD). After DAB reaction, stained cells were analyzed and counted under light microscope.
For Western blot, cells were harvested and lysed by lysis buffer. Western blot were performed with anti-PARP or anti-Pol(DNA polymerase) II antibody. During apoptosis, PARP is cleaved from a 113 KD intact form into smaller 89 KD and 24 KD fragments.
Results are shown in FIGS. 1 and 2.
It showed that compound 18 inhibited CDK9's activity on Pol II phosphorylation and induced apoptosis of cells.

Example 38

Acute Toxicity & Pharmacokinetic Determination

Preliminary toxicology study in mice: Mice were divided into four groups (n=10 in each), 500 mg/kg, 1,000 mg/kg or 2,000 mg/kg were administered respectively to three groups by gavage. Negative control is 0.5% CMC-Na. After two weeks, mice were sacrificed and tissue section of visceral organs were analyzed by Hematoxylin-Eosin staining. Results: LD50>2000 mg/kg (p.o.) MTD>500 mg/kg (p.o.)
These results demonstrated that Compound 18 has excellent tolerability in animals.

TABLE IV

| PK profile of compound 18 (SG45 or F200): rat IV/PO study | | | | | | | | |
|---|---|---|---|---|---|---|---|---|
| | $AUC_{(0-t)}$ μg/L * hr | $AUC_{(0-\infty)}$ μg/L * hr | $MRT_{(0-\infty)}$ hr | $t_{1/2}$ hr | $T_{max}$ hr | Vz L/kg | CL L/hr/kg | $C_{max}$ ng/mL | F* % |
| IV (5 mg/kg) | 543.18 | 544.96 | 0.67 | 0.70 | 0.083 | 9.60 | 9.38 | 962.51 | |
| PO (20 mg/kg) | 1466.73 | 1486.74 | 1.67 | 1.24 | 0.58 | NA | NA | 895.39 | 67.51 |

This result showed that compound 18 has good oral availability and t 1/2 after oral administration.

Example 39

Inhibition of Tumor Cell Growth by Compound 18 (SG45 or F200)

Animal: SCID-bg mice
Tumor type: lung carcinoma (H460)
Treatment: Single PO dose for 21 days (starting at day 7 following tumor inoculation)
Endpoint: tumor volume and mean luciferase activity by Xenogen (Caliper) machine:
SCID-bg mice were implanted with NCI-H460 cells at 5×10⁶ cells/mouse on Day 0. Compound 18 treatment began on Day 7. Animals were administered orally once a day with 20 or 100 mg/kg compounds dissolved in vehicle (0.5% carboxymethylcellulose sodium) on Day 7 to Day 21. In model group, the vehicle was used instead of compound 18. Tumor volume and mean luciferase activity by Xenogen technology were measured once per there days.

TABLE V

| Tumor growth inhibition | |
|---|---|
| | % Tumor Growth Inhibition at Day 21 |
| Compound 18 (20 mg/kg) | 41.3% |
| Compound 18 (150 mg/kg) | 56.5% |

It showed that compound 18 was able to inhibit turmor growth via apoptosis induction at 150 mg/kg after oral administration.

Example 40

Induction of Neutrophil Apoptosis by Compound 18 (SG45 or F200)

1. Acquire 5-10 ml blood from adult rabbit
2. Isolate neutrophils using RED BLOOD CELL LYSING BUFFER (SIGMA Cat No. R7757) and rabbit isolation kit (TBDsciences, Cat No. LZS11133)
3. Treat neutrophils with reference compounds or SG45 for 15 h
4. Apoptosis assay (Annexin-V and PI staining)

Figure 3A:
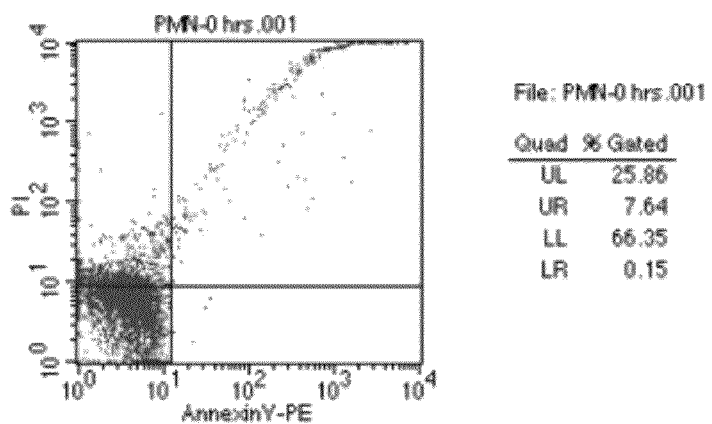
FIG. 3 showed time diagram of rabbit neutrophil apoptosis, including which FIG. 3A showed the cells at the beginning of isolation, FIG. 3B showed the cells at 24 hours after isolation, FIG. 3C showed the cells at 48 hours after isolation, and FIG. 3D showed the percentage of neutophil apoptosis vs the time after isolation.
Figure 3B:
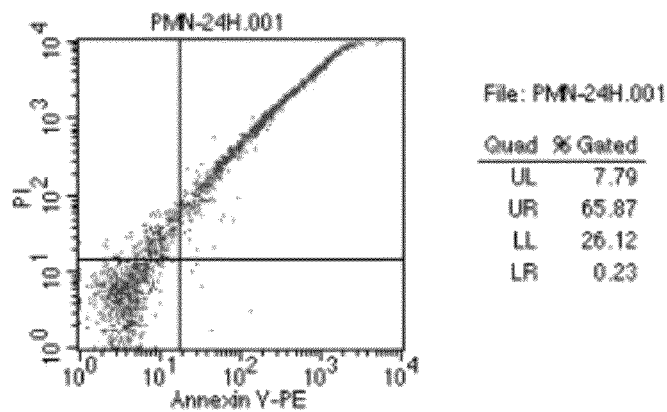
Figure 3C:
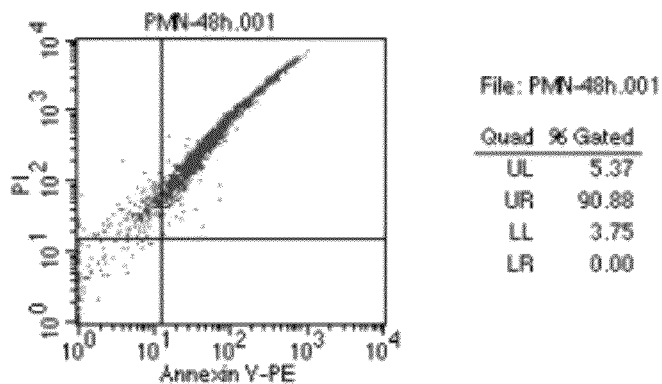
Figures 3, 3D:
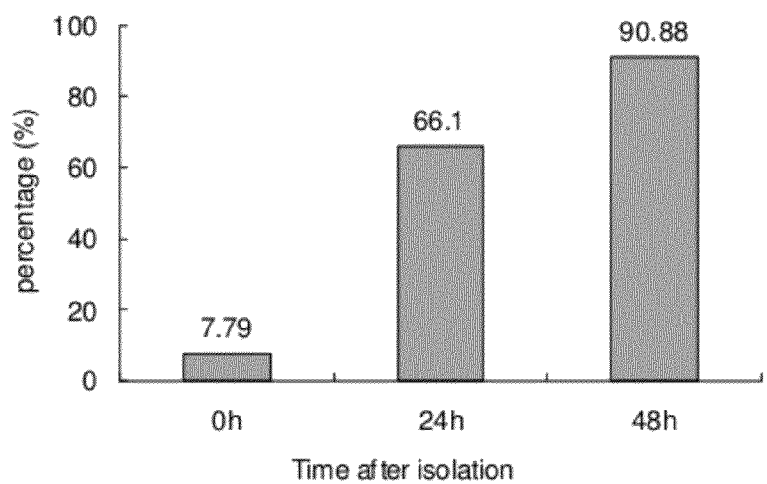
Figures 4, 4H:
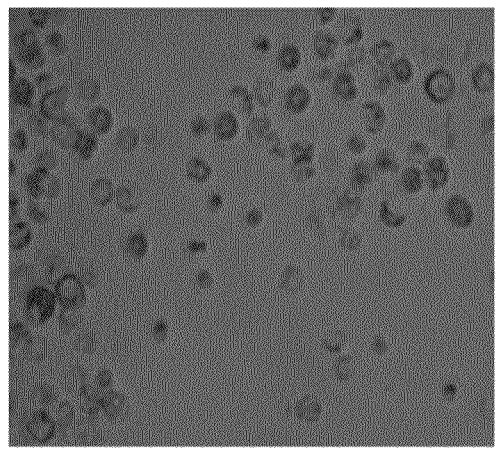
FIG. 4 showed neutophil apoptosis induced by different compounds (×40), including which FIG. 4A showed the effect of negative control, FIG. 4B showed the effect of LPS (lipopolysaccharide) (1 μg/mL), FIG. 4C showed the effect of LPS (5 μg/mL), FIG. 4D showed the effect of LPS (10 μg/mL), FIG. 4E showed the effect of compound 18 (0.5 μM), FIG. 4F showed the effect of compound 18 (2 μM), FIG. 4G showed the effect of compound 18 (10 μM), and FIG. 4H showed the effect of Roscovitine (20 μM).
Figure 5A:
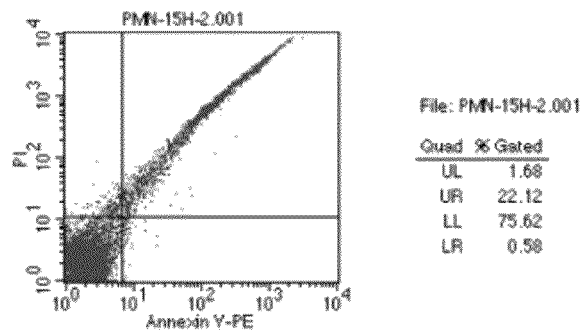
FIG. 5 showed comparison of the effect of compound 18 with that of other compounds in inducing neutrophil apoptosis, including which FIG. 5A showed the result of negative control, FIG. 5B showed the result of LPS (1 μg/mL), FIG. 5C showed the result of LPS (5 μg/mL), FIG. 5D showed the result of LPS (10 μg/mL), FIG. 5E showed the result of compound 18 (0.5 μM), FIG. 5F showed the result of compound 18 (2 μM), FIG. 5G showed the result of compound 18 (10 μM), FIG. 5H showed the result of Roscovitine (20 μM), and FIG. 5I showed the apoptosis percentage vs various compounds.
Figure 5B:
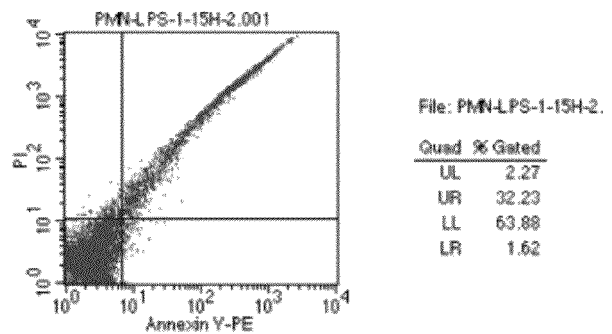
Figure 5C:
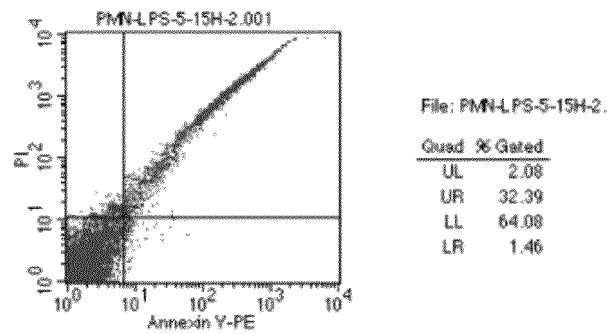
Figure 5D:
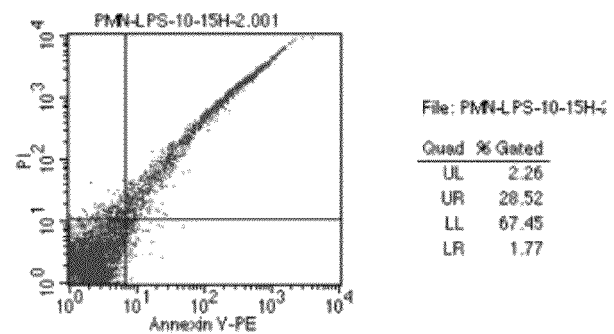
Figure 5E:
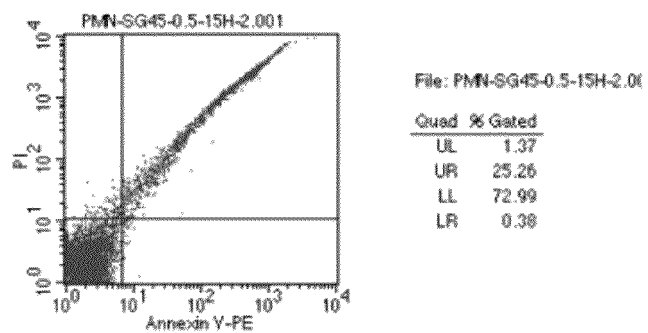
Figure 5F:
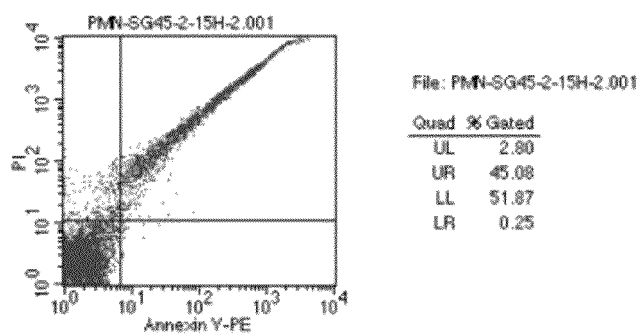

Harvest neutrophils by centrifugation at 1,000 rpm, 4□ for 7 min Remove culture medium after centrifugation. Wash the cell pellet with pre-cooled PBS 200□l once. The re-suspend the cells with pre-cooled PBS 100□l. Incubate the cells with 2□l dye PI (BD Biosciences. Cat. No. 556463) and 2□l anti-Annexin V-PE (BD Biosciences. Cat. No. 556421) at room temperature under the darkness for 30 minutes. Remove the antibodies by centrifugation at 1,000 rpm, 4□ for 2 min. Resuspend the cells in 200□l pre-cooled PBS Finally, load the cell suspension to the FACS machine to acquire the staining results:

Results see FIG. 3.
It showed that healthy neutrophil quickly went into apoptosis in 48 h without any compound stimulation.
Results see FIG. 4.
It showed that with increasing dose of compound 18, typical apoptotic morphological changes, including blebbing, loss of cell membrane asymmetry and attachment, cell shrinkage etc. were observed.
Results see FIG. 5.
Compound 18 showed stronger capability in inducing neutrophil apoptosis than Roscovitine in 15 h.
The examples and embodiments described herein are for illustrative purposes only and various modifications or changes suggested to persons skilled in the art are to be included within the spirit and purview of this application and scope of the appended claims.

What is claimed is:
1. A compound, or pharmaceutically acceptable salt thereof, having the structure of Formula (Ia):

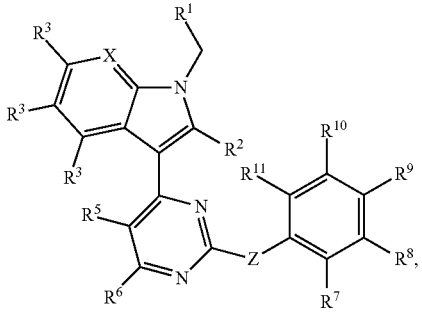

Formula (Ia)

wherein:

X is —N—;

R¹ is unsubstituted $C_1$-$C_6$ alkyl, unsubstituted or substituted aryl, or unsubstituted or substituted heteroaryl;

R², R³, R⁵, R⁶, R⁷, R⁸, R⁹, R¹⁰ and R¹¹ are each independently selected from the group consisting of H, halogen, —NH₂, —NO₂, —CN, —OH, —CO₂H, —CONH₂, —SO₃H, —SO₂NH₂, —SO₂CH₃, —OCH₃, —CF₃, —CH₃, and -$L^A$-$L^B$-$R^{32}$;

$L^A$ is a covalent bond or an alkyl group;

$L^B$ is a covalent bond, —O—, —NR³²—, —NH—, —C(=O)—, —C(=O)O—, —OC(=O)—, —C(=O)NR³²—, —C(=O)NH—, —NR³²C(=O)—, —NHC(=O)—, —SO₂—, —SO₂NR³²—, —NR³²SO₂—, —SO₂NH—, or —NHSO₂—;

R³² is H, substituted or unsubstituted alkyl, haloalkyl, substituted or unsubstituted aryl, substituted or unsubstituted heteroaryl, substituted or unsubstituted non-aromatic heterocycle, or substituted or unsubstituted cycloalkyl; wherein any R³² group, when substituted, is substituted with one or more groups selected from halogen, —NH₂, —NO₂, —CN, —OH, —CO₂H, —CONH₂, —SO₃H, —SO₂NH₂, —SO₂CH₃, —OCH₃, and —CF₃;

Z is —NR$^a$C(=O)—, —C(=O)NR$^a$—, —NR$^a$SO₂—, —SO₂NR$^a$—, —NR$^a$CH₂—, —CH₂—, —CH₂CH₂—, —CH=CH—, —CH₂C(=O)NR$^a$—, —NR$^a$C(=O)CH₂—, —SO₂—, or —SO—;

R$^a$ is H or alkyl.

2. The compound of claim 1, wherein:

Z is —NR$^a$—.

3. The compound of claim 1, wherein:

R¹ is unsubstituted $C_1$-$C_6$ alkyl or unsubstituted or substituted phenyl;

each R³ is independently selected from the group consisting of H, halogen, —NH₂, —NO₂, —CN, —OH, —CO₂H, —CONH₂, —SO₃H, —SO₂NH₂, —SO₂CH₃, —OCH₃, —CF₃, and —CH₃;

R², R⁵ and R⁶ are each H;

R⁷, R⁸, R⁹, R¹⁰ and R¹¹ are each independently selected from the group consisting of H, halogen, —NH₂, —NO₂, —CN, —OH, —CO₂H, —CONH₂, —SO₃H, —SO₂NH₂, —SO₂CH₃, —OCH₃, —CF₃, —CH₃, or -$L^A$-$L^B$-$R^{32}$, $L^A$ is a covalent bond or an alkyl group;

$L^B$ is a covalent bond, —O—, —NR³²—, —NH—, —C(=O)O—, —C(=O)NR³²—, —C(=O)NH—, —SO₂NR³²—, or —SO₂NH—;

R³² is H, substituted or unsubstituted alkyl, haloalkyl, substituted or unsubstituted aryl, substituted or unsubstituted heteroaryl, substituted or unsubstituted non-aromatic heterocycle, or substituted or unsubstituted cycloalkyl; wherein any R³² group, when substituted, is substituted with one or more groups selected from halogen, —NH₂, —NO₂, —CN, —OH, —CO₂H, —CONH₂, —SO₃H, —SO₂NH₂, —SO₂CH₃, —OCH₃, and —CF₃.

4. A compound, or pharmaceutically acceptable salt thereof, having the structure of Formula (Ic):

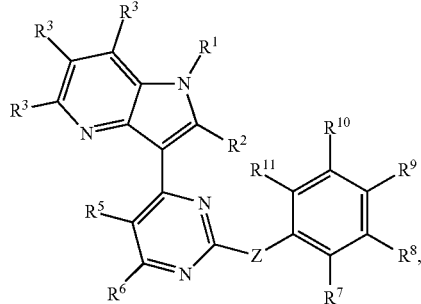

Formula (Ic)

wherein:

R¹, R², R³, R⁵, R⁶, R⁷, R⁸, R⁹, R¹⁰ and R¹¹ are each independently selected from the group consisting of H, halogen, —NH₂, —NO₂, —CN, —OH, —CO₂H, —CONH₂, —SO₃H, —SO₂NH₂, —SO₂CH₃, —OCH₃, —CF₃, —CH₃, and -$L^A$-$L^B$-$R^{32}$;

$L^A$ is a covalent bond or an alkyl group;

$L^B$ is a covalent bond, —O—, —NR³²—, —NH—, —C(=O)—, —C(=O)o—, —OC(=O)—, —C(=O)NR³²—, —C(=O)NH—, —NR³²C(=O)—, —NHC(=O)—, —SO₂—, —SO₂NR³²—, —NR³²SO₂—, —SO₂NH—, or —NHSO₂—;

R³² is H, substituted or unsubstituted alkyl, haloalkyl, substituted or unsubstituted aryl, substituted or unsubstituted heteroaryl, substituted or unsubstituted non-aromatic heterocycle, or substituted or unsubstituted cycloalkyl; wherein any R³² group, when substituted, is substituted with one or more groups selected from halogen, —NH₂, —NO₂, —CN, —OH, —CO₂H, —CONH₂, —SO₃H, —SO₂NH₂, —SO₂CH₃, —OCH₃, and —CF₃;

Z is —NR$^a$C(=O)—, —C(=O)NR$^a$—, —NR$^a$SO₂—, —SO₂NR$^a$—, —NR$^a$—, —CH₂NR$^a$—, —NR$^a$CH₂—, —CH₂—, —CH₂CH₂—, —CH=CH—, —CH₂C(=O)Nle-, —NR$^a$C(=O)CH₂—, —SO₂—, or —SO—;

R$^a$ is H or alkyl.

5. The compound of claim 4, wherein:

Z is —NR$^a$—.

6. The compound of claim 5, wherein:

R¹ is unsubstituted $C_1$-$C_6$ alkyl;

each R³ is independently selected from the group consisting of H, halogen, —NH₂, —NO₂, —CN, —OH, —CO₂H, —CONH₂, —SO₃H, —SO₂NH₂, —SO₂CH₃, —OCH₃, —CF₃, and —CH₃;

R², R⁵ and R⁶ are each H;

R⁷, R⁸, R⁹, R¹⁰ and R¹¹ are each independently selected from the group consisting of H, halogen, —NH₂, —NO₂, —CN, —OH, —CO₂H, —CONH₂, —SO₃H, —SO₂NH₂, —SO₂CH₃, —OCH₃, —CF₃, —CH₃, and -$L^A$-$L^B$-$R^{32}$, L^A is a covalent bond or an alkyl group;
L^B is a covalent bond, —O—, —NR^32—, —NH—, —C(=O)O—, —C(=O)NR^32—, —C(=O)NH—, —SO_2NR^32—, or —SO_2NH—;
R^32 is H, substituted or unsubstituted alkyl, haloalkyl, substituted or unsubstituted aryl, substituted or unsubstituted heteroaryl, substituted or unsubstituted non-aromatic heterocycle, or substituted or unsubstituted cycloalkyl; wherein any R^32 group, when substituted, is substituted with one or more groups selected from halogen, —NH_2, —NO_2, —CN, —OH, —CO_2H, —CONH_2, —SO_3H, —SO_2NH_2, —SO_2CH_3, —OCH_3, and —CF_3.

7. A compound selected from:
4-[4-(1-Ethyl-1H-pyrrolo[2,3-b]pyridin-3-yl)-pyrimidin-2-ylamino]-phenol (Compound 12),
3-[4-(1-Ethyl-1H-pyrrolo[2,3-b]pyridin-3-yl)-pyrimidin-2-ylamino]-phenol (Compound 13),
[4-(1-Ethyl-1H-pyrrolo[2,3-b]pyridin-3-yl)-pyrimidin-2-yl]-(3-nitro-phenyl)-amine (Compound 14),
4-[4-(1-Propyl-1H-pyrrolo[2,3-b]pyridin-3-yl)-pyrimidin-2-ylamino]-phenol (Compound 15),
3-[4-(1-Propyl-1H-pyrrolo[2,3-b]pyridin-3-yl)-pyrimidin-2-ylamino]-phenol (Compound 16),
(3-Nitro-phenyl)-[4-(1-propyl-1H-pyrrolo[2,3-b]pyridin-3-yl)-pyrimidin-2-yl]-amine (Compound 17),
3-(4-(1-Ethyl-1H-pyrrolo[2,3-b]pyridin-3-yl)pyrimidin-2-ylamino)benzenesulfonamide (Compound 18),
3-(4-(1-Ethyl-1H-pyrrolo[2,3-b]pyridin-3-yl)pyrimidin-2-ylamino)benzamide (Compound 19),
3-(4-(1-ethyl-1H-pyrrolo[2,3-b]pyridin-3-yl)pyrimidin-2-ylamino)benzonitrile (Compound 20),
4-(4-(1-ethyl-1H-pyrrolo[2,3-b]pyridin-3-yl)pyrimidin-2-ylamino)benzenesulfonamide (Compound 21),
3-(4-(1-propyl-1H-pyrrolo[2,3-b]pyridin-3-yl)pyrimidin-2-ylamino)benzenesulfonamide (Compound 22),
4-(4-(1-Propyl-1H-pyrrolo[2,3-b]pyridin-3-yl)pyrimidin-2-ylamino)benzenesulfonamide (Compound 23),
N-(4-Methyl-3-(morpholinosulfonyl)phenyl)-4-(1-propyl-1H-pyrrolo[2,3-b]pyridin-3-yl)pyrimidin-2-amine (Compound 24),
N-(3-(piperazin-1-ylsulfonyl)phenyl)-4-(1-propyl-1H-pyrrolo[2,3-b]pyridin-3-yl)pyrimidin-2-amine (Compound 25),
N-(4-(piperazin-1-ylsulfonyl)phenyl)-4-(1-propyl-1H-pyrrolo[2,3-b]pyridin-3-yl)pyrimidin-2-amine (Compound 26),
N-(4-(Morpholinosulfonyl)phenyl)-4-(1-propyl-1H-pyrrolo[2,3-b]pyridin-3-yl)pyrimidin-2-amine (Compound 27),
N-(3-(4-Methylpiperazin-1-ylsulfonyl)phenyl)-4-(1-propyl-1H-pyrrolo[2,3-b]pyridin-3-yl)pyrimidin-2-amine (Compound 28),
N-(4-(4-Methylpiperazin-1-ylsulfonyl)phenyl)-4-(1-propyl-1H-pyrrolo[2,3-b]pyridin-3-yl)pyrimidin-2-amine (Compound 29),
N-(3-Morpholinophenyl)-4-(1-propyl-1H-pyrrolo[2,3-b]pyridin-3-yl)pyrimidin-2-amine (Compound 30),
N-(4-Morpholinophenyl)-4-(1-propyl-1H-pyrrolo[2,3-b]pyridin-3-yl)pyrimidin-2-amine (Compound 31),
N-(3-(piperazin-1-yl)phenyl)-4-(1-propyl-1H-pyrrolo[2,3-b]pyridin-3-yl)pyrimidin-2-amine (Compound 32),
N-(4-(piperazin-1-yl)phenyl)-4-(1-propyl-1H-pyrrolo[2,3-b]pyridin-3-yl)pyrimidin-2-amine (Compound 33),
(4-Methylpiperazin-1-yl)(3-(4-(1-propyl-1H-pyrrolo[2,3-b]pyridin-3-yl)pyrimidin-2-ylamino)phenyl)methanone (Compound 34),
N-(4-(4-Methylpiperazin-1-yl)phenyl)-4-(1-propyl-1H-pyrrolo[2,3-b]pyridin-3-yl)pyrimidin-2-amine (Compound 35),
1-(4-(3-(4-(1-Propyl-1H-pyrrolo[2,3-b]pyridin-3-yl)pyrimidin-2-ylamino)phenyl)piperazin-1-yl)ethanone (Compound 36),
1-(4-(4-(4-(1-Propyl-1H-pyrrolo[2,3-b]pyridin-3-yl)pyrimidin-2-ylamino)phenyl)piperazin-1-yl)ethanone (Compound 37),
4-(4-(5-Chloro-7-methyl-1-propyl-1H-pyrrolo[3,2-b]pyridin-3-yl)pyrimidin-2-ylamino)phenol (Compound 38),
4-(4-(5-Chloro-7-methyl-1-propyl-1H-pyrrolo[3,2-b]pyridin-3-yl)pyrimidin-2-ylamino)benzenesulfonamide (Compound 39),
3-(4-(5-Chloro-7-methyl-1-propyl-1H-pyrrolo[3,2-b]pyridin-3-yl)pyrimidin-2-ylamino)phenol (Compound 40),
4-(4-(5-Chloro-7-methyl-1-propyl-1H-pyrrolo[3,2-b]pyridin-3-yl)pyrimidin-2-ylamino)-3-methylphenol (Compound 41),
3-(4-(5-Chloro-7-methyl-1-propyl-1H-pyrrolo[3,2-b]pyridin-3-yl)pyrimidin-2-ylamino)benzenesulfonamide (Compound 42),
4-(5-Chloro-7-methyl-1-propyl-1H-pyrrolo[3,2-b]pyridin-3-yl)-N-(4-methyl-3-(morpholinosulfonyl)phenyl)pyrimidin-2-amine (Compound 43),
4-(5-Chloro-7-methyl-1-propyl-1H-pyrrolo[3,2-b]pyridin-3-yl)-N-(3-(piperazin-1-ylsulfonyl)phenyl)pyrimidin-2-amine (Compound 44),
4-(5-Chloro-7-methyl-1-propyl-1H-pyrrolo[3,2-b]pyridin-3-yl)-N-(4-(piperazin-1-ylsulfonyl)phenyl)pyrimidin-2-amine (Compound 45),
4-(5-Chloro-7-methyl-1-propyl-1H-pyrrolo[3,2-b]pyridin-3-yl)-N-(3-(piperazin-1-yl)phenyl)pyrimidin-2-amine (Compound 46),
4-(5-Chloro-7-methyl-1-propyl-1H-pyrrolo[3,2-b]pyridin-3-yl)-N-(4-(piperazin-1-yl)phenyl)pyrimidin-2-amine (Compound 47),
4-(5-Chloro-7-methyl-1-propyl-1H-pyrrolo[3,2-b]pyridin-3-yl)-N-(3-morpholinophenyl)pyrimidin-2-amine (Compound 48),
4-(5-Chloro-7-methyl-1-propyl-1H-pyrrolo[3,2-b]pyridin-3-yl)-N-(4-morpholinophenyl)pyrimidin-2-amine (Compound 49),
1-(4-(3-(4-(5-Chloro-7-methyl-1-propyl-1H-pyrrolo[3,2-b]pyridin-3-yl)pyrimidin-2-ylamino)phenyl)piperazin-1-yl)ethanone (Compound 50),
1-(4-(4-(4-(5-Chloro-7-methyl-1-propyl-1H-pyrrolo[3,2-b]pyridin-3-yl)pyrimidin-2-ylamino)phenyl)piperazin-1-yl)ethanone (Compound 51),
(3-(4-(5-Chloro-7-methyl-1-propyl-1H-pyrrolo[3,2-b]pyridin-3-yl)pyrimidin-2-ylamino)phenyl)(morpholino)methanone (Compound 52),
(4-(4-(5-Chloro-7-methyl-1-propyl-1H-pyrrolo[3,2-b]pyridin-3-yl)pyrimidin-2-ylamino)phenyl)(morpholino)methanone (Compound 53),
3-(4-(7-Methyl-1-propyl-1H-pyrrolo[3,2-b]pyridin-3-yl)pyrimidin-2-ylamino)benzenesulfonamide (Compound 54),
4-(4-(7-Methyl-1-propyl-1H-pyrrolo[3,2-b]pyridin-3-yl)pyrimidin-2-ylamino)benzenesulfonamide (Compound 55),
4-(7-Methyl-1-propyl-1H-pyrrolo[3,2-b]pyridin-3-yl)-N-(3-(piperazin-1-ylsulfonyl)phenyl)pyrimidin-2-amine (Compound 56), 4(7-Methyl-1-propyl-1H-pyrrolo[3,2-b]pyridin-3-yl)-N-(4-(piperazin-1-ylsulfonyl)phenyl)pyrimidin-2-amine (Compound 57), 4(7-Methyl-1-propyl-1H-pyrrolo[3,2-b]pyridin-3-yl)-N-[3-(piperazin-1-yl)phenyl)pyrimidin-2-amine (Compound 58), 4-(7-Methyl-1-propyl-1H-pyrrolo[3,2-b]pyridin-3-yl)-N-[4-(piperazin-1-yl)phenyl)pyrimidin-2-amine (Compound 59), 4-(7-Methyl-1-propyl-1H-pyrrolo[3,2-b]pyridin-3-yl)-N-(3-morpholinophenyl)pyrimidin-2-amine (Compound 60), 4-(7-Methyl-1-propyl-1H-pyrrolo[3,2-b]pyridin-3-yl)-N-(4-morpholinophenyl)pyrimidin-2-amine (Compound 61), 1-(4-(3-(4-(7-Methyl-1-propyl-1H-pyrrolo[3,2-b]pyridin-3-yl)pyrimidin-2-ylamino)phenyl)piperazin-1-yl)ethanone (Compound 62), 1-(4-(4-(4-(7-Methyl-1-propyl-1H-pyrrolo[3,2-b]pyridin-3-yl)pyrimidin-2-ylamino)phenyl)piperazin-1-yl)ethanone (Compound 63), 3-(4-(1-Ethyl-7-methyl-1H-pyrrolo[3,2-b]pyridin-3-yl)pyrimidin-2-ylamino)benzenesulfonamide (Compound 64), 4-(4-(1-Ethyl-7-methyl-1H-pyrrolo[3,2-b]pyridin-3-yl)pyrimidin-2-ylamino)benzenesulfonamide (Compound 65), (3-(4-(1-Ethyl-7-methyl-1H-pyrrolo[3,2-b]pyridin-3-yl)pyrimidin-2-ylamino)phenyl)(morpholino)methanone (Compound 66), (4-(4-(1-Ethyl-7-methyl-1H-pyrrolo[3,2-b]pyridin-3-yl)pyrimidin-2-ylamino)phenyl)(morpholino)methanone (Compound 67), 4-(1-Ethyl-7-methyl-1H-pyrrolo[3,2-b]pyridin-3-yl)-N-(3-(piperazin-1-yl)phenyl)pyrimidin-2-amine (Compound 68), and 4-(1-Ethyl-7-methyl-1H-pyrrolo[3,2-b]pyridin-3-yl)-N-(4-(piperazin-1-yl)phenyl)pyrimidin-2-amine (Compound 69).

8. A pharmaceutical composition comprising a compound of claim 1, 4, or 7 and a pharmaceutically excipient.

9. The pharmaceutical composition of claim 8, wherein the pharmaceutical composition is in the form of an aqueous dispersion, liquid, gel, syrup, elixir, slurry, suspension, aerosol, controlled release formulation, fast melt formulation, effervescent formulation, lyophilized formulation, tablet, powder, pill, dragee, capsule, delayed release formulation, extended release formulation, pulsatile release formulation, multiparticulate formulation, or immediate release formulation.

* * * * *